US009387242B2

(12) United States Patent
Palese et al.

(10) Patent No.: US 9,387,242 B2

(45) Date of Patent: Jul. 12, 2016

(54) CHIMERIC VIRUSES PRESENTING NON-NATIVE SURFACE PROTEINS AND USES THEREOF

(75) Inventors: Peter Palese, Leonia, NJ (US); Adolfo Garcia-Sastre, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 2516 days.

(21) Appl. No.: 11/633,130

(22) Filed: Dec. 1, 2006

(65) Prior Publication Data

US 2012/0122185 A1 May 17, 2012

Related U.S. Application Data

(60) Provisional application No. 60/741,833, filed on Dec. 2, 2005, provisional application No. 60/802,864, filed on May 22, 2006.

(51) Int. Cl.

| | |
|---|---|
| ***A61K 39/17*** | (2006.01) |
| ***A61K 39/145*** | (2006.01) |
| ***C07K 14/005*** | (2006.01) |
| ***A61K 39/12*** | (2006.01) |
| *A61K 39/00* | (2006.01) |

(52) U.S. Cl.

CPC ................ *A61K 39/17* (2013.01); *A61K 39/12* (2013.01); *A61K 39/145* (2013.01); *C07K 14/005* (2013.01); *A61K 2039/5256* (2013.01); *A61K 2039/541* (2013.01); *A61K 2039/552* (2013.01); *A61K 2039/70* (2013.01); *C07K 2319/03* (2013.01); *C12N 2760/16122* (2013.01); *C12N 2760/16134* (2013.01); *C12N 2760/16143* (2013.01); *C12N 2760/18122* (2013.01); *C12N 2760/18134* (2013.01); *C12N 2760/18143* (2013.01)

(58) Field of Classification Search

None

See application file for complete search history.

(56) References Cited

U.S. PATENT DOCUMENTS

| | | | | |
|---|---|---|---|---|
| 4,071,618 | A | 1/1978 | Konobe et al. | |
| 4,693,981 | A | 9/1987 | Wiesehahn et al. | |
| 5,106,619 | A | 4/1992 | Wiesehahn et al. | |
| 5,166,057 | A | 11/1992 | Palese et al. | |
| 5,716,821 | A | 2/1998 | Wertz et al. | |
| 5,786,199 | A | 7/1998 | Palese et al. | |
| 5,820,871 | A | 10/1998 | Palese et al. | |
| 5,840,520 | A | 11/1998 | Palese et al. | |
| 5,854,037 | A | 12/1998 | Palese et al. | |
| 5,891,705 | A | 4/1999 | Budowsky et al. | |
| 6,001,634 | A | 12/1999 | Palese et al. | |
| 6,033,886 | A | 3/2000 | Conzelmann | |
| 6,146,642 | A | 11/2000 | Garcia-Sastre et al. | |
| 6,300,090 | B1 | 10/2001 | Steinman et al. | |
| 6,451,323 | B1 | 9/2002 | Garcia-Sastre et al. | |
| 6,468,544 | B1 | 10/2002 | Egorov et al. | |
| 6,544,785 | B1 | 4/2003 | Palese et al. | |
| 6,573,079 | B1 | 6/2003 | Palese et al. | |
| 6,635,246 | B1 | 10/2003 | Barrett et al. | |
| 6,635,416 | B2 | 10/2003 | Palese et al. | |
| 6,649,372 | B1 | 11/2003 | Palese et al. | |
| 6,669,943 | B1 | 12/2003 | Palese et al. | |
| 6,852,522 | B1 | 2/2005 | Palese et al. | |
| 6,866,853 | B2 | 3/2005 | Egorov et al. | |
| 6,884,414 | B1 | 4/2005 | Palese et al. | |
| 6,887,699 | B1 | 5/2005 | Palese et al. | |
| 7,060,430 | B2 | 6/2006 | Palese et al. | |
| 7,384,774 | B2 | 6/2008 | Palese et al. | |
| 7,442,527 | B2 | 10/2008 | Palese et al. | |
| 7,494,808 | B2 | 2/2009 | Palese et al. | |
| 7,588,768 | B2 | 9/2009 | Palese et al. | |
| 8,057,803 | B2 | 11/2011 | Palese et al. | |
| 2003/0078410 | A1 | 4/2003 | Garcia-Sastre et al. | |
| 2003/0087417 | A1* | 5/2003 | Peeters et al. | 435/235.1 |
| 2004/0109877 | A1 | 6/2004 | Palese et al. | |
| 2004/0142003 | A1 | 7/2004 | Palese et al. | |
| 2004/0241139 | A1 | 12/2004 | Hobom et al. | |
| 2004/0253273 | A1 | 12/2004 | Paleso et al. | |

(Continued)

FOREIGN PATENT DOCUMENTS

| | | |
|---|---|---|
| CA | 2118234 | 10/1993 |
| EP | 0279563 | 8/1988 |

(Continued)

OTHER PUBLICATIONS

International Search Report for International Application No. PCT/US1999/021081, Jan. 21, 2000.

International Preliminary Examination Report for PCT/US1999/021081, Jul. 1, 2002.

International Search Report and Written Opinion for International Application No. PCT/US06/45859, Mar. 28, 2007.

Bukreyev et al., Recombinant respiratory syncytial virus from which the entire SH gene has been deleted grows efficiently in cell culture and exhibits site-specific attenuation in the respiratory tract of the mouse. J Virol. Dec. 1997;71(12):8973-82.

Bukreyev et al., Recovery of infectious respiratory syncytial virus expressing an additional, foreign gene. J Virol. Oct. 1996:70(10):6634-41.

(Continued)

*Primary Examiner* — Benjamin P Blumel

(74) *Attorney, Agent, or Firm* — Jones Day

(57) ABSTRACT

The present invention provides chimeric negative-stand RNA viruses that allow a subject, e.g., an avian, to be immunized against two infectious agents by using a single chimeric virus of the invention. In particular, the present invention provides chimeric influenza viruses engineered to express and incorporate into their virions a fusion protein comprising an ectodomain of a protein of an infectious agent and the transmembrane and cytoplasmic domain of an influenza virus protein. Such chimeric viruses induce an immune response against influenza virus and the infectious agent. The present invention also provides chimeric Newcastle Disease viruses (NDV) engineered to express and incorporate into their virions a fusion protein comprising the ectodomain of a protein of an infectious agent and the transmembrane and cytoplasmic domain of an NDV protein. Such chimeric viruses induce an immune response against NDV and the infectious agent.

43 Claims, 10 Drawing Sheets

(56) References Cited

U.S. PATENT DOCUMENTS

| | | | | |
|---|---|---|---|---|
| 2005/0054074 | A1 | 3/2005 | Palese et al. | |
| 2005/0158338 | A1* | 7/2005 | Buchholz et al. | 424/199.1 |
| 2005/0186621 | A1 | 8/2005 | Galarza | |
| 2005/0221489 | A1 | 10/2005 | Garcia-Sastre et al. | |
| 2006/0216701 | A1 | 9/2006 | Palese et al. | |
| 2009/0028901 | A1 | 1/2009 | Palese et al. | |
| 2009/0053264 | A1 | 2/2009 | Palese et al. | |
| 2009/0203114 | A1 | 8/2009 | Palese et al. | |
| 2009/0214590 | A1 | 8/2009 | Sundick et al. | |
| 2010/0080827 | A1 | 4/2010 | Palese et al. | |
| 2010/0092430 | A1 | 4/2010 | Beier et al. | |
| 2010/0158942 | A1 | 6/2010 | Palese et al. | |
| 2010/0233785 | A1 | 9/2010 | Brandt et al. | |
| 2011/0020282 | A1 | 1/2011 | Beier et al. | |
| 2012/0058141 | A1 | 3/2012 | Palese et al. | |
| 2012/0258134 | A1 | 10/2012 | Palese et al. | |

FOREIGN PATENT DOCUMENTS

| | | |
|---|---|---|
| EP | 0702085 | 3/1996 |
| EP | 0780475 | 6/1997 |
| EP | 0 974 660 | 1/2000 |
| EP | 1 962 893 | 9/2008 |
| EP | 2251034 | 11/2010 |
| WO | WO 96/10632 | 4/1996 |
| WO | WO 96/34625 | 11/1996 |
| WO | WO 97/06270 | 2/1997 |
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 99/64068 | 12/1999 |
| WO | WO 99/64570 | 12/1999 |
| WO | WO 99/64571 | 12/1999 |
| WO | WO 99/66045 | 12/1999 |
| WO | WO 00/15853 | 3/2000 |
| WO | WO 00/60050 | 4/2000 |
| WO | WO 00/53786 | 9/2000 |
| WO | WO 01/04333 | 1/2001 |
| WO | WO 01/64860 | 9/2001 |
| WO | WO 01/77394 | 10/2001 |
| WO | WO 02/36617 | 5/2002 |
| WO | WO 2005/116258 | 12/2005 |
| WO | WO 2007/064802 | 6/2007 |
| WO | WO 2007/104782 | 9/2007 |

OTHER PUBLICATIONS

Chanda et al., In vitro transcription of defective interfering particles of influenza virus produces polyadenylic acid-containing complementary RNAs. J Virol. Jan. 1983;45(1):55-61.

Chen et al. Avian flu: H5N1 virus outbreak in migratory waterfowl. Nature. Jul. 14, 2005:436(7048):191-2.

Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88:9663-9667.

Collins et al., 1996, "Parainfluenza Viruses", Fields Virology (Lippincott-Raven Publishers, Philadelphia) pp. 1205-1241.

Crowe et al., Acquisition of the ts phenotype by a chemically mutagenized cold-passaged human respiratory syncytial virus vaccine candidate results from the acquisition of a single mutation in the polymerase (L) gene. Virus Genes. 1996;13(3):269-73.

De and Banerjee, 1985, "Requirements and Functions of Vesicular Stomatitis Virus L and NS Proteins in the Transcription Process in Vitro", Biochem. Biophys. Res. Comm. 126:40-49.

Desrosiers et al., 1987, "Animal models for acquired immunodeficiency syndrome", Rev Infect Dis. 9(3):438-46.

Dreher and Hall, 1988, "Mutational Analysis of the Sequence and Structural Requirements in Brome Mosaic Virus RNA for Minus Strand Promoter Activity", J. Mol. Biol. 201:31-40.

Dreher et al., 1984, "Mutant Viral RNAs Synthesized in Vitro Show Altered Aminoacylation and Replicase Template Activities", Nature 311:171-175.

Ellis et al. Vaccination of chickens against H5N1 avian influenza in the face of an outbreak interrupts virus transmission. Avian Pathol. Aug. 2004;33(4):405-12.

Emerson and Yu, 1975, "Both NS and L Proteins Are Required for In Vitro RNA Synthesis by Vesicular Stomatitis Virus", J. Virol. 15:1348-1356.

Enami et al., An influenza virus containing nine different RNA segments. Virology. Nov. 1991;185(1):291-8. Erratum in: Virology Feb. 1992;186(2):798.

Enami et al.. 1990, "Introduction of Site-Specific Mutations into the Genome of Influenza Virus", Proc. Natl. Acad. Sci. USA 87:3802-3805.

Enami et al., High-efficiency formation of influenza virus transfectants. J Virol. May 1991;65(5):271 1-3.

Enserink M. Avian influenza. H5N1 moves into Africa, European Union, deepening global crisis. Science. Feb. 17, 2006;311(5763):932.

Fahey, J. and Schooley, R., 1992, "Status of Immune-based Therapies in HIV Infection and AIDS" Clin. Exp. Immunol. 88:1-5.

Fields et al., Nucleotide sequences of influenza virus segments 1 and 3 reveal mosaic structure of a small viral RNA segment. Cell. Feb. 1982;28(2):303-13.

Flandorfer et al. Chimeric influenza A viruses with a functional influenza B virus neuraminidase or hemagglutinin. J Virol. Sep. 2003;77(17):9116-23.

Fodor et al. Rescue of influenza A virus from recombinant DNA. J Virol. Nov. 1999:73(11):9679-82.

Fujii et al. Selective incorporation of influenza virus RNA segments into virions. Proc Natl Acad Sci USA. Feb. 18, 2003;100(4):2002-7.

Garcia-Sastre A and Palese P. The cytoplasmic tail of the neuraminidase protein of influenza A virus does not play an important role in the packaging of this protein into viral envelopes. Virus Res. Jun. 1995;37(1):37-47.

Garcia-Sastre A. Mechanisms of inhibition of the host interferon alpha/beta-mediated antiviral responses by viruses. Microbes Infect. May 2002;4(6):647-55. Review.

Garcia-Sastre et al. Influenza A virus lacking the NS1 gene replicates in interferon-deficient systems. Virology. Dec. 20, 1998;252(2):324-30.

Garcia-Sastre et al. Introduction of foreign sequences into the genome of influenza A virus. Dev Biol Stand. 1994;82:237-46.

Garcia-Sastre et al. Use of a mammalian internal ribosomal entry site element for expression of a foreign protein by a transfectant influenza virus. J Virol. Oct. 1994;68(10):6254-61.

Garcia-Sastre et al., Genetic manipulation of negative-strand RNA virus genomes. Annu Rev Microbiol. 1993;47:765-90.

Genbank Accession No. AF309418, Newcastle disease virus B1, complete genome, dated Dec. 2, 2000.

Genbank Accession No. AF375823, Newcastle disease virus strain B1 isolate Takaaki, complete genome, dated Nov. 6, 2001.

Genbank Accession No. AY646080, Influenza A virus (A/chicken/British Columbia/GSC_human_B/04(H7N3)) neuraminidase (NA) gene, complete cds, dated Dec. 14, 2004.

Genbank Accession No. AY651388, Influenza A virus (A/Viet Nam/1203/2004(H5N1)) membrane ion channel 2 (M) and matrix protein 1 (M) genes, complete cds, dated Jul. 10, 2007.

Genbank Accession No. AY651447, Influenza A virus (A/Viet Nam/1203/2004(H5N1)) neuraminidase (NA) gene, complete cds, dated Jul. 10, 2007.

Genbank Accession No. AY651499, Influenza A virus (A/Viet Nam/1203/2004(H5N1)) nucleocapsid protein (NP) gene, partial cds, dated Jul. 16, 2004.

Genbank Accession No. AY651719, Influenza A virus (A/Viet Nam/1203/2004(H5N1)) polymerase basic subunit 2 (PB2) gene, complete cds, dated Jul. 16, 2004.

Genbank Accession No. AY706954, Influenza A virus (A/duck/Hainan/4/2004(H6N2)) neuraminidase (NA) gene, complete cds, dated Sep. 13, 2004.

(56) References Cited

OTHER PUBLICATIONS

Genbank Accession No. AY818129, Influenza A virus (A/Viet Nam/1203/2004(H5N1)) polymerase protein PB1 gene. complete cds, dated Feb. 9, 2005.
Genbank Accession No. AY818132, Influenza A virus (A/Viet Nam/1203/2004(H5N1)) polymerase protein PA gene, complete cds, dated Feb. 9, 2005.
Genbank Accession No. AY818135, Influenza A virus (A/Viet Nam/1203/2004(H5N1)) hemagglutinin HA gene, complete cds, dated Feb. 9. 2005.
Genbank Accession No. AY968677, Influenza A virus (A/turkey/Canada/63(H6N2)) neuraminidase (NA) gene, complete cds, dated Apr. 11, 2005.
Genbank Accession No. CQ867238, Sequence 12 from Patent EP1454989, synthetic construct, dated Sep. 13, 2004.
Genbank Accession No. DQ064434, Influenza A virus (A/chicken/Beijing/8/98(H9N2)) neuraminidase (NA) gene, complete cds, dated Sep. 7, 2005.
Genbank Accession No. L25817, Influenza A virus (A/WSN/1933(H1N1)) neuraminidase gene, complete cds, dated May 2, 2006.
Genbank Accession No. AY651553, Influenza A virus (A/Viet Nam/1203/2004(H5N1)) nonstructural protein 2 (NS) gene, complete cds; and nonfunctional nonstructural protein 1 (NS) gene, complete sequence, dated Jul. 14, 2004.
Gorse and Belshe, Enhancement of anti-influenza A virus cytotoxicity following influenza A virus vaccination in older, chronically ill adults. J Clin Microbiol. Nov. 1990;28(11):2539-50.
Gorse et al. Increased anti-influenza A virus cytotoxic T cell activity following vaccination of the chronically ill elderly with live attenuated or inactivated influenza virus vaccine. J Infect Dis. Jul. 1995;172(1):1-10.
Hoffmann et al. A DNA transfection system for generation of influenza A virus from eight plasmids. Proc Natl Acad Sci U S A. May 23, 2000;97(11):6108-13.
Horimoto et al., Influenza A viruses possessing type B hemagglutinin and neuraminidase: potential as vaccine components. Microbes Infect. May 2004;6(6):579-83.
Horimoto T and Kawaoka Y., Reverse genetics provides direct evidence for a correlation of hemagglutinin cleavability and virulence of an avian influenza A virus. J Virol. May 1994;68(5):3120-8.
Horimoto T, Kawaoka Y. Influenza: lessons from past pandemics, warnings from current incidents. Nat Rev Microbiol. Aug. 2005;3(8):591-600. Review.
Kaplan et al., 1985, "In Vitro Synthesis of Infectious Poliovirus RNA", Proc. Natl. Acad. Sci. USA 82:8424-8428.
Katinger et al., 1997, "Attenuated Influenza Virus as a vector for Mucosal Immunization against HIV-1." Vaccines, 315-319.
Kato et al., 1996 "Initiation of Sendai Virus Multiplication from Transfected cDNA or RNA with Negative or Positive Sense", Genes Cells 1:569-579.
Koike et al., 1991, "Transgenic mice susceptible to poliovirus", Proc Nati Acad Sci U S A. 88(3):951-5.
Koopmans et al. Transmission of H7N7 avian influenza A virus to human beings during a large outbreak in commercial poultry farms in the Netherlands. Lancet. Feb. 21, 2004;363(9409):587-93.
Krug, Transcription and Replication of Influenza Viruses, In Genetics of Influenza Viruses. Ed., Palese, P. and Kingsbury, D. W., New York, Springer-Verlag, 1983. pp. 70-98.
Krystal et al., "Expression of the Three Influenza Virus Polymerase Proteins in a Single Cell Allows Growth Complementation of Viral Mutants", 1986, Proc. Natl. Acad. Sci. USA 83:2709-2713.
Kunkel, 1985, "Rapid and Efficient Site-Specific Mutagenesis without Phenotypic Selection", Proc. Natl. Acad. Sci. USA 82:488-492.
Lamb RA and Choppin PW, The gene structure and replication of influenza virus. Annu Rev Biochem. 1983; 52:467-506. Review.
Levis et al., 1986, "Deletion Mapping of Sindbis Virus D1 RNAs Derived from cDNAs Defines the Sequences Essential for Replication and Packaging", Cell 44:137-145.
Li et al. Recombinant influenza A virus vaccines for the pathogenic human A/Hong Kong/97(H5N1) viruses. J Infect Dis. May 1999;179(5):1132-8.
Lipatov et al. Influenza: emergence and control. J Virol. Sep. 2004;78(17):8951-9. Review.
Luytjes et al., 1989, "Amplification, Expression, and Packaging of a Foreign Gene by Influenza Virus", Cell 59:1 107-1113.
Maeda et al., Live bivalent vaccine for parainfluenza and influenza virus infections. J Virol. Jun. 2005;79(11):6674-9.
Mani et al., 1996, "Effect of age and route of inoculation on outcome of neonatal herpes simplex virus infection in guinea pigs", J Med Virol. Mar. 1996;48(3):247-52.
Meehan et al., 1997, "Investigation of the attenuation exhibited by a molecularly cloned chicken anemia virus isolate by utilizing a chimeric virus approach", J Virol. 71(11):8362-7.
Mena et al., Rescue of a synthetic chloramphenicol acetyltransferase RNA into influenza virus-like particles obtained from recombinant plasmids. J Virol. Aug. 1996;70(8):5016-24.
Morgan et al., Applications of the polymerase chain reaction in retroviral-mediated gene transfer and the analysis of gene-marked human TIL cells. Hum Gene Ther. 1990 Summer;1(2):135-49.
Morgan et al., 1988, "Prevention of Epstein-Barr (EB) virus-induced lymphoma in cottontop tamarins by vaccination with the EB virus envelope glycoprotein gp340 incorporated into immune-stimulating complexes", J Gen Virol. 69 (Pt 8):2093-6.
Muster et al., An influenza A virus containing influenza B virus 5' and 3' noncoding regions on the neuraminidase gene is attenuated in mice. Proc Natl Acad Sci U S A. Jun. 15, 1991;88(12):5177-81.
Naito and Ishihama, 1976, "Function and Structure of RNA Polymerase from Vesicular Stomatitis Virus", J. Biol. Chem. 251:4307-4314.
Nakaya et al. Induction of cellular immune responses to simian immunodeficiency virus gag by two recombinant negative-strand RNA virus vectors. J Virol. Sep. 2004;78(17):9366-75.
Nakaya et al. Recombinant Newcastle disease virus as a vaccine vector. J Virol. Dec. 2001:75(23):11868-73.
Nara et al., 1987, "Simple, Rapid, Quantitative, Syncytium-Forming Microassay for the Detection of Human Immunodeficiency Virus Neutralizing Antibody", AIDS Res. Hum. Retroviruses 3:283-302.
Nelson et al. Local and systemic isotype-specific antibody responses to equine influenza virus infection versus conventional vaccination. Vaccine. Aug. 1998;16(13):1306-13.
Neumann et al. Generation of influenza A viruses entirely from cloned cDNAs. Proc Natl Acad Sci U S A. Aug. 3, 1999;96(16):9345-50.
Palese et al., Negative-strand RNA viruses: genetic engineering and applications. Proc Nati Acad Sci U S A. Oct. 15, 1996;93(21):11354-8.
Palese P. Genetic engineering of infectious negative-strand RNA viruses. Trends Microbiol. Apr. 1995;3(4):123-5.
Park et al. Engineered viral vaccine constructs with dual specificity: avian influenza and Newcastle disease. Proc Natl Acad Sci U S A. May 23, 2006;103(21):8203-8.
Park et al., 1991, "Rescue of a Foreign Gene by Sendai Virus", Proc. Natl. Acad. Sci. USA 88:5537-5541.
Peeters et al., Generation of a recombinant chimeric Newcastle disease virus vaccine that allows serological differentiation between vaccinated and infected animals. Vaccine. Feb. 8, 2001;19(13-14):1616-27.
Peeters et al., Rescue of Newcastle disease virus from cloned cDNA: evidence that cleavability of the fusion protein is a major determinant for virulence. J Virol. Jun. 1999;73(6):5001-9.
Percy et al., Expression of a foreign protein by influenza A virus. J Virol. Jul. 1994;68(7):4486-92.
Quinn TP and Trevor KT. Rapid quantitation of recombinant retrovirus produced by packaging cell clones. Biotechniques. Dec. 1997;23(6):1038-44.
Racaniello and Baltimore, 1981, "Cloned Poliovirus Complementary DNA is Infectious in Mammalian Cells", Science 214:916-919.
Reimann et al., 1996, "A chimeric simian/human immunodeficiency virus expressing a primary patient human immunodeficiency virus type 1 isolate env causes on AIDS-like disease after in vivo passage in rhesus monkeys", J Virol. 70(10):6922-8.

(56) References Cited

OTHER PUBLICATIONS

Roberts, A and Rose, J., 1998, "Recovery of Negative-Strand RNA Virus from Plasmid DNAs: A Positive Approach Revitalizes a Negative Field", Virology 247:1-6.
Rose JK. Positive strands to the rescue again: a segmented negative-strand RNA virus derived from cloned cDNAs. Proc Natl Acad Sci U S A. Dec. 24, 1996;93(26):14998-5000.
Schickli et al., Plasmid-only rescue of influenza A virus vaccine candidates. Philos Trans R Soc Lond B Biol Sci. Dec. 29, 2001;356(1416):1965-73.
Schlesinger S. RNA viruses as vectors for the expression of heterologous proteins. Mol Biotechnol. Apr. 1995;3(2):155-65.
Schnell et al., 1994, "Infectious Rabies Viruses from Cloned cDNA", EMBO J. 13:4195-4203.
Swayne et al. Recombinant paramyxovirus type I-avian influenza-H7 virus as a vaccine for protection of chickens against influenza and Newcastle disease. Avian Dis. 2003;47(3 Suppl):1047-50.
Szewczyk et al., 1988, "Purification, Thioredoxin Renaturation, and Reconstituted Activity of the Three Subunits of the Influenza A Virus RNA Polymerase", Proc. Natl. Acad. Sci. USA 85:7907-7911.
Taylor et al., 1990, "Newcastle Disease Virus Fusion Protein Expressed in a Fowlpox Virus Recombinant Confers Protection in Chickens", J. Virol. 64:1441-1450.
Tweed et al. Human illness from avian influenza H7N3, British Columbia. Emerg Infect Dis. Dec. 2004; 10(12):2196-9.
Walgate R. H5N1 vaccine strain in a week. The Scientist, Jan. 29, 2004; 5(1)20040129-05.
Ward et al., 1988. "Direct Measurement of the Poliovirus RNA Polymerase Error Frequency in Vitro", J. Virol. 62:558-562.
Yusoff K. et al., 1987, "Nucleotide Sequence Analysis of the L Gene of Newcastle Disease Virus: Homologies with Sendai and Vesicular Stomatitis Viruses" Nucleic Acids Res. 15: 3961-3976.
Zaghouani et al., "Induction of antibodies to the envelope protein of the human immunodeficiency virus by immunization with monoclonal anti-idiotypes.", 1991, Proc. Natl. Acad. Sci. USA 88:5645-6549.
Zaghouani et al., 1992, "Cells Expressing an H Chain Ig Gene Carrying a Viral T Cell Epitope Are Lysed by Specific Cytolytic T Cells", J. Immunol. 148:3604-3609.
Zheng et al. Nonconserved nucleotides at the 3' and 5' ends of an influenza A virus RNA play an important role in viral RNA replication. Virology. Mar. 1, 1996;217(1):242-51.
Zimmer et al., A chimeric respiratory syncytial virus fusion protein functionally replaces the F and HN glycoproteins in recombinant Sendai virus. J Virol. Aug. 2005;79(16):10467-77.
Alexander et al., 1995, "The epidemiology and control of avian influenza and Newcastle disease," Journal of Comparative Pathology, 112: 105-126.
Copeland et al., 2005, "Functional chimeras of human immunodeficiency virus type 1 gp120 and influenza A virus (H3) hemagglutinin," Journal of Virology, 79: 6459-6471.
Di Napoli et al., 2007, "Immunization of primates with a Newcastle disease virus-vectored vaccine via the respiratory tract induces a high titer of serum neutralizing antibodies against highly pathogenic avian influenza virus," *J. Virol*. 2007:11560-11568.
Egorov et al., 1997, "Generation of influenza A transfectant viruses containing deletions of the carboxyl-terminal part of the NS1 protein", in *Emergence and Re-emergence of Negative Strand Viruses, Tenth International Conference on Negative Strand Viruses*. Abstract No. 108, p. 104.
Egorov et al., 1997, "Generation of Influenza A Transfectant Viruses Containing Deletions in the NS1 Protein", Institute of Applied Microbiology, in Emergence and Re-emergence of Negative Strand Viruses, Tenth International Conference on Negative Strand Viruses. Sep. 21-26, Dublin, Ireland. Poster.
Egorov et al., 1998, "Transfectant influenza A viruses with long deletions in the NS1 protein grow efficiently in Vero cells", J Virol., 8: 6437-41.
Gao et al., 2008, "A seven-segmented influenza A virus expressing the influenza C virus glycoprotein HEF," *J. Virol*. 82:6419-6426.
Garcia-Sastre ct al., 1995, "Influenza virus vectors," Biologicals, 23: 171-178.
Krishnamurthy S et al., 2000, "Recovery of a Virulent Strain of Newcastle Disease Virus from Cloned cDNA: Expression of a Foreign Gene Results in Growth Retardation and Attenuation," Virology 278: 168-182.
Li et al., 2005, "Chimeric influenza virus hemagglutinin proteins containing large domains of the *Bacillus anthracis* protective antigen: Protein characterization, incorporation into infectious influenza viruses, and antigenicity," Journal of Virology, 79: 10003-10012.
Luschow et al., 2001, "Protection of chickens from lethal avian influenza A virus infection by live-virus vaccination with infectious laryngotracheitis virus recombinants expressing the hemagglutinin gene," *Vaccine* 19: 4249-4259.
Nayak et al., 2009, "Immunization of chickens with Newcastle disease virus expressing H5 hemagglutinin protects against highly pathogenic H5N1 avian influenza viruses," *PLoS One* 4:e6509.
Roemer-Oberdoerfer et al., 1999, "Generation of recombinant lentogenic Newcastle disease virus from cDNA," Journal of General Virology 80: 2987-2995.
Steel et al., 2008, "A combination in-ovo vaccine for avian influenza virus and Newcastle disease virus," *Vaccine* 26:522-531.
Swayne et al., 2003, "Vaccines for List A poultry diseases: Emphasis on avian influenza," *Development in Biologicals* 114:201-212.
Veits et al., 2006, "Newcastle disease virus expressing H5 hemagglutinin gene protects chickens against Newcastle disease and avian influenza," Proceedings of the National Academy of Sciences of the United States of America 103: 8197-8202.
Watanabe et al., 2003, "Exploitation of nucleic acid packaging signals to generate a novel influenza virus-based vector stably expressing two foreign genes," Journal of Virology, 77: 10575-10583.
Zamarin et al., 2008, "Enhancement of Oncolytic Properties of Genetically-Engineered Fusogenic Newcastle Disease Virus through Antagonism of Cellular Innate Immune Responses," Molecular Therapy 16:S17. Abstract.
European Patent Application No. 10173295.6, Extended European Search Report, dated Oct. 13, 2010.
European Patent Application No. EP 0 683 8693.7, Supplementary European Search Report, dated Mar. 19, 2010.
European Patent Application No. EP 0 683 8693.7, Communication Pursuant to Article 94(3) EPC, dated Jun. 23, 2010.
Tian et al., 2005, "Protective efficacy in chickens, geese and ducks of an H5N1-inactivated vaccine developed by reverse genetics." Virology. 341(1):153-62.
Zamarin et al., 2009, "Enhancement of oncolytic properties of recombinant newcastle disease virus through antagonism of cellular innate immune responses." Mol Ther. 17(4):697-706.
Vigil et al., 2007, "Use of reverse genetics to enhance the oncolytic properties of Newcastle disease virus." Cancer Res. 67(17):8285-92.
Weber et al., 2007, "Viral suppression of the interferon system." Biochimie 89(6-7):836-42.
Deng et al. Localization of a domain on the paramyxovirus attachment protein required for the promotion of cellular fusion by its homologous fusion protein spike. Virology. Jun. 1, 1995;209(2):457-69.
Huang et al. The hemagglutinin-neuraminidase protein of Newcastle disease virus determines tropism and virulence. J Virol. Apr. 2004;78(8):4176-84.

* cited by examiner

FIG. 1

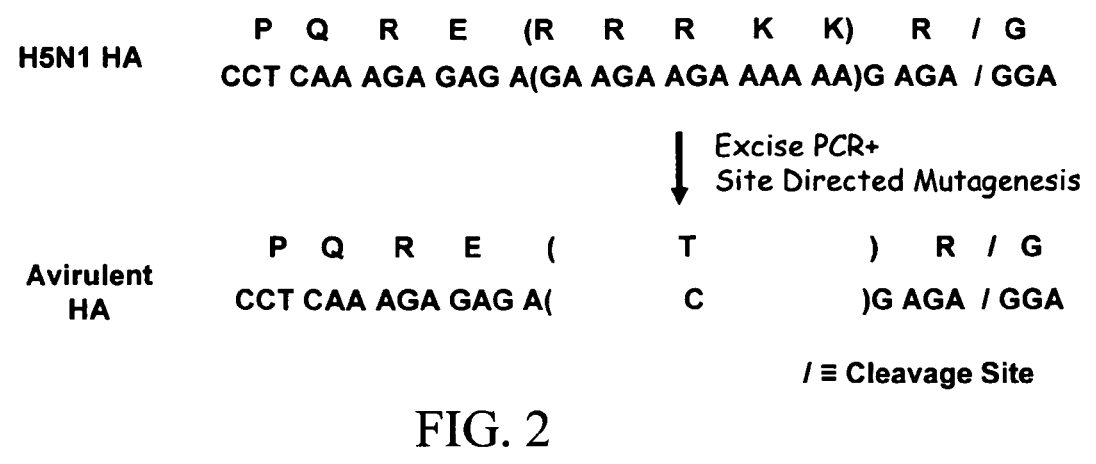

H5N1 HA

P Q R E (R R R K K) R / G

CCT CAA AGA GAG A(GA AGA AGA AAA AA)G AGA / GGA

Excise PCR+
Site Directed Mutagenesis

Avirulent HA

P Q R E ( T ) R / G

CCT CAA AGA GAG A( C )G AGA / GGA

/ ≡ Cleavage Site

FIG. 2

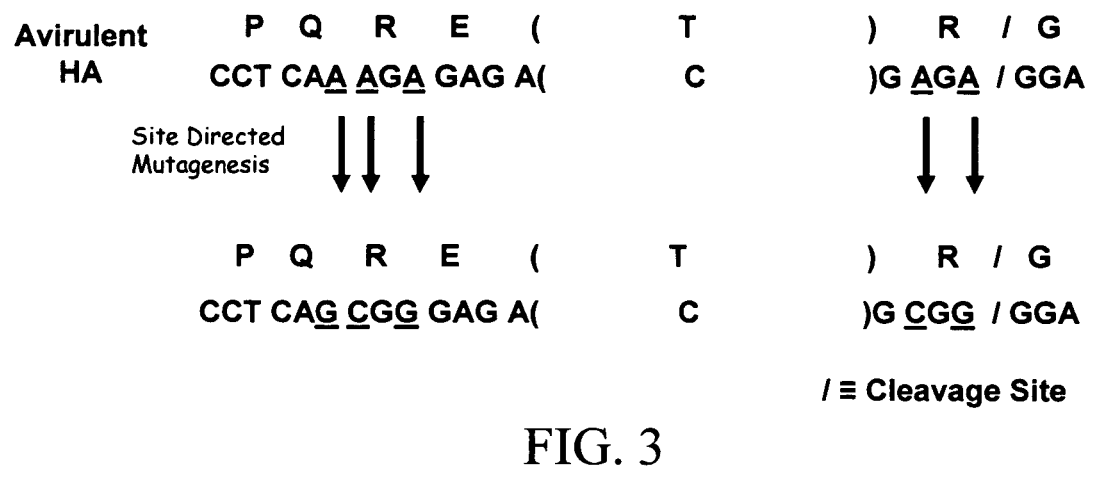

Avirulent HA

P Q R E ( T ) R / G

CCT CAA AGA GAG A( C )G AGA / GGA

Site Directed Mutagenesis

P Q R E ( T ) R / G

CCT CAG CGG GAG A( C )G CGG / GGA

/ ≡ Cleavage Site

FIG. 3

FIG. 4A
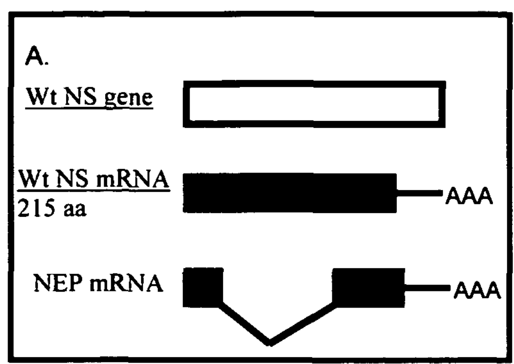
FIG. 4B
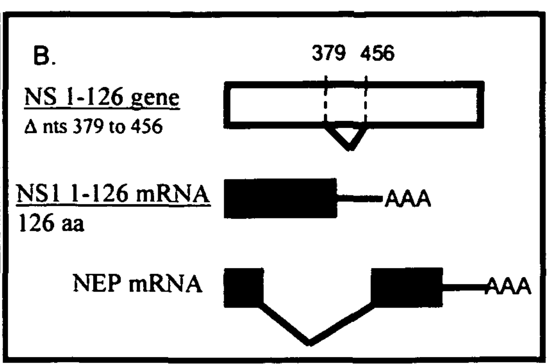
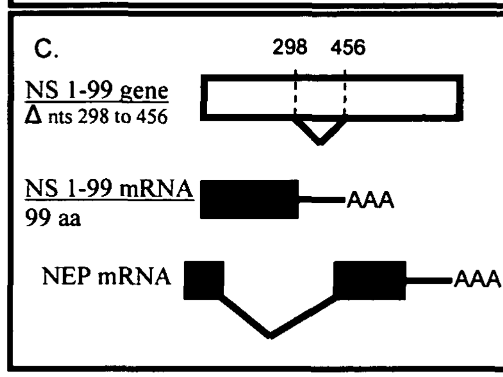
FIG. 4C
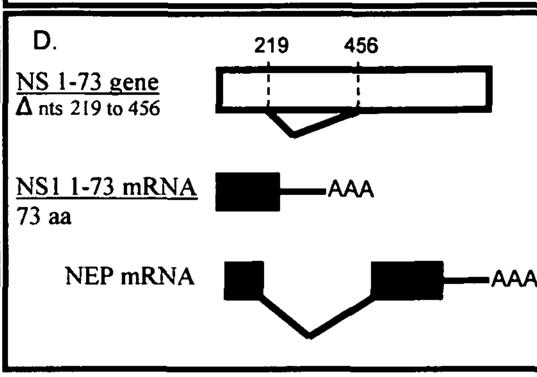
FIG. 4D rNDV/B1-KGFR

3' NP P M F HN L 5'

INSERT

FIG. 5

1 2 3

1: rNDV
2: rNDV-KGFR
3: rNDV-KGFR/F-CT

FIG. 6

1 2

α-avian flu H7

α-NDV

1: rNDV-H7 purified virions

2: rNDV-H7/ F(TM+C) purified virions

αavian H7
αNDV

FIG. 9C

αavian H7
αNDV

FIG. 9D

SEQUENCE LISTING

<160> NUMBER OF SEQ ID NOS: 36

<210> SEQ ID NO 1
<211> LENGTH: 823
<212> TYPE: DNA
<213> ORGANISM: Influenza A virus
<220> FEATURE:
<223> OTHER INFORMATION: Influenza A virus (A/Viet Nam/1203/2004(H5N1)) nonstructural protein 2 (NS) gene

<400> SEQUENCE: 1

```
atggattcca acactgtgtc aagctttcag gtagactgct ttctttggca tgtccgcaaa     60
cgatttgcag accaagaact gggtgatgcc ccattccttg accggcttcg ccgagatcag    120
aagtccctaa gaggaagagg caacactctt ggtctggaca tcgaaacagc tactcgcgca    180
ggaaagcaga tagtggagcg gattctggag ggggagtctg ataaggcact taaaatgccg    240
gcttcacgct acctaactga catgactctc gaagaaatgt caagggactg gttcatgctc    300
atgcccaagc agaaagtggc aggttccctt tgcatcaaaa tggaccaggc aataatggat    360
aaaaccatca tattgaaagc aaacttcagt gtgatttttg accggttgga aaccctaata    420
ctacttagag ctttcacaga agaaggagca atcgtgggag aaatctcacc attaccttct    480
cttccaggac atactggtga ggatgtcaaa aatgcaattg gcgtcctcat cggaggactt    540
gaatggaatg ataacacagt tcgagtcact gaaactatac agagattcgc ttggagaaac    600
agtgatgagg atgggagact tccactccct ccaaatcaga aacggtaaat ggcgagaaca    660
attgagtcag aagtttgaag aaataaggtg gctgattgaa gaagtaagac atagattgaa    720
aattacagaa aacagcttcg aacagataac gtttatgcaa gccttacaac tactgcttga    780
agtggagcaa gagataagag ccttctcgtt tcagcttatt taa                       823
```

<210> SEQ ID NO 2
<211> LENGTH: 982
<212> TYPE: DNA
<213> ORGANISM: Influenza A virus
<220> FEATURE:
<223> OTHER INFORMATION: Influenza A virus (A/Viet Nam/1203/2004(H5N1)) membrane ion channel 2 and matrix protein 1 (M) gene

<400> SEQUENCE: 2

```
atgagtcttc taaccgaggt cgaaacgtac gttctctcta tcatcccgtc aggccccctc     60
aaagccgaga tcgcacagaa acttgaagat gtctttgcag gaaagaacac cgatctcgag    120
gctctcatgg agtggctaaa gacaagacca atcctgtcac ctctgactaa agggattttg    180
ggatttgtat tcacgctcac cgtgcccagt gagcgaggac tgcagcgtag acgctttgtc    240
cagaatgccc taaatggaaa tggagatcca aataatatgg atagggcagt taagctatat    300
aagaagctga aaagagaaat aacattccat ggggctaagg aggtcgcact cagctactca    360
accggtgcac ttgccagttg catgggtctc atatacaaca ggatgggaac ggtgactacg    420
gaagtggctt ttggcctagt gtgtgccact tgtgagcaga ttgcagattc acagcatcgg    480
tctcacagac agatggcaac tatcaccaac ccactaatca gacatgagaa cagaatggtg    540
ctggccagca ctacagctaa ggctatggag cagatggcgg gatcaagtga gcaggcagcg    600
gaagccatgg agatcgctaa tcaggctagg cagatggtgc aggcaatgag gacaattggg    660
actcatccta actctagtgc tggtctgaga gataatcttc ttgaaaattt gcaggcctac    720
cagaaacgaa tgggagtgca gatgcagcga ttcaagtgat cctattgttg ttgccgcaaa    780
```

```
tatcattggg atcttgcact tgatattgtg gattcttgat cgtcttttct tcaaatgcat    840

ttatcgtcgc cttaaatacg gtttgaaaag agggcctgct acggcagggg tacctgagtc    900

tatgagggaa gagtaccggc aggaacagca gagtgctgtg gatgttgacg atggtcattt    960

tgtcaacata gaattggagt aa                                             982


<210> SEQ ID NO 3
<211> LENGTH: 1485
<212> TYPE: DNA
<213> ORGANISM: Influenza A virus
<220> FEATURE:
<223> OTHER INFORMATION: Influenza A virus (A/Viet Nam/1203/2004(H5N1))
      nucleocapsid protein(NP) gene

<400> SEQUENCE: 3

atggcgtctc aaggcaccaa acgatcttat gaacagatgg aaactggtgg ggaacgccag     60

aatgctactg agatcagggc atctgttgga agaatggtta gtggcattgg gaggttctac    120

atacagatgt gcacagaact caaactcagt gactatgaag ggaggctgat ccagaacagc    180

ataacaatag agagaatggt actctctgca tttgatgaaa gaaggaacag atacctggaa    240

gaacacccca gtgcgggaaa ggacccgaag aagactggag gtccaattta tcggaggaga    300

gacgggaaat gggtgagaga gctaattctg tacgacaaag aggagatcag gaggatttgg    360

cgtcaagcga acaatggaga ggacgcaact gctggtctta cccacctgat gatatggcat    420

tccaatctaa atgatgccac atatcagaga acgagagctc tcgtgcgtac tggaatggac    480

ccaaggatgt gctctctgat gcaagggtca actctcccga ggagatctgg agctgccggt    540

gcagcagtaa agggggtagg gacaatggtg atggagctga ttcggatgat aaaacgaggg    600

atcaacgacc ggaatttctg gagaggcgaa aatggaagaa gaacaaggat tgcatatgag    660

agaatgtgca acatcctcaa agggaaattc caaacagcag cacaaagagc aatgatggat    720

caagtgcgag agagcagaaa tcctgggaat gctgaaattg aagatctcat tttctggcca    780

cggtctgcac tcatcctgag aggatcagtg gcccataagt cctgcttgcc tgcttgtgtg    840

tacggacttg cagtggccag tggatatgac tttgagagag aagggtactc tctggttgga    900

atagatcctt tccgcctgct tcaaaacagc caggtcttta gtctcattag accaaatgag    960

aatccagcac ataagagtca attagtgtgg atggcatgcc actctgcagc atttgaggac   1020

cttagagtct caagtttcat cagagggaca agagtggtcc caagaggaca gctatccacc   1080

agaggggttc aaattgcttc aaatgagaac atggaggcaa tggactccaa cactcttgaa   1140

ctgagaagca gatattgggc tataagaacc agaagcggag gaaacaccaa ccagcagagg   1200

gcatctgcag gacagatcag cgttcagccc actttctcgg tccagagaaa ccttcccttc   1260

gaaagagcga ccattatggc agcatttaca ggaaatactg agggcagaac gtctgacatg   1320

aggactgaaa tcataagaat gatggaaagt gccagaccag aagatgtgtc attccagggg   1380

cggggagtct tcgagctctc ggacgaaaag gcaacgaacc cgatcgtgcc ttcctttgac   1440

atgaataatg aaggatctta tttcttcgga gacaatgcag aggag                   1485


<210> SEQ ID NO 4
<211> LENGTH: 1707
<212> TYPE: DNA
<213> ORGANISM: Influenza A virus
<220> FEATURE:
<223> OTHER INFORMATION: Influenza A virus (A/Viet Nam/1203/2004(H5N1))
      hemagglutinin HA  gene

<400> SEQUENCE: 4
```

```
atggagaaaa tagtgcttct ttttgcaata gtcagtcttg ttaaaagtga tcagatttgc     60

attggttacc atgcaaacaa ctcgacagag caggttgaca caataatgga aaagaacgtt    120

actgttacac atgcccaaga catactggaa aagaaacaca acgggaagct ctgcgatcta    180

gatggagtga agcctctaat tttgagagat tgtagcgtag ctggatggct cctcggaaac    240

ccaatgtgtg acgaattcat caatgtgccg gaatggtctt acatagtgga gaaggccaat    300

ccagtcaatg acctctgtta cccaggggat ttcaatgact atgaagaatt gaaacaccta    360

ttgagcagaa taaaccattt tgagaaaatt cagatcatcc ccaaaagttc ttggtccagt    420

catgaagcct cattaggggt gagctcagca tgtccatacc agggaaagtc ctcctttttc    480

agaaatgtgg tatggcttat caaaaagaac agtacatacc caacaataaa gaggagctac    540

aataatacca accaagaaga tcttttggta ctgtggggga ttcaccatcc taatgatgcg    600

gcagagcaga caaagctcta tcaaaaccca accacctata tttccgttgg gacatcaaca    660

ctaaaccaga gattggtacc aagaatagct actagatcca aagtaaacgg gcaaagtgga    720

aggatggagt tcttctggac aattttaaag ccgaatgatg caatcaactt cgagagtaat    780

ggaaatttca ttgctccaga atatgcatac aaaattgtca agaaagggga ctcaacaatt    840

atgaaaagtg aattggaata tggtaactgc aacaccaagt gtcaaactcc aatgggggcg    900

ataaactcta gcatgccatt ccacaatata caccctctca ccattgggga atgccccaaa    960

tatgtgaaat caaacagatt agtccttgcg actgggctca gaaatagccc tcaaagagag   1020

agaagaagaa aaaagagagg attatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactcg   1200

atcattgaca aaatgaacac tcagtttgag gccgttggaa gggaatttaa caacttagaa   1260

aggagaatag agaatttaaa caagaagatg gaagacgggt tcctagatgt ctggacttat   1320

aatgctgaac ttctggttct catggaaaat gagagaactc tagactttca tgactcaaat   1380

gtcaagaacc tttacgacaa ggtccgacta cagcttaggg ataatgcaaa ggagctgggt   1440

aacggttgtt tcgagttcta tcataaatgt gataatgaat gtatggaaag tgtaagaaat   1500

ggaacgtatg actacccgca gtattcagaa gaagcgagac taaaaagaga ggaaataagt   1560

ggagtaaaat tggaatcaat aggaatttac caaatactgt caatttattc tacagtggcg   1620

agttccctag cactggcaat catggtagct ggtctatcct tatggatgtg ctccaatgga   1680

tcgttacaat gcagaatttg catttaa                                      1707
```

```
<210> SEQ ID NO 5
<211> LENGTH: 1350
<212> TYPE: DNA
<213> ORGANISM: Influenza A virus
<220> FEATURE:
<223> OTHER INFORMATION: Influenza A virus (A/Viet Nam/1203/2004(H5N1))
      neuramindase (NA)  gene

<400> SEQUENCE: 5
```

```
atgaatccaa atcagaagat aataaccatc ggatcaatct gtatggtaac tggaatagtt     60

agcttaatgt tacaaattgg gaacatgatc tcaatatggg tcagtcattc aattcacaca    120

gggaatcaac accaatctga accaatcagc aatactaatt ttcttactga gaaagctgtg    180

gcttcagtaa aattagcggg caattcatct ctttgcccca ttaacggatg ggctgtatac    240

agtaaggaca acagtataag gatcggttcc aagggggatg tgtttgttat aagagagccg    300
```

```
ttcatctcat gctcccactt ggaatgcaga actttctttt tgactcaggg agccttgctg    360
aatgacaagc actccaatgg gactgtcaaa gacagaagcc ctcacagaac attaatgagt    420
tgtcctgtgg gtgaggctcc ctccccatat aactcaaggt ttgagtctgt tgcttggtca    480
gcaagtgctt gccatgatgg caccagttgg ttgacgattg gaatttctgg cccagacaat    540
ggggctgtgg ctgtattgaa atacaatggc ataataacag acactatcaa gagttggagg    600
aacaacatac tgagaactca agagtctgaa tgtgcatgtg taaatggctc ttgctttact    660
gtaatgactg acggaccaag taatggtcag gcatcacata agatcttcaa aatggaaaaa    720
gggaaagtgg ttaaatcagt cgaattggat gctcctaatt atcactatga ggaatgctcc    780
tgttatccta atgccggaga aatcacatgt gtgtgcaggg ataattggca tggctcaaat    840
cggccatggg tatctttcaa tcaaaatttg gagtatcaaa taggatatat atgcagtgga    900
gttttcggag acaatccacg ccccaatgat ggaacaggta gttgtggtcc ggtgtcctct    960
aacggggcat atggggtaaa agggttttca tttaaatacg gcaatggtgt ctggatcggg   1020
agaaccaaaa gcactaattc caggagcggc tttgaaatga tttgggatcc aaatgggtgg   1080
actgaaacgg acagtagctt ttcagtgaaa caagatatcg tagcaataac tgattggtca   1140
ggatatagcg ggagttttgt ccagcatcca gaactgacag gactagattg cataagacct   1200
tgtttctggg ttgagttgat cagagggcgg cccaaagaga gcacaatttg gactagtggg   1260
agcagcatat ctttttgtgg tgtaaatagt gacactgtgg gttggtcttg gccagacggt   1320
gctgagttgc cattcaccat tgacaagtag                                     1350
```

<210> SEQ ID NO 6
<211> LENGTH: 2151
<212> TYPE: DNA
<213> ORGANISM: Influenza A virus
<220> FEATURE:
<223> OTHER INFORMATION: Influenza A virus (A/Viet Nam/1203/2004(H5N1)) polymerase protein PA gene

<400> SEQUENCE: 6

```
atggaagact ttgtgcgaca atgcttcaat ccaatgattg tcgagcttgc ggaaaaggca     60
atgaaagaat atggggaaga tccgaaaatc gaaacgaaca agtttgctgc aatatgcaca    120
cacttggagg tctgtttcat gtattcggat tttcacttta ttgatgaacg gagtgaatca    180
ataattgtag aatctggaga tccgaatgca ttattgaaac accgatttga aataattgaa    240
ggaagagacc gaacgatggc ctggactgtg gtgaatagta tctgcaacac cacaggagtt    300
gagaaaccta aatttctccc agatttgtat gactacaaag agaaccgatt catcgaaatt    360
ggagtgacac ggagggaagt tcatacatac tatctggaga aagccaacaa gataaaatcc    420
gaggagacac atattcacat attctcattc acaggggagg aaatggccac caaagcggac    480
tacacccttg atgaagagag cagggcaaga attaaaacca ggctgttcac cataaggcag    540
gaaatggcca gtaggggtct atgggattcc tttcgtcaat ccgagagagg cgaagagaca    600
attgaagaaa aatttgaaat cactggaacc atgcgcagac ttgcagacca aagtctccca    660
ccgaacttct ccagccttga aaactttaga gcctatgtgg atggattcga accgaacggc    720
tgcattgagg gcaagctttc tcaaatgtca aaagaagtga atgctagaat tgagccattt    780
ttgaagacaa cgccacgccc tctcagacta cctgatgggc ctccttgctc tcagcggtcg    840
aagttcttgc tgatggatgc ccttaaatta agcatcgaag acccgagtca tgagggggag    900
gggataccac tatacgatgc aatcaaatgc atgaagacat tttcggctg gaaagagccc    960
```

```
aacatcgtga aaccacatga aaaaggtata aaccccaatt acctcctggc ttggaagcaa   1020

gtgctggcag aactccaaga tattgaaaat gaggagaaaa tcccaaaaac aaagaacatg   1080

aaaaaaacaa gccagttgaa gtgggcactc ggtgagaaca tggcaccaga gaaagtagac   1140

tttgaggact gcaaagatgt tagcgatcta agacagtatg acagtgatga accagagtct   1200

agatcactag caagctggat tcagagtgaa ttcaacaagg catgtgaatt gacagattcg   1260

atttggattg aactcgatga aataggagaa gacgtagctc caattgagca cattgcaagt   1320

atgagaagga actattttac agcggaagta tcccattgca gggccactga atacataatg   1380

aagggagtgt acataaacac agccctgttg aatgcatcct gtgcagccat ggatgacttt   1440

caactgattc caatgataag caaatgcaga accaaagaag gaagacggaa aactaatctg   1500

tatggattca ttataaaagg gagatcccac ttgaggaatg ataccgatgt ggtaaatttt   1560

gtgagtatgg aattctctct tactgatccg aggctggagc cacacaagtg ggaaaagtac   1620

tgtgtcctcg agataggaga catgctcctc cggactgcag taggccaagt ttcgaggccc   1680

atgttcctgt atgtaagaac caatggaacc tccaagatca aaatgaaatg gggcatggaa   1740

atgaggcgat gccttcttca atcccttcaa caaattgaaa gcatgattga agccgagtct   1800

tctgtcaaag agaaggacat gaccaaagaa ttctttgaaa acaaatcaga aacatggccg   1860

attggagagt cccccaaggg agtggaggaa ggctccatcg gaaaggtgtg cagaaccttg   1920

ctggcgaagt ctgtgttcaa cagtttatat gcatctccac aactcgaggg gttttcagct   1980

gaatcaagaa aattgcttct cattgctcag gcacttaggg acaacctgga acctgggacc   2040

ttcgatcttg gagggctata tgaagcaatt gaggagtgcc tgattaacga tccctgggtt   2100

ttgcttaatg cgtcttggtt caactccttc ctcgcacatg cactgaaata g            2151
```

```
<210> SEQ ID NO 7
<211> LENGTH: 2274
<212> TYPE: DNA
<213> ORGANISM: Influenza A virus
<220> FEATURE:
<223> OTHER INFORMATION: Influenza A virus (A/Viet Nam/1203/2004(H5N1))
      polymerase protein PB1 gene

<400> SEQUENCE: 7
```

```
atggatgtca atccgacttt acttttcttg aaagtaccag tgcaaaatgc tataagtacc     60

accttccctt atactggaga ccctccatac agccatggaa cagggacagg atacaccatg    120

gacacagtca acagaacaca ccaatattca gaaaagggga agtggacaac aaacacagag    180

actggagcac cccaactcaa cccgattgat ggaccactac ctgaggataa tgagcccagt    240

gggtacgcac aaacagattg tgtattggaa gcaatggctt tccttgaaga atcccaccca    300

gggatctttg aaaactcgtg tcttgaaacg atggaaattg ttcaacaaac aagagtggat    360

aaactgaccc aaggtcgcca gacctatgac tggacattga atagaaacca accggctgca    420

actgctttgg ccaacactat agaaatcttc agatcgaacg gtctaacagc caatgaatcg    480

ggacggctaa tagatttcct caaggatgtg atggagtcaa tggataagga agaaatggag    540

ataacaacac atttccagag aaagagaagg gtgagggaca acatgaccaa gaaaatggtc    600

acacaaagaa caatagggaa gaaaaaacaa aggctgaaca aaaagagcta cctgataaga    660

gcactgacac tgaacacaat gacaaaagat gcagaaagag gcaaattgaa gaggcgagcg    720

attgcaacac ccggaatgca aatcagagga ttcgtgtact ttgttgaaac actagcgagg    780

agtatctgtg agaaacttga gcaatctgga ctcccagtcg gagggaatga gaagaaggct    840
```

aaattggcaa acgtcgtgag gaagatgatg actaactcac aagatactga actctccttt 900
acaattactg gagacaatac caaatggaat gagaatcaga atcctaggat gtttctggca 960
atgataacgt acatcacaag gaaccagcca gaatggtttc ggaatgtctt aagcatagct 1020
cctataatgt tctcaaacaa aatggcgaga ctaggaaaag gatacatgtt cgaaagtaag 1080
agcatgaagt tacgaacaca aataccagca gaaatgcttg caaacattga tcttaaatac 1140
ttcaatgaat taacgaaaaa gaaaattgag aaaataaggc ctctattaat agatggtaca 1200
gcctcattga gccctggaat gatgatgggc atgttcaaca tgctgagtac agtcctagga 1260
gtttcaatcc tgaatcttgg acagaaaagg tacaccaaaa ccacatattg gtgggacgga 1320
ctccaatcct ctgatgattt cgctctcatc gtaaatgcac cgaatcatga gggaatacaa 1380
gcaggagtgg ataggtttta taggacttgt aaactagttg gaatcaatat gagcaagaag 1440
aagtcttaca taaatcggac agggacattt gaattcacga gctttttcta ccgctatgga 1500
tttgtagcca atttcagtat ggagctgccc agttttggag tgtctggaat taatgaatcg 1560
gccgacatga gcattggtgt tacagtgata aaaaacaata tgataaacaa cgaccttggg 1620
ccagcaacag ctcagatggc tcttcagtta ttcatcaagg actacagata cacataccga 1680
tgccacagag ggatacgca aatccaaaca aggagatcat tcgagctgaa gaagctgtgg 1740
gagcaaaccc gttcaaaggc aggactgttg gtttcagatg gaggaccaaa tctatacaat 1800
atccgaaacc tccatattcc tgaagtctgc ttaaaatggg aattgatgga tgaagattac 1860
cagggcagac tgtgtaatcc tctgaatcca ttcgtcagcc ataaggaaat tgaatctgtc 1920
aacaatgctg tagtaatgcc agctcatggc ccggccaaga gtatggaata tgatgccgtt 1980
gcaactacac attcatggat tcctaaaagg aaccgttcca ttctcaatac gagtcaaagg 2040
ggaattcttg aggatgaaca gatgtaccag aagtgctgca atctattcga gaaattcttc 2100
cccagcagtt catatcggag gccagttgga atttccagca tggtggaggc catggtgtct 2160
agggcccgaa ttgacgcacg aatcgatttc gagtctggaa ggattaagaa agaagagttt 2220
gccgagatca tgaagatctg ttccaccatt gaagaactca gacggcaaaa atag 2274

<210> SEQ ID NO 8
<211> LENGTH: 2280
<212> TYPE: DNA
<213> ORGANISM: Influenza A virus
<220> FEATURE:
<223> OTHER INFORMATION: Influenza A virus (A/Viet Nam/1203/2004(H5N1)) polymerase basic subunit 2 (PB2) gene

<400> SEQUENCE: 8
atggagagaa taaaagaatt acgagatcta atgtcacagt cccgcactcg cgagatacta 60
acaaaaacca ctgtggacca tatggccata atcaagaaat acacatcagg aagacaagag 120
aagaaccctg ctctcagaat gaaatggatg atggcaatga aatatccaat cacagcggac 180
aagagaataa tagagatgat tcctgaaagg aatgaacaag ggcagacgct ctggagcaag 240
acaaatgatg ctggatcgga cagggtgatg gtgtctcccc tagctgtaac ttggtggaat 300
aggaatgggc cggcgacaag tgcagttcat tatccaaagg tttacaaaac atactttgag 360
aaggttgaaa gattaaaaca tggaaccttc ggtcccgttc atttccgaaa ccaggttaaa 420
atacgccgcc gagttgatat aaatcctggc catgcagatc tcagtgctaa agaagcacaa 480
gatgtcatca tggaggtcgt tttcccaaat gaagtgggag ctagaatatt gacatcagag 540
tcgcaattga caataacgaa agagaagaaa gaagagctcc aagattgtaa gattgctccc 600

```
ttaatggttg catacatgtt ggaaagggaa ctggtccgca aaaccagatt cctaccggta    660

gcaggcggaa caagtagtgt gtacattgag gtattgcatt tgactcaagg gacctgctgg    720

gaacagatgt acactccagg cggagaagtg agaaatgacg atgttgacca gagtttgatc    780

attgctgcca gaaacattgt taggagagca acagtatcag cggatccact ggcatcactg    840

ctggagatgt gtcacagcac acaaattggt gggataagga tggtggacat ccttaggcaa    900

aatccaactg aggaacaagc tgtggatata tgcaaagcag caatgggtct taggatcagt    960

tcttccttta gctttggagg cttcactttc aaaagaacaa gtggatcatc cgtcaagaag   1020

gaagaggaag tgcttacagg caacctccaa acattgaaaa taagagtaca tgaggggtat   1080

gaggaattca caatggttgg gcggagggca acagctatcc tgaggaaagc aactagaagg   1140

ctgattcagt tgatagtaag tggaagagac caacaatcaa tcgctgaggc aatcattgta   1200

gcaatggtgt tctcacagga ggattgcatg ataaaggcag tccgaggcga tctgaatttc   1260

gtaaacagag caaaccaaag attaaacccc atgcatcaac tcctgagaca ttttcaaaag   1320

gacgcaaaag tgctatttca gaattgggga attgaaccca ttgataatgt catggggatg   1380

atcggaatat tacctgacat gactcccagc acagaaatgt cactgagagg agtaagagtt   1440

agtaaaatgg gagtggatga atattccagc actgagagag tagttgtaag tattgaccgt   1500

ttcttaaggg ttcgagatca gcgggggaac gtactcttat ctcccgaaga ggtcagcgaa   1560

acccagggaa cagagaaatt gacaataaca tattcatcat caatgatgtg ggaaatcaac   1620

ggtcctgagt cagtgcttgt taacacctat cagtggatca tcagaaactg ggagactgtg   1680

aagattcaat ggtctcaaga ccccacgatg ctgtacaata agatggagtt tgaaccgttc   1740

caatccttgg tacccaaagc tgccagaggt caatacagtg gatttgtgag aacattattc   1800

cagcaaatgc gtgacgtact ggggacattt gatactgtcc agataataaa gctgctacca   1860

tttgcagcag ccccaccgaa gcagagcaga atgcagtttt cttctctaac tgtgaatgtg   1920

agaggctcag gaatgagaat actcgtaagg ggcaattccc ctgtgttcaa ctacaataag   1980

gcaaccaaaa ggcttaccgt ccttggaaag gacgcaggtg cattaacaga ggatccggat   2040

gaagggacag ccggagtgga gtctgcagta ctgaggggat tcttaatttt aggcaaggag   2100

gacaaaaggt atggaccagc attgagcatc aatgaactga gcaatcttgc gaagggggag   2160

aaagctaatg tgctgatagg gcaaggagac gtggtgttgg taatgaaacg aaaacgggac   2220

tctagcatac ttactgacag ccagacagcg accaaaagaa ttcggatggc catcaattag   2280
```

```
<210> SEQ ID NO 9
<211> LENGTH: 1409
<212> TYPE: DNA
<213> ORGANISM: Influenza A virus
<220> FEATURE:
<223> OTHER INFORMATION: Influenza A virus (A/WSN/1933(H1N1))
      neuraminidase gene

<400> SEQUENCE: 9

agcgaaagca ggagtttaaa tgaatccaaa ccagaaaata ataaccattg ggtcaatctg     60

tatggtagtc ggaataatta gcctaatatt gcaaatagga aatataatct caatatggat    120

tagccattca attcaaaccg gaaatcaaaa ccatactgga atatgcaacc aaggcagcat    180

tacctataaa gttgttgctg ggcaggactc aacttcagtg atattaaccg gcaattcatc    240

tctttgtccc atccgtgggt gggctataca cagcaaagac aatggcataa gaattggttc    300

caaaggagac gtttttgtca taagagagcc ttttatttca tgttctcact tggaatgcag    360
```

```
gaccttttttt ctgactcaag gcgccttact gaatgacaag cattcaaggg ggacctttaa    420

ggacagaagc ccttataggg ccttaatgag ctgccctgtc ggtgaagctc cgtccccgta    480

caattcaagg tttgaatcgg ttgcttggtc agcaagtgca tgtcatgatg gaatgggctg    540

gctaacaatc ggaatttctg gtccagatga tggagcagtg gctgtattaa aatacaacgg    600

cataataact gaaaccataa aaagttggag gaagaatata ttgagaacac aagagtctga    660

atgtacctgt gtaaatggtt catgttttac cataatgacc gatggcccaa gtgatgggct    720

ggcctcgtac aaaatttca agatcgagaa ggggaaggtt actaaatcaa tagagttgaa    780

tgcacctaat tctcactacg aggaatgttc ctgttaccct gataccggca aagtgatgtg    840

tgtgtgcaga gacaattggc acggttcgaa ccgaccatgg gtgtccttcg accaaaacct    900

agattataaa ataggataca tctgcagtgg ggttttcggt gacaacccgc gtcccaaaga    960

tggaacaggc agctgtggcc cagtgtctgc tgatggagca aacggagtaa agggattttc   1020

atataagtat ggcaatggtg tttggatagg aaggactaaa agtgacagtt ccagacatgg   1080

gtttgagatg atttgggatc ctaatggatg gacagagact gatagtaggt tctctatgag   1140

acaagatgtt gtggcaatga ctgatcggtc agggtacagc ggaagtttcg ttcaacatcc   1200

tgagctaaca gggctagact gtatgaggcc ttgcttctgg gttgaattaa tcaggggggct   1260

acctgaggag gacgcaatct ggactagtgg gagcatcatt tctttttgtg gtgtgaatgg   1320

tgatactgta gattggtctt ggccagacgg tgctgagttg ccgttcacca ttgacaagta   1380

gtttgttcaa aaaactcctt gtttctact                                  1409
```

<210> SEQ ID NO 10
<211> LENGTH: 15186
<212> TYPE: DNA
<213> ORGANISM: Newcastle disease virus
<220> FEATURE:
<223> OTHER INFORMATION: Newcastle disease virus B1 genome

<400> SEQUENCE: 10

```
accaaacaga gaatcggtga gttacgataa aaggcgaagg agcaattgaa gtcgcacggg     60

tagaaggtgt gaatctcgag tgcgagcccg aagcacaaac tcgaggaagc cttctgccaa    120

catgtcttcc gtattcgacg agtacgaaca gctcctcgcg gctcagactc gccccaatgg    180

agctcatgga gggggggaga aagggagtac cttaaaagta gacgtcccgg tattcactct    240

taacagtgat gacccagaag ataggtggag ctttgtggta ttctgcctcc ggattgctgt    300

tagcgaagat gccaacaaac cactcaggca aggtgctctc atatctcttt tatgctccca    360

ctcacaggta atgaggaacc atgttgccct tgcagggaaa cagaatgaag ccacattggc    420

cgtgcttgag attgatggct ttgccaacgg cacgccccag ttcaacaata ggagtggagt    480

gtctgaagag agagcacaga gatttgcgat gatagcagga tctctccctc gggcatgcag    540

caacggcacc ccgttcgtca cagccggggc tgaagatgat gcaccagaag acatcaccga    600

taccctggag aggatcctct ctatccaggc tcaagtatgg gtcacagtag caaaagccat    660

gactgcgtat gagactgcag atgagtcgga aacaaggcga atcaataagt atatgcagca    720

aggcagggtc caaaagaaat acatcctcta ccccgtatgc aggagcacaa tccaactcac    780

gatcagacag tctcttgcag tccgcatctt tttggttagc gagctcaaga gaggccgcaa    840

cacggcaggt ggtacctcta cttattataa cctagtaggg gacgtagact catatatcag    900

gaataccggg cttactgcat tcttcttgac actcaagtac ggaatcaaca ccaagacatc    960
```

```
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccaaggac tttatgagca catcattctg   1200
gagacttgga gtagagtacg ctcaggctca gggaagtagc attaacgagg atatggctgc   1260
cgagctaaag ctaaccccgg cagcaaggag ggcctggca gctgctgccc aacgagtctc    1320
cgaggtgacc agcagcatag acatgcctac tcaacaagtc ggagtcctca ctgggcttag   1380
cgagggggga tcccaagccc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg attgacaaaa cccagcctgc ttctacaaga   1620
acatcccaat gctctcaccc gtagtcgacc cctcgatttg cggctctata tgaccacacc   1680
ctcaaacaaa catccccctc tttcctccct cccccctgctg tacaactccg cacgccctag   1740
gcaacagagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgctgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catggtctcc gatcaaagca gagccaaaac aatacccctg   2520
tttctgcgga tcatttccac ccacctgtag actttgtgca agcgatgatg tctattatgg   2580
aggggatttc ccaaagagta agtaaggttg cctatcaggt agatcttgtt tttaaacaga   2640
catcctccat ccctatgatg ggtccgaaa tccaacagct gaaaacattt gttgcagtca    2700
tggaagccaa cttgggaatg atgaagattt tggatcccgg ttgtgccaac atttcatctt   2760
tgagtgatct acgggcagtt gcccgatctc acccggtttt agtttcaggc cctggagacc   2820
catctcccta tgtgatacaa ggaggcgaaa tggcacttaa taaactttcg caaccagtgc   2880
cacatccatc tgaattgatt aaacccgcca ctgcatgcgg gcctgatata ggagtggaga   2940
gggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc cccgcagac ccaaggtcca actctccaag cggcaatcct    3180
ctctcgcttc ctcagcccca ctgaatgatc gcgcaaccgc aattaatcta gctacattaa   3240
ggattaagaa aaaatacggg tagaattgga gtgccccaat tgtgccaaga tggactcatc   3300
taggacaatt gggctgtact ttgattctgc ccattcttct agcaacctgt tagcatttcc   3360
```

```
gatcgtccta caagacacag gagatgggaa gaagcaaatc gccccgcaat ataggatcca   3420
gcgccttgac ttgtggactg atagtaagga agactcagta ttcatcacca cctatggatt   3480
catctttcaa gttgggaatg aagaagccac tgtcggcatt atcgatgata aacccaagcg   3540
cgagttactt tccgctgcga tgctctgcct aggaagcgtc ccaaataccg gagaccttat   3600
tgagctggca agggcctgtc tcactatgat ggtcacatgc aagaagagtg caactaatac   3660
tgagagaatg gttttctcag tagtgcaggc accccaagtg ctgcaaagct gtagggttgt   3720
ggcaaacaaa tactcatcag tgaatgcagt caagcacgtg aaagcgccag agaagatccc   3780
cgggagtgga accctagaat acaaggtgaa ctttgtctcc ttgactgtgg taccgaagaa   3840
ggatgtctac aagatcccag ctgcagtatt gaagatttct ggctcgagtc tgtacaatct   3900
tgcgctcaat gtcactatta atgtggaggt agacccgagg agtcctttgg ttaaatctct   3960
gtctaagtct gacagcggat actatgctaa cctcttcttg catattggac ttatgaccac   4020
cgtagatagg aaggggaaga aagtgacatt tgacaagctg gaaaagaaaa taaggagcct   4080
tgatctatct gtcgggctca gtgatgtgct cgggccttcc gtgttggtaa aagcaagagg   4140
tgcacggact aagcttttgg cacctttctt ctctagcagt gggacagcct gctatcccat   4200
agcaaatgct tctcctcagg tggccaagat actctggagt caaaccgcgt gcctgcggag   4260
cgttaaaatc attatccaag caggtaccca acgcgctgtc gcagtgaccg ctgaccacga   4320
ggttacctct actaagctgg agaaggggca cacccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtcc atcaagttag aaaaaacacg   4500
ggtagaagac tctggatccc ggttggcgcc ctccaggtgc aggatgggct ccagaccttt   4560
taccaagaac ccagcaccta tgatgctgac tatccgggtc gcgctggtat tgagttgcat   4620
ctgtccggca aactccattg atggcaggcc ttttgcagct gcaggaattg tggttacagg   4680
agacaaagca gtcaacatat acacctcatc ccagacagga tcaatcatag ttaagctcct   4740
cccgaatctg cccaaggata aggaggcatg tgcgaaagcc cccttggatg catacaacag   4800
gacattgacc actttgctca cccccctgg tgactctatc cgtaggatac aagagtctgt   4860
gactacatct ggaggggga gacaggggcg ccttataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cccaactagc agtggcagtt gggaagatgc agcagtttgt   5100
taatgaccaa tttaataaaa cagctcagga attagactgc ataaaaattg cacagcaagt   5160
tggtgtagag ctcaacctgt acctaaccga attgactaca gtattcggac cacaaatcac   5220
ttcacctgcc ttaaacaagc tgactattca ggcactttac aatctagctg gtgggaatat   5280
ggattactta ttgactaagt taggtatagg gaacaatcaa ctcagctcat taatcggtag   5340
cggcttaatc accggtaacc ctattctata cgactcacag actcaactct tgggtataca   5400
ggtaactcta ccttcagtcg ggaacctaaa taatatgcgt gccacctact tggaaacctt   5460
atccgtaagc acaaccaggg gatttgcctc ggcacttgtc ccaaaagtgg tgacacaggt   5520
cggttctgtg atagaagaac ttgacacctc atactgtata gaaactgact tagatttata   5580
ttgtacaaga atagtaacgt tccctatgtc ccctggtatt tactcctgct tgagcggcaa   5640
tacatcggcc tgtatgtact caaagaccga aggcgcactt actacaccat atatgactat   5700
```

```
caaaggctca gtcatcgcta actgcaagat gacaacatgt agatgtgtaa accccccggg   5760
tatcatatcg caaaactatg gagaagccgt gtctctaata gataaacaat catgcaatgt   5820
tttatcctta ggcgggataa ctttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
aaaactagac aaagtcaatg tcaaactgac cagcacatct gctctcatta cctatatcgt   6060
tttgactatc atatctcttg tttttggtat acttagcctg attctagcat gctacctaat   6120
gtacaagcaa aaggcgcaac aaaagacctt attatggctt gggaataata ccctagatca   6180
gatgagagcc actacaaaaa tgtgaacaca gatgaggaac gaaggtttcc ctaatagtaa   6240
tttgtgtgaa agttctggta gtctgtcagt tcggagagtt aagaaaaaac taccggttgt   6300
agatgaccaa aggacgatat acgggtagaa cggtaagaga ggccgcccct caattgcgag   6360
ccagacttca caacctccgt tctaccgctt caccgacaac agtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatgggggc tagcacacct agcgatcttg taggcatacc gactaggatt   6600
tccagggcag aagaaaagat tacatctaca cttggttcca atcaagatgt agtagatagg   6660
atatataagc aagtggccct tgagtctcca ttggcattgt taaatactga gaccacaatt   6720
atgaacgcaa taacatctct ctcttatcag attaatggag ctgcaaacaa cagcgggtgg   6780
ggggcaccta ttcatgaccc agattatata ggggggatag gcaaagaact cattgtagat   6840
gatgctagtg atgtcacatc attctatccc tctgcatttc aagaacatct gaattttatc   6900
ccggcgccta ctacaggatc aggttgcact cgaataccct catttgacat gagtgctacc   6960
cattactgct acacccataa tgtaatattg tctggatgca gagatcactc acactcatat   7020
cagtatttag cacttggtgt gctccggaca tctgcaacag ggagggtatt cttttctact   7080
ctgcgttcca tcaacctgga cgacacccaa aatcggaagt cttgcagtgt gagtgcaact   7140
cccctgggtt gtgatatgct gtgctcgaaa gccacggaga cagaggaaga agattataac   7200
tcagctgtcc ctacgcggat ggtacatggg aggttagggt tcgacggcca atatcacgaa   7260
aaggacctag atgtcacaac attattcggg gactgggtgg ccaactaccc aggagtaggg   7320
ggtggatctt ttattgacag ccgcgtatgg ttctcagtct acggagggtt aaaacccaat   7380
tcacccagtg acactgtaca ggaagggaaa tatgtgatat acaagcgata caatgacaca   7440
tgcccagatg agcaagacta ccagattcga atggccaagt cttcgtataa gcctggacgg   7500
tttggtggga aacgcataca gcaggctatc ttatctatca aagtgtcaac atccttaggc   7560
gaagacccgg tactgactgt accgcccaac acagtcacac tcatgggggc cgaaggcaga   7620
attctcacag tagggacatc ccatttcttg tatcagcgag ggtcatcata cttctctccc   7680
gcgttattat atcctatgac agtcagcaac aaaacagcca ctcttcatag tccttataca   7740
ttcaatgcct tcactcggcc aggtagtatc ccttgccagg cttcagcaag atgccccaac   7800
tcgtgtgtta ctggagtcta tacagatcca tatcccctaa tcttctatag aaaccacacc   7860
ttgcgagggg tattcgggac aatgcttgat ggtgaacaag caagacttaa ccctgcgtct   7920
gcagtattcg atagcacatc ccgcagtcgc ataactcgag tgagttcaag cagcatcaaa   7980
gcagcataca caacatcaac ttgttttaaa gtggtcaaga ccaataagac ctattgtctc   8040
agcattgctg aaatatctaa tactctcttc ggagaattca gaatcgtccc gttactagtt   8100
```

```
gagatcctca aagatgacgg ggttagagaa gccaggtctg gctagttgag tcaactatga   8160
aagagttgga aagatggcat tgtatcacct atcttctgcg acatcaagaa tcaaaccgaa   8220
tgccggcgcg tgctcgaatt ccatgtcgcc agttgaccac aatcagccag tgctcatgcg   8280
atcagattaa gccttgtcaa tagtctcttg attaagaaaa aatgtaagtg gcaatgagat   8340
acaaggcaaa acagctcatg gtaaataata cgggtaggac atggcgagct ccggtcctga   8400
aagggcagag catcagatta tcctaccaga gtcacacctg tcttcaccat tggtcaagca   8460
caaactactc tattattgga aattaactgg gctaccgctt cctgatgaat gtgacttcga   8520
ccacctcatt ctcagccgac aatggaaaaa aatacttgaa tcggcctctc ctgatactga   8580
gagaatgata aaactcggaa gggcagtaca ccaaactctt aaccacaatt ccagaataac   8640
cggagtactc caccccaggt gtttagaaga actggctaat attgaggtcc ctgattcaac   8700
caacaaattt cggaagattg agaagaagat ccaaattcac aacacgagat atggagaact   8760
gttcacaagg ctgtgtacgc atatagagaa gaaactgctg gggtcatctt ggtctaacaa   8820
tgtcccccgg tcagaggagt tcagcagcat tcgtacggat ccggcattct ggtttcactc   8880
aaaatggtcc acagccaagt ttgcatggct ccatataaaa cagatccaga ggcatctgat   8940
tgtggcagct aggacaaggt ctgcggccaa caaattggtg atgctaaccc ataaggtagg   9000
ccaagtcttt gtcactcctg aacttgttgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
gggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgcctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacggat acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atacgaccct gtcactaacc tgagcatgtt   9780
cctaaaagac aaggcaatcg cacaccccaa cgataattgg cttgcctcgt ttaggcggaa   9840
ccttctctcc gaagaccaga agaaacatgt aaaggaagcg acttcgacta accgcctctt   9900
gatagagttt ttagagtcaa atgattttga tccatataaa gagatggaat atctgacgac   9960
ccttgagtac cttagagatg acaatgtggc agtatcatac tcgctcaaag agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacga tcaaattgtt cgctcatgcc atcaatcagt tgatgggcct  10380
acctcatttc ttcgagtgga ttcacctaag actgatggac actacgatgt tcgtaggaga  10440
```

```
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag atgactctcc  10680
ggagatggtg ttgacacagt tgcatcaagc cagtgataat ttcttcaagg aattaatcca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa aacaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg caccccgatc ttaatcagtc gtggattgag gacatctctt ttgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggacta ctgagtccta acattatgac taatatctta actaggccgc ctgggaatgg  11280
agattgggcc agtctgtgca acgacccata ctctttcaat tttgagactg ttgcaagccc  11340
aaatattgtt cttaagaaac atacgcaaag agtcctattt gaaacttgtt caaatccctt  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacactgtaa ttaagattgc  11580
gcttactagg aggccattag gcatcaagag gctgatgcgg atagtcaatt attctagcat  11640
gcatgcaatg ctgtttagag acgatgtttt ttcctctagt agatccaacc acccccttagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
gggtgagatt cttagtgtaa gcggagggtg tacaagatgt gacagcggag atgaacaatt  11880
tacttggttc catcttccaa gcaatataga attgaccgat gacaccagca agaatcctcc  11940
gatgagggta ccatatctcg ggtcaaagac acaggagagg agagctgcct cacttgcgaa  12000
aatagctcat atgtcgccac atgtgaaggc tgccctaagg gcatcatccg tgttgatctg  12060
ggcttatggg gataatgaag taaattggac tgctgctctc acgattgcaa aatctcggtg  12120
taatgtaaac ttagagtatc ttcggttact gtccccttta cccacggctg ggaatcttca  12180
acatagacta gatgatggta taactcagat gacattcacc cctgcatctc tctacaggtg  12240
tcaccttaca ttcacatatc caatgattct caaaggctgt tcactgaaga aggagtcaaa  12300
gaggggaatg tggtttacca acagagtcat gctcttgggt ttatctctaa tcgaatcgat  12360
ctttccaatg acaacaacca gaacatatga tgagatcaca ctgcacctac atagtaaatt  12420
tagttgctgt atcagggaag cacctgttgc ggttcctttc gagctacttg gggtggcacc  12480
ggaactgagg acagtgacct caaataagtt tatgtatgat cctagccctg tatcggaggg  12540
agactttgcg agacttgact tagctatctt caagagttat gagcttaatc tggagtcata  12600
tcccacgata gagctaatga acattctttc aatatccagc gggaagttga ttggccagtc  12660
tgtggtttct tatgatgaag atacctccat aaagaatgat gccataatag tgtatgacaa  12720
tacccgaaat tggatcagtg aagctcagaa ttcagatgtg gtccgcctat ttgaatatgc  12780
agcacttgaa gtgctcctcc accgttctta ccaactctat tacctgagag taagaggcct  12840
```

```
agacaatatt gtcttatata tgggtgattt atacaagaat atgccaggaa ttctactttc  12900
caacattgca gctacaatat ctcatcctgt cattcattca aggttacatg cagtgggcct  12960
ggtcaaccat gacggatcac accaacttgc agatacggat tttatcgaaa tgtctgcaaa  13020
actgttagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380
cagggatact atcctggcgt tgttgttccc ccaagagcca ttattagagt tcccttctgt  13440
gcaagatatt ggtgctcgag tgaaagatcc attcacccga caacctgcgg catttttgca  13500
agagttagat ttgagtgctc cagcaaggta tgacgcattc acacttagtc agattcatcc  13560
tgaactcaca tctccaaatc cggaggaaga ctacttagta cgatacttgt tcagagggat  13620
agggactgca tcttcctctt ggtataaggc atcccatctc ctttctgtac ccgaggtaag  13680
atgtgcaaga cacgggaact ccttatactt ggctgaagga agcggagcca tcatgagtct  13740
tcttgaactg catgtaccac atgaaactat ctattacaat acgctctttt caaatgagat  13800
gaaccccccg caacgacatt tcgggccgac cccaactcag tttttgaatt cggttgttta  13860
taggaatcta caggcggagg taacatgcaa ggatggattt gtccaagagt tccgtccatt  13920
atggagagaa aatacagagg aaagtgacct gacctcagat aaagcagtgg ggtatattac  13980
atctgcagta ccctacagat ctgtatcatt gctgcattgt gacattgaaa ttcctccagg  14040
gtccaatcaa agcttactag atcaactagc tatcaattta tctctgattg ccatgcattc  14100
tgtaagggag ggcggggtag taatcatcaa agtgttgtat gcaatgggat actactttca  14160
tctactcatg aacttgtttg ctccgtgttc cacaaaagga tatattctct ctaatggtta  14220
tgcatgtcga ggggatatgg agtgttacct ggtatttgtc atgggttacc tgggcgggcc  14280
tacatttgta catgaggtgg tgaggatggc aaaaactctg gtgcagcggc acggtacgct  14340
cttgtctaaa tcagatgaga tcacactgac caggttattc acctcacagc ggcagcgtgt  14400
gacagacatc ctatccagtc ctttaccaag attaataaag tacttgagga agaatattga  14460
cactgcgctg attgaagccg ggggacagcc cgtccgtcca ttttgtgcgg aaagtttggt  14520
gagcacgcta gcgaacataa ctcagataac ccagattatc gctagtcaca ttgacacagt  14580
catccggtct gtgatatata tggaagctga gggtgatctc gctgacacag tatttctatt  14640
taccccttac aatctctcta ctgacgggaa aaagaggaca tcacttaaac agtgcacgag  14700
acagatccta gaggttacaa tactaggtct tagagtcgaa aatctcaata aaataggcga  14760
tataatcagc ctagtgctta aaggcatgat ctccatggag gaccttatcc cactaaggac  14820
atacttgaag catagtacct gccctaaata tttgaaggct gtcctaggta ttaccaaact  14880
caaagaaatg tttacagaca cttctgtact gtacttgact cgtgctcaac aaaaattcta  14940
catgaaaact ataggcaatg cagtcaaagg atattacagt aactgtgact cctaacgaaa  15000
atcacatatt aataggctcc ttttttggcc aattgtattc ttgttgattt aattatatta  15060
tgttagaaaa aagttgaact ctgactcctt aggactcgaa ttcgaactca aataaatgtc  15120
tttaaaaaag gttgcgcaca attattcttg agtgtagtct cgtcattcac caaatctttg  15180
```

tttggt 15186

<210> SEQ ID NO 11
<211> LENGTH: 10
<212> TYPE: PRT
<213> ORGANISM: Artificial Sequence
<220> FEATURE:
<223> OTHER INFORMATION: a consensus sequence based on avirulent avian strains of influenza A H5 in the region immediately before the HA cleavage site

<400> SEQUENCE: 11

```
Gln Arg Glu Arg Arg Arg Lys Lys Arg Gly
 1              5                  10
```

<210> SEQ ID NO 12
<211> LENGTH: 6
<212> TYPE: PRT
<213> ORGANISM: Artificial Sequence
<220> FEATURE:
<223> OTHER INFORMATION: altered consensus sequence based on avirulent avian strains of influenza A H5 in the region immediately before the HA cleavage site

<400> SEQUENCE: 12

```
Gln Arg Glu Thr Arg Gly
 1              5
```

<210> SEQ ID NO 13
<211> LENGTH: 33
<212> TYPE: DNA
<213> ORGANISM: Artificial Sequence
<220> FEATURE:
<223> OTHER INFORMATION: consensus sequence based on avirulent avian strains of influenza A H5 in the region immediately before the HA cleavage site

<400> SEQUENCE: 13

```
cct caa aga gag aga aga aga aaa aag aga gga                       33
Pro Gln Arg Glu Arg Arg Arg Lys Lys Arg Gly
 1              5                   10
```

<210> SEQ ID NO 14
<211> LENGTH: 11
<212> TYPE: PRT
<213> ORGANISM: Artificial Sequence
<220> FEATURE:
<223> OTHER INFORMATION: consensus sequence based on avirulent avian strains of influenza A H5 in the region immediately before the HA cleavage site

<400> SEQUENCE: 14

```
Pro Gln Arg Glu Arg Arg Arg Lys Lys Arg Gly
 1              5                  10
```

<210> SEQ ID NO 15
<211> LENGTH: 21
<212> TYPE: DNA
<213> ORGANISM: Artificial Sequence
<220> FEATURE:
<223> OTHER INFORMATION: altered consensus sequence based on avirulent avian strains of influenza A H5 in the region immediately before the HA cleavage site

<400> SEQUENCE: 15

```
cct caa aga gag acg aga gga                                       21
Pro Gln Arg Glu Thr Arg Gly
 1              5
```

<210> SEQ ID NO 16
<211> LENGTH: 7
<212> TYPE: PRT
<213> ORGANISM: Artificial Sequence
<220> FEATURE:
<223> OTHER INFORMATION: consensus sequence based on avirulent avian strains of influenza A H5 in the region immediately before the HA cleavage site

<400> SEQUENCE: 16

Pro Gln Arg Glu Thr Arg Gly
1 5

<210> SEQ ID NO 17
<211> LENGTH: 21
<212> TYPE: DNA
<213> ORGANISM: Artificial Sequence
<220> FEATURE:
<223> OTHER INFORMATION: further altered DNA consensus sequence based on avirulent avian strains of influenza A H5 in the region immediately before the HA cleavage site

<400> SEQUENCE: 17
cctcagcggg agacgcgggg a 21

<210> SEQ ID NO 18
<211> LENGTH: 10
<212> TYPE: DNA
<213> ORGANISM: Artificial Sequence
<220> FEATURE:
<223> OTHER INFORMATION: "gene end" sequence engineered to the genes which were inserted into the NDV as an extratransciptional units

<400> SEQUENCE: 18
ttagaaaaaa 10

<210> SEQ ID NO 19
<211> LENGTH: 10
<212> TYPE: DNA
<213> ORGANISM: Artificial Sequence
<220> FEATURE:
<223> OTHER INFORMATION: "gene start" sequence engineered to the genes which were inserted into the NDV as an extratransciptional units

<400> SEQUENCE: 19
acgggtagaa 10

<210> SEQ ID NO 20
<211> LENGTH: 74
<212> TYPE: DNA
<213> ORGANISM: Artificial Sequence
<220> FEATURE:
<223> OTHER INFORMATION: PCR primer used to produce ectodomain (ECTO) of the H5 HA gene

<400> SEQUENCE: 20
cggctagctt agaaaaaata cggtagaagt gaaactagtc cgccaccatg gaaagaatag 60
tgattgcctt tgca 74

<210> SEQ ID NO 21
<211> LENGTH: 33
<212> TYPE: DNA
<213> ORGANISM: Artificial Sequence
<220> FEATURE:
<223> OTHER INFORMATION: PCR primer used to produce ectodomain (ECTO)

of the H5 HA gene

<400> SEQUENCE: 21
cggttaacct gataagcccc cattgattct aat 33

<210> SEQ ID NO 22
<211> LENGTH: 32
<212> TYPE: DNA
<213> ORGANISM: Artificial Sequence
<220> FEATURE:
<223> OTHER INFORMATION: PCR primer used to amplify TM and CT of the NDV F gene

<400> SEQUENCE: 22
cggttaacct cattacctat atcgttttga ct 32

<210> SEQ ID NO 23
<211> LENGTH: 46
<212> TYPE: DNA
<213> ORGANISM: Artificial Sequence
<220> FEATURE:
<223> OTHER INFORMATION: PCR primer used to amplify TM and CT of the NDV F gene

<400> SEQUENCE: 23
cggagctcaa gctagcttat cacatttttg tagtggctct catctg 46

<210> SEQ ID NO 24
<211> LENGTH: 24
<212> TYPE: DNA
<213> ORGANISM: Artificial Sequence
<220> FEATURE:
<223> OTHER INFORMATION: forward primer F2aa-1(+) used to generate rNDV/F2aa

<400> SEQUENCE: 24
ggatcccggt tggcgccctc cagg 24

<210> SEQ ID NO 25
<211> LENGTH: 38
<212> TYPE: DNA
<213> ORGANISM: Artificial Sequence
<220> FEATURE:
<223> OTHER INFORMATION: reverse primer F2aa-1(-) used to generate rNDV/F2aa

<400> SEQUENCE: 25
aaggcgcctc tgtctccgcc ctccagatgt agtcacag 38

<210> SEQ ID NO 26
<211> LENGTH: 37
<212> TYPE: DNA
<213> ORGANISM: Artificial Sequence
<220> FEATURE:
<223> OTHER INFORMATION: forward primer F2aa-2(+) used to generate rNDV/F2aa

<400> SEQUENCE: 26
ggcggagaca gaggcgcctt ataggcgcca ttattgg 37

<210> SEQ ID NO 27
<211> LENGTH: 24
<212> TYPE: DNA
<213> ORGANISM: Artificial Sequence
<220> FEATURE:
<223> OTHER INFORMATION: reverse primer F2aa-2(-) used to generate rNDV/F2aa

<400> SEQUENCE: 27
ccatattccc accagctaga ttgt 24

<210> SEQ ID NO 28
<211> LENGTH: 24
<212> TYPE: DNA
<213> ORGANISM: Artificial Sequence
<220> FEATURE:
<223> OTHER INFORMATION: forward primer F3aa-1(+) used to generate rNDV/F3aa

<400> SEQUENCE: 28
ggatcccggt tggcgccctc cagg 24

<210> SEQ ID NO 29
<211> LENGTH: 38
<212> TYPE: DNA
<213> ORGANISM: Artificial Sequence
<220> FEATURE:
<223> OTHER INFORMATION: reverse primer F3aa-1(-) used to generate rNDV/F3aa

<400> SEQUENCE: 29
aaagcgcctc tgtctccgcc ctccagatgt agtcacag 38

<210> SEQ ID NO 30
<211> LENGTH: 37
<212> TYPE: DNA
<213> ORGANISM: Artificial Sequence
<220> FEATURE:
<223> OTHER INFORMATION: forward primer F3aa-2(+) used to generate rNDV/F3aa

<400> SEQUENCE: 30
ggcggagaca gaggcgcttt ataggcgcca ttattgg 37

<210> SEQ ID NO 31
<211> LENGTH: 24
<212> TYPE: DNA
<213> ORGANISM: Artificial Sequence
<220> FEATURE:
<223> OTHER INFORMATION: reverse primer F3aa-2(-) used to generate rNDV/F3aa

<400> SEQUENCE: 31
ccatattccc accagctaga ttgt 24

<210> SEQ ID NO 32
<211> LENGTH: 32
<212> TYPE: DNA
<213> ORGANISM: Artificial Sequence
<220> FEATURE:
<223> OTHER INFORMATION: HpaNDV F(TM+CYTO)P primer used to generate chimeric H7HA gene

<400> SEQUENCE: 32
cggttaacct cattacctat atcgttttga ct 32

<210> SEQ ID NO 33
<211> LENGTH: 46
<212> TYPE: DNA
<213> ORGANISM: Artificial Sequence
<220> FEATURE:
<223> OTHER INFORMATION: SacNheNDVF(TM+CYTO)M primer used to generate chimeric H7HA gene

```
<400> SEQUENCE: 33

cggagctcaa gctagcttat cacatttttg tagtggctct catctg                46


<210> SEQ ID NO 34
<211> LENGTH: 42
<212> TYPE: DNA
<213> ORGANISM: Artificial Sequence
<220> FEATURE:
<223> OTHER INFORMATION: SpeH7(ECTO)P primer used to generate
      chimeric H7HA gene

<400> SEQUENCE: 34

cgactagtcc gccaccatga acactcaaat tctggcattc at                    42


<210> SEQ ID NO 35
<211> LENGTH: 35
<212> TYPE: DNA
<213> ORGANISM: Artificial Sequence
<220> FEATURE:
<223> OTHER INFORMATION: HpaH7(ECTO)M primer used to generate
      chimeric H7HA gene

<400> SEQUENCE: 35

cggttaacgt ctttgtatcc actactcaat ttcac                            35


<210> SEQ ID NO 36
<211> LENGTH: 52
<212> TYPE: DNA
<213> ORGANISM: Artificial Sequence
<220> FEATURE:
<223> OTHER INFORMATION: partical H7HA with GE/GS and Kozak sequence

<400> SEQUENCE: 36

gctagcttag aaaaaatacg ggtagaacac tagtccgcca ccatggtcag ct         52
```

CHIMERIC VIRUSES PRESENTING NON-NATIVE SURFACE PROTEINS AND USES THEREOF

This application claims priority to U.S. Provisional Application Ser. No. 60/741,833, filed Dec. 2, 2005 and to U.S. Provisional Application Ser. No. 60/802,864, filed May 22, 2006, both of which are incorporated herein by reference in their entireties.

1. FIELD OF THE INVENTION

The present invention provides chimeric negative-stand RNA viruses that allow a subject, e.g., an avian, to be immunized against two infectious agents by using a single chimeric virus of the invention. In particular, the present invention provides chimeric influenza viruses engineered to express and incorporate into their virions a fusion protein comprising an ectodomain of a protein of an infectious agent and the transmembrane and cytoplasmic domain of an influenza virus protein. Such chimeric viruses induce an immune response against influenza virus and the infectious agent. The present invention also provides chimeric Newcastle Disease viruses (NDV) engineered to express and incorporate into their virions a fusion protein comprising the ectodomain of a protein of an infectious agent and the transmembrane and cytoplasmic domain of an NDV protein. Such chimeric viruses induce an immune response against NDV and the infectious agent.

2. BACKGROUND OF THE INVENTION

A number of DNA viruses have been genetically engineered to direct the expression of heterologous proteins in host cell systems (e.g., vaccinia virus, baculovirus, etc.). Recently, similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccinia will, therefore, not induce immune stimulation.

By contrast, the negative-strand RNA viruses, are attractive candidates for constructing chimeric viruses for use in vaccines. Negative-strand RNA viruses, for example, influenza, are desirable because their wide genetic variability allows for the construction of a vast repertoire of vaccine formulations which stimulate immunity without risk of developing a tolerance.

2.1 Negative-Strand RNA Viruses

The virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). The Paramyxoviridae and Orthomyxoviridae families are described in detail below and used in the examples herein. The Paramyxoviridae family contains the viruses of Newcastle disease Virus (NDV), parainfluenza virus, Sendai virus, simian virus 5, and mumps virus. The Orthomyxoviridae family contains the viruses of influenza, types A, B and C viruses, as well as Thogoto and Dhori viruses and infectious salmon anemia virus.

2.1.1 Influenza Virus

The influenza virions comprise an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode ten polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP). Transcription and replication of the genome takes place in the nucleus and assembly occurs via budding on the plasma membrane. The viruses can reassort genes during mixed infections.

Influenza virus adsorbs to cells via HA binding activity to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. The viral RNA transcripts then migrate to the cell membrane and associate with the newly transcribed, transmembrane viral proteins. NA then cleaves sialy residues from the carbohydrate moieties of membrane bound glycoproteins resulting in encapsulation and cellular release of the progeny virus. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for ten proteins: nine structural and one nonstructural. A summary of the genes of the influenza virus and their protein products is shown in Table 1 below.

TABLE 1

INFLUENZA VIRUS GENOME RNA SEGMENTS AND CODING ASSIGNMENTS[a]

| Segment | $Length_b$ (Nucleotides) | Encoded $Polypeptide_c$ | $Length_d$ (Amino Acids) | Molecules Per Virion | Comments |
|---|---|---|---|---|---|
| 1 | 2341 | PB2 | 759 | 30-60 | RNA transcriptase component; host cell RNA cap binding |
| 2 | 2341 | PB1 | 757 | 30-60 | RNA transcriptase component; initiation of transcription |

TABLE 1-continued

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 3 | 2233 | PA | 716 | 30-60 | RNA transcriptase component |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |
| | | $M_2$ | 96 | ? | Structural protein in plasma membrane; spliced mRNA |
| 8 | 890 | $NS_1$ | 230 | | Nonstructural protein; |
| | | NEP | 121 | ? | Nuclear export protein; spliced mRNA |

[a]Adapted from R. A. Lamb and P. W. Choppin (1983), Annual Review of Biochemistry, Volume 52, 467-506.
[b]For A/PR/8/34 strain
[c]Determined by biochemical and genetic approaches
[d]Determined by nucleotide sequence analysis and protein sequencing The pathogenicity of influenza viruses is modulated by multiple virus and host factors. Among the host factors that fight virus infections, the type I interferon (IFNα/β) system represents a powerful antiviral innate defense mechanism which was established relatively early in the evolution of eukaryotic organisms (García-Sastre, 2002, Microbes Infect 4:647-55). The antiviral IFNα/β system involves three major steps: (i) detection of viral infection and IFNα/β secretion, (ii) binding of IFNα/β to its receptors and transcriptional induction of IFNα/β-stimulated genes, and (iii) synthesis of antiviral enzymes and proteins. Most viruses, however, have acquired specific genetic information encoding IFNα/β antagonist molecules, which effectively block one or more steps of the antiviral IFNα/β system. Influenza A viruses express a non-structural protein in infected cells, the NS1 protein (described in detail, infra), which counteracts the cellular IFNα/β response (García-Sastre et al., 1998, Virology 252:324-30).

2.1.1.1 High-Pathogenenicity Avian Influenza

In recent years, outbreaks of high pathogenic avian influenza (HPAI) have been reported in Asia and Europe (Kawaoka et al., 2005, Natl. Rev. Microbiol. 3:591-600; Koopmans et al., 2004, Lancet 363:587-593). Outbreaks involving influenza A, subtype H5N1 or H7N7 viruses resulted in lethal infections in domestic poultry, and the death of a limited number of human cases (Tweed et al., 2004, Emerg. Infec. Dis. 10:2196-2199). The current H5N1 viruses have been circulating among poultry within China in recent years (Chen et al., 2005, Nature 436:191-192), and while migratory birds are considered to be the primary reservoir of these viruses, transmission from infected poultry back to migratory birds is believed to have contributed to their increased geographical distribution. Currently, the H5N1 virus has emerged from Asia, spreading across Europe and Africa (Enserink, 2006, Science, 311:932). Wholesale culling of poultry has been shown to be a successful strategy in eradicating H5N1 outbreaks in Hong Kong in 1997 and the Netherlands in 2003 (Lipatov et al., 2004, J. Virol. 78:8951-8959). As human victims of recent HPAI outbreaks have had close contact with infected poultry, it follows that the prevention of interspecies transmission of avian influenza viruses (AIV) may be accomplished by the eradication of AIV in poultry through slaughter. However, for economic and practical reasons, the destruction of infected poultry alone is no longer considered the method of choice in the control of this disease. In addition, for ethical and ecological reasons, the culling of migratory wildfowl is considered an unacceptable practice. Recently, OIE (World Organization for Animal Health) and FAO (Food and Agriculture Organization of the United Nations) recommended that vaccination of poultry should be considered for the control of AIV. In addition, it has been reported that vaccination of chickens with inactivated H5 vaccine was successful in the interruption of virus transmission in a field study (Ellis et al., 2004, Avian Pathol. 33:405-412). Recently, China has accepted vaccination as a component of their AIV control program.

The possibility of that the highly pathogenic H5N1 strain can become transmissible between humans is referenced in terms of a global pandemic, with the WHO unwilling to estimate the global mortality should the H5N1 virus recombine to human form. Therefore, the need for a method of management of H5N1 infection in agricultural stocks, from which most transmissions to humans are believed to have arisen, is clear.

2.1.2 Newcastle Disease Virus

The Newcastle Disease Virus is an enveloped virus containing a linear, single-strand, nonsegmented, negative sense RNA genome. The genomic RNA contains genes in the order of 3'-N-P-M-F-HN-L, described in further detail below. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrudes from the envelope providing both hemagglutinin (e.g., receptor binding/fusogenic) and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (N) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication.

The replication of all negative-strand RNA viruses, including NDV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the virus can not synthesize the required RNA-dependent RNA polymerase. The L, P and N proteins must enter the cell along with the genome on infection.

It is hypothesized that most or all of the viral proteins that transcribe NDV mRNA also carry out their replication. The mechanism that regulates the alternative uses (i.e., transcription or replication) of the same complement of proteins has not been clearly identified but appears to involve the abundance of free forms of one or more of the nucleocapsid proteins, in particular, the N. Directly following penetration of the virus, transcription is initiated by the L protein using the negative-sense RNA in the nucleocapsid as a template. Viral RNA synthesis is regulated such that it produces monocistronic mRNAs during transcription.

Following transcription, virus genome replication is the second essential event in infection by negative-strand RNA viruses. As with other negative-strand RNA viruses, virus genome replication in Newcastle disease virus (NDV) is mediated by virus-specified proteins. The first products of replicative RNA synthesis are complementary copies (i.e., plus-polarity) of NDV genome RNA (cRNA). These plus-stranded copies (anti-genomes) differ from the plus-strand mRNA transcripts in the structure of their termini. Unlike the mRNA transcripts, the anti-genomic cRNAs are not capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of NDV negative-strand viral genomes (vRNAs).

Both the NDV negative strand genomes (vRNAs) and antigenomes (cRNAs) are encapsidated by nucleocapsid proteins; the only unencapsidated RNA species are virus mRNAs. For NDV, the cytoplasm is the site of virus RNA replication, just as it is the site for transcription. Assembly of the viral components appears to take place at the host cell plasma membrane and mature virus is released by budding.

2.2 Immunogenic Formulations

Recombinant DNA technology and "reverse genetics" engineering techniques afford a unique approach to the production of recombinant viruses for the use in immunogenic formulations. In particular, the present invention provides for a method to engineer a negative-strand RNA virus such that it expresses, or displays, not only native viral antigens, but also any antigen that may be designed to incorporate into the viral protein coat. Of particular interest are antigens derived from infectious organisms other than influenza. In this manner a single virus may be engineered as an immunogenic compound useful to illicit, activate or induce an immune response which would afford protection against at least two pathogens. Such a chimeric virus may be further engineered when necessary to modify their virulence, i.e., so that they may be attenuated or further attenuated. Attenuated influenza viruses are beneficial because they are immunogenic and capable of replication, but not pathogenic.

Live vaccines are thought to induce improved cross-reactive cell-mediated cytotoxicity as well as a humoral antibody response, providing better protection than inactivated vaccines (Gorse and Belshe, 1990, J. Clin. Microbiol. 28:2539-2550; and Gorse et al., 1995, J. Infect. Dis. 172:1-10). Secondly, protective immunity to viral diseases is likely to involve mucosal IgA response which is not seen with traditional intramuscularly administered vaccines (Nelson et al., 1998, Vaccine 16:1306-1313). Finally, live vaccines also have the advantage of intranasal administration which avoids the swelling and muscle soreness occasionally associated with the intramuscular administration of inactivated adjuvanted vaccines. These live vaccines have been reported to induce not only humoral responses against homotypic influenza virus but also crossreactive cell-mediated cytotoxicity. Thus, the invention offers the potential for the development of new and more effective immune formulations, e.g., vaccine formulations, for the diagnosis, prevention, management or treatment of both viral and non-viral pathogens.

3. SUMMARY OF THE INVENTION

The present invention provides chimeric negative strand RNA viruses engineered to express fusion proteins that incorporate into the virion, methods for producing such chimeric viruses and the use of such viruses, for example as immunogens, in immunogenic formulations, or in in vitro assays. The chimeric viruses of the invention are characterized by displaying, on the surface of the virion, not only antigens associated with the virus but also the fusion protein.

The present invention provides chimeric influenza viruses and chimeric NDVs that allow a subject, e.g., an avian or human, to be immunized against two infectious agents by administering a chimeric influenza virus or a chimeric NDV. In one aspect, the use of a single virus for inducing an immune response reduces the frequency of administration of an immunizing formulation. In another aspect, the use of a single virus for inducing an immune response reduces the cost of immunizing subjects. The lower cost of immunizing subjects increases the likelihood that more subjects will be able to afford to be immunized and thus, reduces the health costs associated with treating subjects suffering from an infection.

The invention also relates to the use of the chimeric virus of the invention in compositions (e.g., immunogenic formulations) for humans or animals. In particular, the chimeric viruses of the invention can be used as vaccines against a broad range of viruses and/or antigens. Because the chimeric virus is engineered to express foreign epitopes in the virion, compositions (e.g., vaccine formulations) comprising a chimeric virus of the invention can be designed for immunization against multiple strain variants, different viruses or against completely different infectious agents or disease antigens (e.g., bacteria, parasites, fungi or tumor specific antigens). Many methods may be used to introduce the live attenuated virus formulations to a human or animal subject to induce an immune or appropriate cytokine response. These include, but are not limited to, intranasal, intratrachial, oral, intradermal, intramuscular, intraperitoneal, intravenous and subcutaneous routes.

The chimeric viruses of the invention enable a subject (e.g. avians) to be immunized for two infectious diseases by administering the chimeric viruses. In a specific embodiment, the chimeric viruses of the invention enable avians to be immunized for avian influenza virus and Newcastle Disease virus by administering a chimeric virus of the invention. The avians can be readily immunized by spraying them with the chimeric virus or administering the chimeric virus in an aqueous solution, such as the water that they drink.

The present invention is based, in part, on Applicants' discovery that an effective immune response to two infectious agents can be achieved by engineering an influenza virus to express and incorporate into its virion a fusion protein comprising the cytoplasmic and transmembrane domains of at least one essential glycoprotein of the virus and the ectodomain of a protein of a second infectious agent, wherein the fusion protein functionally replaces the essential glycoprotein. In one aspect, incorporation of the fusion protein into the virion results in an enhanced immune response to the ectodomain of the second infectious agent. Engineering the cytoplasmic and transmembrane domains of an essential glycoprotein of the virus into the fusion protein allows the fusion protein to incorporate into the virion. In a particular embodiment, the essential glycoprotein is one or both of the influenza virus HA and/or NA protein. In another embodiment, the essential glycoprotein is one or both of the HN or F protein of NDV. The functional replacement of at least one essential glycoprotein of the virus eliminates the concern about the size limitation of the virus genome (e.g. the influenza virus genome). In certain embodiments, the functional replacement of at least one essential glycoprotein of the virus with the fusion protein attenuates viral replication in subjects.

The present invention provides a chimeric avian influenza virus, comprising a fusion protein, having (i) an ectodomain of a protective antigen of an infectious agent, other than influenza virus fused to (ii) a transmembrane and cytoplasmic domain of a glycoprotein encoded by an essential gene of an influenza virus, wherein the fusion protein is incorporated into an avian influenza virus, in which the function of the essential gene is supplied by the fusion protein or by the glycoprotein native to the avian influenza virus. In certain embodiments, the essential gene of an influenza virus is a hemagglutinin (HA) gene. In other embodiments, the essential gene of an influenza virus is a neuraminidase (NA) gene. In certain embodiments, the chimeric avian influenza virus is attenuated. In accordance with these embodiments, the chimeric avian influenza virus may be attenuated by mutations in the NS1 gene.

The present invention provides a chimeric avian influenza virus, comprising a fusion protein, having (i) an ectodomain of an NDV HN protein fused to (ii) a transmembrane domain and cytoplasmic domain of an influenza virus NA protein, wherein the fusion protein is incorporated into an avian influenza virus, in which the function of the NA protein is supplied by the fusion protein or by the glycoprotein native to the avian influenza virus. In certain embodiments, the chimeric avian influenza virus is attenuated. In accordance with these embodiments, the chimeric avian influenza virus may be attenuated by mutations in the NS1 gene. In accordance with the invention, any avian influenza virus type, subtype or strain may be used.

The present invention provides a chimeric avian influenza virus, comprising a packaged influenza virus NA segment encoding a neuraminidase fusion protein, in which the NA open reading frame is modified so that the nucleotides encoding the NA ectodomain are replaced by nucleotides encoding an ectodomain of a neuraminidase antigen of an infectious agent other than influenza that is anchored by the N-terminus, so that the neuraminidase fusion protein is expressed and incorporated into the chimeric avian influenza virus.

The present invention provides a chimeric avian influenza virus, comprising a packaged influenza virus HA segment encoding a hemagglutinin fusion protein, in which the HA open reading frame is modified so that the nucleotides encoding the HA ectodomain are replaced by nucleotides encoding an ectodomain of a receptor binding/fusogenic antigen of an infectious agent other than influenza virus that is anchored by the C-terminus, so that the hemagglutinin fusion protein is expressed and incorporated into the chimeric avian influenza virus.

The present invention provides a chimeric avian influenza virus, comprising a packaged bicistronic influenza virus HA segment, comprising: (a) a first open reading frame that encodes an avian influenza virus hemagglutinin protein, and (b) a second open reading frame that encodes a hemagglutinin fusion protein, in which the nucleotides encoding the hemagglutinin ectodomain are replaced by nucleotides encoding an ectodomain of a protective antigen of an infectious agent, other than influenza virus, or encoding a disease antigen that is anchored by the C-terminus, so that both the influenza virus hemagglutinin and the fusion protein are expressed and incorporated into the chimeric avian influenza virus. In certain embodiments, the first open reading frame of the HA segment of the chimeric avian virus is modified to remove the hemagglutinin polybasic cleavage site.

The present invention provides a chimeric avian influenza virus, comprising a packaged bicistronic influenza virus NA segment, comprising: (a) a first open reading frame that encodes an avian influenza virus neuraminidase protein, and (b) a second open reading frame that encodes a neuraminidase fusion protein, in which the nucleotides encoding the neuraminidase ectodomain are replaced by nucleotides encoding an ectodomain of a protective antigen of an infectious agent, other than influenza virus, or encoding a disease antigen that is anchored by the N-terminus, so that both the influenza virus neuraminidase and the fusion protein are expressed and incorporated into the chimeric avian influenza virus. In certain embodiments, the chimeric avian influenza virus comprises an HA segment having an open reading frame modified to remove the hemagglutinin polybasic cleavage site.

The present invention provides a chimeric avian influenza virus, comprising a packaged influenza virus NA segment encoding a neuraminidase fusion protein, in which the NA open reading frame is modified so that the nucleotides encoding the NA ectodomain are replaced by nucleotides encoding an ectodomain of an HN antigen of NDV, so that the neuraminidase fusion protein is expressed and incorporated into the chimeric avian influenza virus. The neuraminidase fusion protein supplies the neuraminidase activity for the chimeric avian influenza virus.

In certain embodiments, a chimeric avian influenza virus of the invention comprises a packaged NS1 gene segment encoding a modified NS1 protein that reduces the cellular interferon antagonist activity of the virus. Non-limiting examples of mutations in the NS1 gene that result in a modified NS1 protein are provided in Section 5.1.2, infra.

The present invention provides recombinant nucleic acid molecules (e.g., recombinant DNA molecules) encoding the NA segment of the chimeric avian influenza viruses of the invention. The present invention also provides recombinant nucleic acid molecules (e.g., recombinant DNA molecules) encoding the HA segment of the chimeric avian influenza viruses of the invention. The present invention further provides recombinant nucleic acid molecules (e.g., recombinant RNA molecules) coding for the NA segment or the HA segment of the chimeric avian influenza viruses of the invention.

The present invention provides methods for propagating a chimeric avian influenza virus of the invention, comprising culturing the chimeric avian influenza virus in an embryonated egg or a cell line that is susceptible to avian influenza virus infection. The present invention also provides methods for producing an immunogenic formulation, the method comprising: (a) propagating a chimeric avian influenza virus of the invention in an embryonated egg or a cell line that is susceptible to avian influenza virus infection; and (b) collecting the progeny virus, wherein the virus is grown to sufficient quantities and under sufficient conditions that the virus is free from contamination, such that the progeny virus is suitable for use in immunogenic formulations, e.g., vaccine formulations.

The present invention provides an attenuated chimeric influenza virus, comprising a fusion protein, having (i) an ectodomain of a protective antigen of an infectious agent, other than influenza virus fused to (ii) a transmembrane and cytoplasmic domain of a glycoprotein encoded by an essential gene of an influenza virus, wherein the fusion protein is incorporated into an attenuated influenza virus, in which the function of the essential gene is supplied by the fusion protein or by the glycoprotein native to the attenuated influenza virus. In certain embodiments, the essential gene of an influenza virus is a hemagglutinin (HA) gene. In other embodiments, the essential gene of an influenza virus is a neuraminidase (NA) gene. The attenuated chimeric influenza virus may be any type, subtype or strain of influenza virus. For example, the attenuated chimeric influenza virus may be an influenza A virus, an influenza B virus or an influenza C virus.

The present invention provides an attenuated chimeric influenza virus, comprising a packaged influenza virus NA segment encoding a neuraminidase fusion protein, in which the NA open reading frame is modified so that the nucleotides encoding the NA ectodomain are replaced by nucleotides encoding an ectodomain of a neuraminidase antigen of an infectious agent other than influenza that is anchored by the N-terminus, so that the neuraminidase fusion protein is expressed and incorporated into the attenuated chimeric avian influenza virus. In certain embodiments, the attenuated chimeric influenza virus of the invention comprises an HA segment having an open reading frame modified to remove the hemagglutinin polybasic cleavage site.

The present invention provides an attenuated chimeric influenza virus, comprising a packaged influenza virus HA segment encoding a hemagglutinin fusion protein, in which the HA open reading frame is modified so that the nucleotides encoding the HA ectodomain are replaced by nucleotides encoding an ectodomain of a hemagglutinin antigen of an infectious agent other than influenza that is anchored by the C-terminus, so that the hemagglutinin fusion protein is expressed and incorporated into the attenuated chimeric influenza virus.

The present invention provides an attenuated chimeric influenza virus, comprising a packaged bicistronic influenza virus HA segment, comprising: (a) a first open reading frame that encodes an influenza hemagglutinin protein, and (b) a second open reading frame that encodes a hemagglutinin fusion protein, in which the nucleotides encoding the hemagglutinin ectodomain are replaced by nucleotides encoding an ectodomain of a protective antigen of an infectious agent, other than influenza, or encoding a disease antigen that is anchored by the C-terminus, so that both the influenza hemagglutinin and the fusion protein are expressed and incorporated into the attenuated chimeric influenza virus. In certain embodiments, the first open reading frame of the HA segment of the attenuated chimeric influenza virus is modified to remove the hemagglutinin polybasic cleavage site.

The present invention provides an attenuated chimeric influenza virus, comprising a packaged bicistronic influenza virus NA segment, comprising: (a) a first open reading frame that encodes an influenza neuraminidase protein, and (b) a second open reading frame that encodes a neuraminidase fusion protein, in which the nucleotides encoding the neuraminidase ectodomain are replaced by nucleotides encoding an ectodomain of a protective antigen of an infectious agent, other than influenza, or encoding a disease antigen that is anchored by the N-terminus, so that both the influenza neuraminidase and the fusion protein are expressed and incorporated into the attenuated chimeric influenza virus. In certain embodiments, the attenuated chimeric influenza virus of the invention comprises an HA segment having an open reading frame modified to remove the hemagglutinin polybasic cleavage site.

In certain embodiments, the attenuated chimeric influenza virus of the invention comprise a packaged NS1 gene segment encoding a modified NS1 protein that reduces the cellular interferon antagonist activity of the virus.

The present invention provides recombinant nucleic acid molecules (e.g., recombinant DNA molecules) encoding the NA segment of the attenuated chimeric influenza viruses of the invention. The present invention also provides recombinant nucleic acid molecules (e.g., recombinant DNA molecules) encoding the HA segment the attenuated chimeric influenza viruses of the invention. The present invention further provides recombinant nucleic acid molecules (e.g., recombinant RNA molecules) coding the NA segment or HA segment of the attenuated chimeric influenza viruses of the invention.

The present invention provides methods for propagating an attenuated chimeric influenza virus of the invention, comprising culturing the attenuated chimeric influenza virus in an embryonated egg or a cell line that is susceptible to influenza virus infection. The present invention also provides methods for producing an immunogenic formulation, the method comprising: (a) propagating an attenuated chimeric influenza virus of the invention in an embryonated egg or a cell line that is susceptible to attenuated influenza virus infection; and (b) collecting the progeny virus, wherein the virus is grown to sufficient quantities and under sufficient conditions that the virus is free from contamination, such that the progeny virus is suitable for use in immunogenic formulations, e.g., vaccine formulations.

The present invention also provides chimeric NDV viruses. In particular, the present invention provides a chimeric NDV, comprising a fusion protein, having (i) an ectodomain of a protective antigen of an infectious agent, other than NDV fused to (ii) a transmembrane and cytoplasmic domain of a glycoprotein encoded by an essential gene of an NDV, wherein the fusion protein is incorporated into an NDV, in which the function of the essential gene is supplied by the fusion protein or by the glycoprotein native to the NDV. In certain embodiments, the essential NDV gene of NDV is the gene encoding an F protein. In other embodiments, the essential NDV gene of NDV is the gene encoding an HN protein. In accordance with the invention, any NDV type, subtype or strain can be used.

The present invention provides a chimeric NDV, comprising a packaged genome comprising a nucleotide sequence encoding an F protein-fusion protein having the transmembrane and cytoplasmic domains of an F protein and the ectodomain of an antigen of an infectious agent, other than NDV, or a disease antigen that is anchored by the C-terminus, so that the F protein-fusion protein is expressed and incorporated into the chimeric NDV. In certain embodiments, the genome of the chimeric NDV comprises a nucleotide sequence encoding an F protein, so that the F protein is expressed and incorporated into the chimeric NDV in addition to the NDV F protein-fusion protein. In other embodiments, the nucleotide sequence encoding the NDV F protein-fusion protein replaces the nucleotide sequence encoding the NDV F protein and the F protein-fusion protein supplies the function of the F protein for the chimeric NDV.

The present invention provides a chimeric NDV, comprising a packaged genome comprising a nucleotide sequence encoding an HN fusion protein having the transmembrane and cytoplasmic domains of an HN protein and the ectodomain of an antigen of an infectious agent, other than NDV, or a disease antigen that is anchored by the N-terminus, so that the HN fusion protein is expressed and incorporated into the chimeric NDV. In certain embodiments, the genome of the chimeric NDV comprises a nucleotide sequence encoding an HN protein, so that the HN protein is expressed and incorporated into the chimeric NDV in addition to the NDV HN fusion protein. In other embodiments, the nucleotide sequence encoding the HN fusion protein replaces the nucleotide sequence encoding the NDV HN protein and the HN fusion protein supplies the function of the HN protein for the chimeric NDV. The present invention provides recombinant nucleic acid molecules encoding and/or coding the NDV HN protein or F protein.

The present invention provides methods for propagating a chimeric NDV of the invention, comprising culturing the chimeric NDV in an embryonated egg or a cell line that is susceptible to NDV infection. The present invention also provides a method for producing an immunogenic formulation, the method comprising: (a) propagating a chimeric NDV of the invention in an embryonated egg or a cell line that is susceptible to NDV infection; and (b) collecting the progeny virus, wherein the virus is grown to sufficient quantities and under sufficient conditions that the virus is free from contamination, such that the progeny virus is suitable for use in immunogenic formulations, e.g., vaccine formulations.

The present invention provides embryonated eggs comprising the chimeric viruses of the invention. The present invention also provides cell lines comprising the chimeric viruses of the invention. The present invention further provides immunogenic formulations comprising the chimeric viruses of the invention.

The present invention provides methods of inducing an immune response to one, two or more infectious agents in a subject, the method comprising administering an effective amount of a chimeric influenza virus of the invention. In certain embodiments, the subject is a human subject. In other embodiments, the subject is a non-human mammal (e.g., a pig, horse, dog, or cat). In yet other embodiments, the subject is an avian subject. In a specific embodiment, the present invention provides a method of inducing an immune response to one, two or more infectious agents in an avian, the method comprising administering an effective amount of a chimeric avian influenza virus of the invention.

The present invention provides methods for inducing an immune response to on, two or more infectious agents in a subject, the method comprising administering to the subject an effective amount of a chimeric NDV of the invention. In certain embodiments, the subject is a human subject. In other embodiments, the subject is a non-human mammal (e.g., a pig, horse, dog, or cat). In yet other embodiments, the subject is an avian subject. In a specific embodiment, the present invention provides methods of inducing an immune response to one, two or more infectious agents in an avian, the method comprising administering to the avian an effective amount of a chimeric NDV of the invention.

The present invention provides methods for inducing an immune response to one, two or more infectious agents in a subject, the method comprising administering to the subject an effective amount of an attenuated chimeric influenza virus of the invention. In certain embodiments, the subject is a human subject. In other embodiments, the subject is a non-human mammal (e.g., a pig, horse, dog, or cat). In yet other embodiments, the subject is an avian subject. In a specific embodiment, the present invention provides methods for inducing an immune response to one, two or more infectious agents in a human, the method comprising administering to a human in need thereof an effective amount of a chimeric virus of the invention.

The present invention provides methods for inducing an immune response to a disease antigen, the methods comprising administering to the subject an effective amount of a chimeric virus of the invention. In certain embodiments the subject is a human. In other embodiments, the subject is an avian.

3.1 Terminology

As used herein, the term "animal" includes, but is not limited to, companion animals (e.g., dogs and cats), zoo animals, farm animals (e.g., ruminants, non-ruminants, livestock and fowl), wild animals, and laboratory animals (e.g., rodents, such as rats, mice, and guinea pigs, and rabbits), and animals that are cloned or modified either genetically or otherwise (e.g., transgenic animals).

As used herein, the term "about" or "approximately" when used in conjunction with a number refers to any number within 1, 5 or 10% of the referenced number.

As used herein, the phrase "amino-terminus" of NS1 refers to the amino acids from the amino terminal amino acid residue (amino acid residue 1) through amino acid residue 115, amino acid residues 1 through 100, amino acid residues 1 through 75, amino acid residues 1 through 50, amino acid residues 1 through 25, or amino acid residues 1 through 10 of the influenza viral NS1 protein. Deletions from the amino terminus can include deletions consisting of 5, preferably 10, 15, 20, 25, 30, 35, 40, 45, 50, 55, 60, 65, 70, 73, 75, 80, 85, 90, 95, 99, 100, 105, 110, 115, 120, 125, 126, 130, 135, 140, 145, 150, 155, 160, 165, 170 or 175 amino acid residues from the amino terminus of NS1

As used herein, the phrase "carboxy-terminus" of NS1 refer to amino acid residues 116 through the carboxy terminal amino acid residue, amino acid residues 101 through the carboxy terminal amino acid residue, amino acid residues 76 through the carboxy terminal amino acid residue, amino acid residues 51 through the carboxy terminal amino acid residue, or amino acid residues 26 through the carboxy terminal amino acid residue of the equine influenza viral NS1 protein, when the amino-terminus of NS1 is amino acid residues 1 through amino acid residue 115, amino acid residues 1 through 100, amino acid residues 1 through 75, amino acid residues 1 through 50, or amino acid residues 1 through 25, respectively, of an influenza viral NS1 protein. Deletions from the carboxy terminus can include deletions consisting of 5, preferably 10, 15, 20, 25, 30, 35, 40, 45, 50, 55, 60, 65, 70, 73, 75, 80, 85, 90, 95, 99, 100, 105, 110, 115, 120, 125, 126, 130, 135, 140, 145, 150, 155, 160, 165, 170 or 175 amino acid residues from the carboxy terminus of NS1.

As used herein, the terms "disease" and "disorder" are used interchangeably to refer to a condition in a subject and encompass but are not limited to proliferative disorders (e.g., leukemia, fibrosis, carcinoma (including malignant, non-malignant, metastatic and non-metastatic carcinomas), and lymphoma), and infections by an infectious agent (e.g., a virus, bacteria, parasite), or a condition or symptom associated therewith.

As used herein, the term "epitopes" refers to sites, fragments or a region of a molecule (e.g., a polypeptide or protein) having antigenic or immunogenic activity in a subject. An epitope having immunogenic activity is a site, fragment or region of a molecule (e.g., polypeptide or protein) that elicits an antibody response in a subject. An epitope having antigenic activity is a site, fragment or region of a molecule to which an antibody immunospecifically binds as determined by any method well-known to one of skill in the art, for example by immunoassays.

As used herein, the term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein retains activity of the full-length protein. In another embodiment, the fragment of the full-length protein does not retain the activity of the full-length protein.

As used herein, the term "fragment" in the context of a nucleic acid encoding a polypeptide or protein refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein. In another embodiment, the fragment of the full-length protein does not retain the activity of the full-length protein.

The term "heterologous sequence" as used herein in the context of a proteinaceous agent refers to a molecule that is not found in nature to be associated with the chimeric virus backbone or, in particular, the chimeric virus glycoprotein. The term "heterologous sequence" in the context of a nucleic acid sequence or nucleic acid molecule refers to a molecule that is not found in nature to be associated with the genome of the chimeric virus backbone.

The term "immunospecifically binds an antigen" and analogous terms as used herein refer to molecules that specifically bind to an antigen and do not specifically bind to another molecule (e.g., antigen specific antibodies including both modified antibodies (i.e., antibodies that comprise a modified IgG (e.g., IgG1) constant domain, or FcRn-binding fragment thereof (e.g., the Fc-domain or hinge-Fc domain)) and unmodified antibodies (i.e., antibodies that do not comprise a modified IgG (e.g., IgG1) constant domain, or FcRn-binding fragment thereof (e.g., the Fc-domain or hinge-Fc domain)). Molecules that specifically bind one antigen may be cross-reactive with related antigens. Preferably, a molecule that specifically binds one antigen does not cross-react with other antigens. A molecule that specifically binds an antigen can be identified, for example, by immunoassays, BIAcore, or other techniques known to those of skill in the art. A molecule specifically binds an antigen when it binds to said antigen with higher affinity than to any cross-reactive antigen as determined using experimental techniques, such as radioimmunoassays (RIA) and enzyme-linked immunosorbent assays (ELISAs). See, e.g., Paul, ed., 1989, *Fundamental Immunology Second Edition*, Raven Press, New York at pages 332-336 for a discussion regarding antibody specificity.

As used herein, the term "in combination" in the context of the administration of (a) therapy(ies) to a subject, refers to the use of more than one therapy (e.g., more than one prophylactic agent and/or therapeutic agent). The use of the term "in combination" does not restrict the order in which therapies (e.g., prophylactic and/or therapeutic agents) are administered to a subject (e.g., a subject with an influenza virus infection, and NDV infection, or a condition or symptom associated therewith, or a subject with another infection (e.g., another viral infection)). A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject (e.g., a subject with an influenza virus infection, an NDV infection or a condition or symptom associated therewith, or another infection (e.g., another viral infection)).

As used herein, the phrase "interferon antagonist activity" of a proteinaceous agent refers to a protein or polypeptide, or fragment, derivative, or analog thereof that reduces or inhibits the cellular interferon immune response. In particular, a protein or polypeptide, or fragment, derivative, or analog thereof (e.g., influenza virus NS1) that has interferon antagonist activity reduces or inhibits interferon expression and/or activity. In a specific embodiment, the phrase "interferon antagonist activity" refers to virus protein or polypeptide, or fragment, derivative, or analog thereof (e.g. an influenza virus protein) that reduces or inhibits the cellular interferon immune response. A viral protein or polypeptide with interferon antagonist activity may preferentially affect the expression and/or activity of one or two types of interferon (IFN). In one embodiment, the expression and/or activity of IFN-α is affected. In another embodiment, the expression and/or activity of IFN-β is affected. In another specific embodiment, the expression and/or activity of IFN-γ is affected. In certain embodiments, the expression and/or activity of IFN-α, and/or IFN-γ in an embryonated egg or cell is reduced approximately 1 to approximately 100 fold, approximately 5 to approximately 80 fold, approximately 20 to approximately 80 fold, approximately 1 to approximately 10 fold, approximately 1 to approximately 5 fold, approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by a proteinaceous agent with interferon antagonist activity relative to the expression and/or activity of IFN-α, IFN-β, and/or IFN-γ in a control embryonated egg or a cell not expressing or not contacted with such a proteinaceous agent as measured by the techniques described herein or known to one skilled in the art.

As used herein, the phrases "IFN deficient systems" or "IFN-deficient substrates" refer to systems, e.g., cells, cell lines and animals, such as mice, chickens, turkeys, rabbits, rats, horses etc., which do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to one, two or more types of IFN, or do not respond to any type of IFN, and/or are deficient in the activity of antiviral genes induced by one, two or more types of IFN, or induced by any type of IFN.

As used herein, the terms "infection", "influenza infection", "avian influenza infection" and "NDV infection" refer to all stages of an influenza virus', an avian influenza virus', a NDV's, or another infectious agent's (e.g., another viral or a bacterial infection) life cycle in a subject (including, but not limited to the invasion by and replication of influenza virus, avian influenza virus, NDV or other infectious agent in a cell or body tissue), as well as the pathological state resulting from the invasion by and replication of influenza virus, avian influenza virus or NDV. The invasion by and multiplication of an influenza virus, avian influenza virus, NDV or other infectious agent includes, but is not limited to, the following steps: the docking of the viruses (e.g., influenza virus, avian influenza virus or NDV particle) to a cell, fusion of a virus with a cell membrane, the introduction of viral genetic information into a cell, the expression of viral proteins (e.g., influenza virus, avian influenza virus or NDV proteins), the production of new viral particles (i.e., influenza virus, avian influenza virus or NDV particles) and the release of the virus (e.g., influenza virus, avian influenza virus or NDV particles) from a cell. A respiratory infection (e.g., an influenza virus or NDV infection) may be an upper respiratory tract infection (URI), a lower respiratory tract infection (LRI), or a combination thereof. In specific embodiments, the infection is a secondary infection (e.g. secondary pneumonia) which manifests after the onset of primary infection (e.g. viral pneumonia). Secondary infections arise due to the primary infection or a symptom or condition associated therewith predisposing the infected subject to such a secondary infection. In specific embodiments, the pathological state resulting from the invasion by and replication of an influenza virus, avian influenza virus or NDV is an acute influenza virus, avian influenza virus or NDV disease. Acute stages of the respiratory infections can manifest as pneumonia and/or bronchiolitis, where such symptoms may include hypoxia, apnea, respiratory distress, rapid breathing, wheezing, cyanosis, etc. The acute stage of the respiratory infections (e.g., influenza virus and NDV infections) requires an affected individual to obtain medical intervention, such as hospitalization, administration of oxygen, intubation and/or ventilation.

As used herein, the term "isolated", in the context of viruses, refers to a virus that is derived from a single parental virus. A virus can be isolated using routine methods known to one of skill in the art including, but not limited to, those based on plaque purification and limiting dilution.

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment, a nucleic acid molecule encoding a viral protein is isolated.

As used herein, the terms "manage," "managing," and "management" refer to the beneficial effects that a subject derives from a therapy (e.g., a prophylactic or therapeutic agent), which does not result in a cure of the disease (e.g. infection). In certain embodiments, a subject is administered one or more therapies (e.g., prophylactic or therapeutic agents, such as an antibody of the invention) to "manage" an influenza virus infection, avian influenza virus or NDV infection or an infection with another infectious agent, one or more symptoms thereof, or a condition associated with, potentiated by, or potentiating an influenza virus infection or NDV infection or infection with another infectious agent, so as to prevent the progression or worsening of the infection.

As used herein, the phrase "multiplicity of infection" or "MOI" is the average number of virus per infected cell. The MOI is determined by dividing the number of virus added (ml added×Pfu) by the number of cells added (ml added×cells/ml).

As used herein, the phrase "NS1 gene" refers to the gene which encodes the nonstructural protein (NS1) in influenza. NS1 is one of the eight molecules encoded by the segmented genome of influenza A and other viruses. An "NS1 gene product" refers to a gene product (e.g., a RNA or protein) encoded by an NS1 gene. In the case of a protein, the NS1 gene product is full-length and has wild-type NS1 activity (e.g., from strain A/WSN/33).

As used herein, the terms "nucleic acids," "nucleotide sequences" and "nucleic acid molecules" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "prevent", "preventing" and "prevention" refer to the prevention of the recurrence or onset of, or a reduction in one or more symptoms of a disease (e.g., viral infection or other infectious disease) in a subject as result of the administration of a therapy (e.g., a prophylactic or therapeutic agent). For example, in the context of the administration of a therapy to a subject for an infection, "prevent", "preventing" and "prevention" refer to the inhibition or a reduction in the development or onset of an infection (e.g., an influenza virus infection, an NDV infection or a condition associated therewith or an infection other than an influenza virus or NDV infection or a condition associated therewith), or the prevention of the recurrence, onset, or development of one or more symptoms of an infection (e.g., an influenza virus infection, an NDV infection or a condition associated therewith or an infection other than an influenza virus infection, an NDV infection or a condition associated therewith), in a subject resulting from the administration of a therapy (e.g., a prophylactic or therapeutic agent), or the administration of a combination of therapies (e.g., a combination of prophylactic or therapeutic agents).

As used herein, the term "protective antigen" in the context of an infectious agent includes any molecule which is capable of eliciting a protective immune response when administered to a subject, which immune response is directed against the infectious agent.

As used herein, the terms "prophylactic agent" and "prophylactic agents" refer to any agent(s) which can be used in the prevention of a disease (e.g., an infection) or a symptom thereof (e.g., an influenza virus infection, an NDV infection or a condition or symptom associated therewith, or an infection other than an influenza virus of an NDV infection or a condition or symptom associated therewith). Preferably, a prophylactic agent is an agent which is known to be useful to, has been or is currently being used to the prevent or impede the onset, development, progression and/or severity of a disease or a symptom thereof (e.g. an infection or a condition or a symptom associated therewith).

As used herein, the phrase "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, virus that is substantially free of cellular material includes preparations of protein having less than about 30%, 20%, 10%, or 5% (by dry weight) of cellular protein (also referred to herein as a "contaminating protein"). The virus is also substantially free of culture medium, i.e., culture medium represents less than about 20%, 10%, or 5% of the volume of the virus preparation. A virus can be purified using routine methods known to one of skill in the art including, but not limited to, chromatography and centrifugation.

As used herein, the terms "subject" or "patient" are used interchangeably. As used herein, the terms "subject" and "subjects" refers to an animal (e.g., avians, reptiles, and mammals). In some embodiments, the subject is a mammal including a non-primate (e.g., a camel, donkey, zebra, cow, horse, horse, cat, dog, rat, and mouse) and a primate (e.g., a monkey, chimpanzee, and a human). In some embodiments, the subject is a non-human mammal. In other embodiments the subject is a human. In certain embodiments, the mammal (e.g., human) is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In a specific embodiment, the subject or patient is an avian. In certain embodiments, the avian is 0 to 3 months old, 3 to 6 months old, 6 to 9 months old, 9 to 12 months old, 12 to 15 months old, 15 to 18 months old, or 18 to 24 months old.

As used herein, the term "synergistic" in the context of the administration or the result or therapies, refers to a combination of therapies (e.g., prophylactic or therapeutic agents) which is more effective than the additive effects of any two or more single therapies (e.g., one or more prophylactic or therapeutic agents). A synergistic effect of a combination of therapies (e.g., a combination of prophylactic or therapeutic agents) permits the use of lower dosages of one or more of therapies (e.g., one or more prophylactic or therapeutic agents) and/or less frequent administration of said therapies to a subject with a disease (e.g., an influenza virus infection, an NDV infection or a condition or symptom associated therewith, or an infection other than an influenza virus infection, NDV infection or a condition or symptom associated therewith). The ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a disease (e.g., an influenza virus infection or a condition or symptom associated therewith, or an infection other than an influenza virus infection, NDV infection or a condition or symptom associated therewith). In addition, a synergistic effect can result in improved efficacy of therapies (e.g., prophylactic or therapeutic agents) in the prevention, management or treatment of a disease (e.g., an influenza virus infection, an NDV infection or a condition or symptoms associated therewith, or an infection other than an influenza virus infection, an NDV infection or a condition or symptom associated therewith). Finally, synergistic effect of a combination of therapies (e.g., prophylactic or therapeutic agents) may avoid or reduce adverse or unwanted side effects associated with the use of any single therapy.

As used herein, the terms "therapies" and "therapy" can refer to any protocol(s), method(s), and/or agent(s) that can be used in the prevention, treatment, management, or amelioration of a disease (e.g., cancer, an influenza virus infection, an NDV infection or a condition or symptom associated therewith, or an infection other than an influenza virus infection, or NDV infection or a condition or symptom associated therewith). In certain embodiments, the terms "therapies" and "therapy" refer to biological therapy, supportive therapy, and/or other therapies useful in treatment, management, prevention, or amelioration of a disease, an infection or a condition or symptom associated therewith, known to one of skill in the art.

As used herein, the terms "therapeutic agent" and "therapeutic agents" refer to any agent(s) which can be used in the prevention, treatment, management, or amelioration of a disease (e.g. an infection or a symptom thereof (e.g., an influenza infection, an NDV infection or a condition or symptoms associated therewith, an infection other than an influenza virus infection, NDV infection or a condition or symptom associated therewith)). Preferably, a therapeutic agent is an agent which is known to be useful for, or has been or is currently being used for the prevention, treatment, management, or amelioration of a disease or symptom associated therewith (e.g., an influenza infection, NDV infection or a condition or symptom associated therewith, an infection other than an influenza virus infection, NDV infection or a condition or symptom associated therewith).

As used herein, the terms "treat," "treatment," and "treating" in the context of administration of a therapy to a subject for a disease refers to the eradication, reduction or amelioration of symptoms of said disease. With respect to infections (e.g., influenza virus, or NDV virus), treatment refers to the eradication or control of the replication of an infectious agent (e.g., a virus), the reduction in the numbers of an infectious agent (e.g., the reduction in the titer of virus), the reduction or amelioration of the progression, severity, and/or duration of an infection (e.g., an influenza infection, NDV infection or a condition or symptoms associated therewith, an infection other than an influenza virus infection, NDV infection or a condition or symptom associated therewith), or the amelioration of one or more symptoms resulting from the administration of one or more therapies (including, but not limited to, the administration of one or more prophylactic or therapeutic agents). With respect to cancer, treatment refers to the eradication, removal, modification, or control of primary, regional, or metastatic cancer tissue that results from the administration of one or more therapeutic agents of the invention. In certain embodiments, such terms refer to the minimizing or delaying the spread of cancer resulting from the administration of one or more therapeutic agents of the invention to a subject with such a disease. In other embodiments, such terms refer to elimination of disease causing cells.

4. DESCRIPTION OF THE FIGURES

Figure 1:
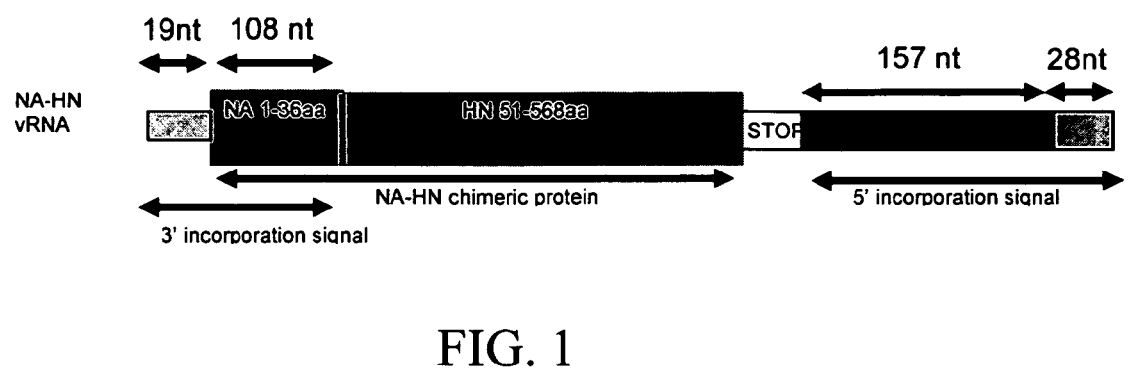

FIG. 1. Schematic Representation of a Hybrid NAf-HN Construct

The construct encodes nucleotides of the 3' noncoding region of the WSN NA vRNA, the NA coding region corresponding to the cytoplasmic tail and transmembrane domains of the NA protein plus the first amino acid of the NA ectodomain, the coding region of the NDV B1 HN protein (ectodomain only), two sequential stop codons, the untranslated nucleotides of the WSN NA reading frame and the 5' noncoding region of the WSN vRNA.

FIG. 2. Schematic Representation of Alteration in Polybasic Amino Acid Sequence of HA The nucleotide sequence identified as H5N1 HA represents nucleotides 1013-1045 (SEQ ID NO:13; amino acid sequence SEQ ID NO:14) of the open reading frame of the HA surface glycoprotein of Influenza A/Vietnam/1203/04 (H5N1). Nucleotides 1026-1038 were replaced by the single nucleotide cytosine using excise PCR and site directed mutagenesis resulting in the nucleotide sequence of avirulent HA (SEQ ID NO:15; amino acid sequence SEQ ID NO:16). The sequence change corresponds to the replacement of the polybasic sequence of 5 amino acids with the single amino acid threonine.

FIG. 3. Schematic Representation of Alteration in Nucleic Acid Sequence of HA The sequence identified as Avirulent HA represents nucleotides 1013-1033 of the open reading frame of an HA surface glycoprotein based on consensus sequences of the HA proteins of avirulent Influenza A/Vietnam/1203/04 (H5N1) (SEQ ID NO:15; amino acid sequence SEQ ID NO:16). Underlined adenosine residues were replaced such that mutations were synonymous resulting in the nucleotide sequence SEQ ID NO:17 and amino acid sequence SEQ ID NO:16.

FIG. 4A-D. Schematic of pPol1VN1203 NS Truncation Mutants

A. The coding region of NS gene segment of H5N1 is 833 nucleotides. B. The pPol1VN1203 NS1-126 construct has a deletion in the NS gene from nucleotides 379-456 of the coding region, the insertion of 3 stop codons and a BglII restriction site. C. The pPol1VN1203 NS1-99 construct has a deletion in the NS gene from nucleotides 298-456 of the coding region, the insertion of 4 stop codons, a BglII restriction site and a PacI restriction site. D. The pPol1VN1203 NS1-73 construct has a deletion in the NS gene from nucleotides 219-456 of the coding region, the insertion of 4 stop codons, a BglII restriction site and a Pad restriction site.

Figure 5:
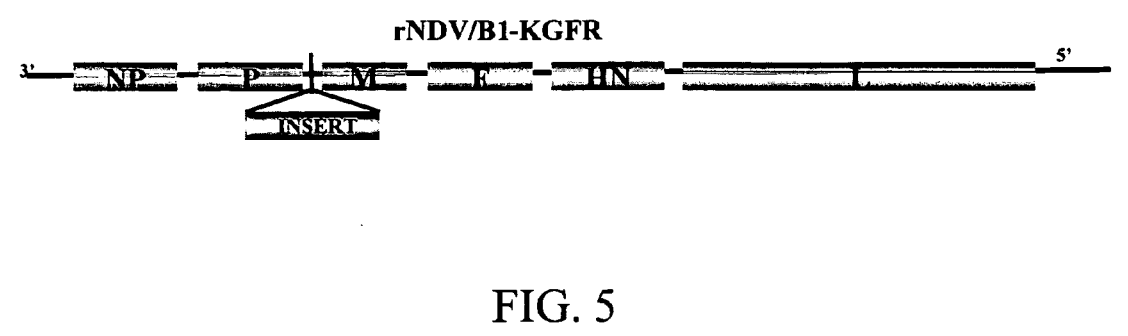

FIG. 5. Schematic of pNDV/B1

The sequence depicted are flanked at the 3' end by a T7 promoter and at the 5' end by a HDV ribozyme and T7 terminator. The insertion site between the P an M genes comprises a unique XbaI restriction site.

Figure 6:
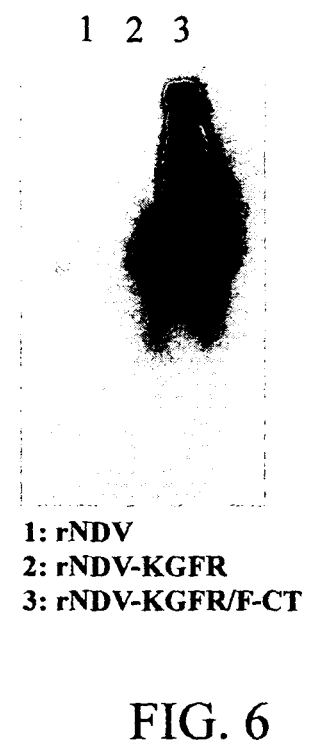

FIG. 6. Western Blot Analysis of KGFR Expression in Chimeric rNDV Viruses

The chimeric viruses rNDV (lane 1), rNDV-KGFR (lane 2) and rNDV-KGFR/F-CT (lane 3) were grown in 10-day old embryonated chicken eggs. Purified viruses subjected to Western blot analysis using a murine anti-KGFR and an anti-mouse HRPO as the primary and secondary antibodies, respectively.

Figure 7:
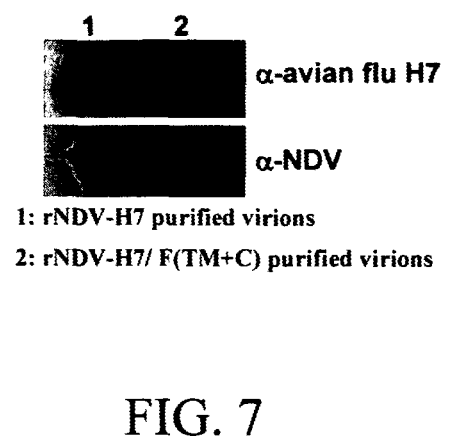

FIG. 7. Western Blot Analysis of H7 HA Expression in Chimeric rNDV Viruses

The chimeric viruses rNDV (lane 1), rNDV-KGFR (lane 2) and rNDV-KGFR/F-CT (lane 3) were grown in 10-day old embryonated chicken eggs. Purified viruses subjected to Western blot analysis using a murine anti-KGFR and an anti-mouse HRPO as the primary and secondary antibodies, respectively.

FIG. 8. Modification of the Cleavage Site of the F Protein of rNDV (A) Schematic representation of the rNDV/B1 genome with two or three amino acid changes in the cleavage site of their F proteins (corresponding to amino acids 112-117; native rNDV/B1 cleavage site, GRQGR/L; rNDV/F2aa, RRQRR/L; and rNDV/F3aa, RRQRR/F). The peptide bond that is cleaved in the F protein is indicated with a slash. (B) Syncytia formation in CEF cells infected by rNDVs with modified F proteins. CEF cells infected a multiplicity of infection of 0.001, with rNDV/B1, rNDV/F2aa, and rNDV/F3aa viruses. Viral spread was monitored every 24 hours by immunofluorescence assay.

FIG. 9. Construction and Characterization of the Fusogenic rNDV Vector Expressing HPAI H7 HA Protein.

(A) Schematic representation of rNDV/F3aa chimeric H7 cDNA construct, with the GE/GS, Kozak, and partial H7 HA sequences presented (SEQ ID NO:36). (B) Comparison of viral growth kinetics, Log TCID vs Time after Inoculation (hrs). Square, rNDV/B1; triangle, rNDV/F3aa; bold asterisk, rNDV/B1-H7; asterisk, rNDV/F3aa-chimericH7. (C) Expression of the WT H7 HA protein or the chimeric H7 HA protein in cells infected with rNDVs. Lane 1, mock infected; lane 2, rNDV/F3aa; lane 3, rNDV/B1-H7; lane 4, rNDV/F3α-chimericH7. Row 1 α-avian H7; row 2, α-NDV. (D) Incorporation of the chimeric H7 HA protein in rNDV virions was increased as compared to that of WT H7 HA protein. Lane 1, rNDV/B1-H7; rNDV/F3α-chimericH7. Row 1 α-avian H7; row 2, α-NDV.

5. DETAILED DESCRIPTION OF THE INVENTION

The present invention provides chimeric negative strand RNA viruses engineered to express fusion proteins that incorporate into the virion, methods for producing such chimeric viruses and the use of such viruses, for example as immunogens, in immunogenic formulations, or in in vitro assays. The chimeric viruses of the invention are characterized by displaying, on the surface of the virion, not only antigens associated with the virus but also the fusion protein.

The viruses that may be engineered in accordance with the methods of the invention can be any enveloped virus. In a specific embodiment, the viruses that may be engineered in accordance with the methods of the invention have segmented or non-segmented genomes, single stranded or double stranded genomes, and express at least one essential glycoprotein (e.g., NA, HA, HN or F) that is incorporated into the virial envelope. The viruses for use in accordance with the methods of the invention can be selected from naturally occurring strains, variants or mutants; mutagenized viruses (e.g., by exposure to UV irradiation, mutagens, and/or passaging); reassortants (for viruses with segmented genomes); and/or genetically engineered viruses. For example, the mutant viruses can be generated by natural variation, exposure to UV irradiation, exposure to chemical mutagens, by passaging in non-permissive hosts, by reassortment (i.e., by coinfection of an attenuated segmented virus with another strain having the desired antigens), and/or by genetic engineering (e.g., using "reverse genetics"). Non-limiting examples of viruses with segmented genomes for use in accordance with the methods of the invention include viruses from the family orthomyxoviridae (e.g., influenza viruses), bunyaviridae (e.g., Bunyamwera), reoviridae and arenaviridae (e.g., Lassa fever). Non-limiting examples of viruses with non-segmented genomes for use in accordance with the methods of the invention include coronaviridae (e.g., human corona virus (SARS)), hepadnaviridae (e.g. hepatitus A, B or C virus), herpesviridae (e.g. herpes simplex virus), poxyiridae (e.g., smallpox), rhabdoviridae (e.g., vesicular stomatitis virus (VSV), Sendai virus and rabies), paramyxoviridae (e.g., measles and respiratory syncytial virus), and filoviridae (Marburg and Ebola viruses). In certain embodiments, the segemented virus is influenza virus. In other embodiments the non-segmented virus is NDV.

In certain embodiments, the viruses selected for use in the invention are attenuated and/or have defective IFN antagonist activity; i.e., they are infectious and can replicate in vivo, but only generate low titers resulting in subclinical levels of infection that are non-pathogenic. The viruses may be attenuated by any method known in the art and/or exemplified herein, e.g., engineering the virus to comprise a mutation in the NS1 gene or to comprise a modification in the polybasic amino acid sequence before the cleavage site in the HA protein. Such attenuated viruses engineered in accordance with the invention are thus ideal candidates for immunogenic formulations, e.g., live virus vaccines. When administered to a subject, the attenuated, chimeric viruses of the invention are capable of generating an immune response and eliciting immunity to both the virus and to the non-native or fusion protein. In some embodiments, the non-native protein is derived from a pathogen. By extension, administration of such a chimeric virus to a subject generates an immune response and/or immunity to said pathogen in addition to the virus.

The invention also relates to the use of the chimeric virus of the invention in compositions (e.g. immunogenic formulations) for humans or animals (e.g., avians). In particular, the chimeric viruses that are attenuated can be used as vaccines against a broad range of virus and/or diseases. Because the chimeric virus is engineered to express heterologous gene sequences as foreign epitopes in the virion, compositions comprising a chimeric virus of the invention (e.g., vaccine formulations) can be designed for immunization against multiple strain variants, different viruses or against completely different infectious agents or disease antigens (e.g., bacteria, parasites, fungi or tumor specific antigens) from which the heterologous gene sequences are derived. Many methods may be used to introduce the live attenuated virus formulations to a human or animal subject to induce an immune or appropriate cytokine response. These include, but are not limited to, intranasal, intratrachial, oral, intradermal, intramuscular, intraperitoneal, intravenous and subcutaneous routes.

5.1 Chimeric Influenza Viruses

5.1.1 Chimeric Avian Influenza Virus Comprising a Fusion Protein Incorporated in its Virion The present invention encompasses the engineering of an avian influenza virus such that a fusion protein is encoded by the genome and, when expressed, is incorporated into the virion. Any avian influenza virus type, subtype or strain that can be engineered to express and incorporate the fusion protein into the avian influenza virion can be selected and used in accordance with the invention including, but not limited to, naturally occurring strains, variants or mutants, mutagenized viruses, reassortants and/or genetically engineered viruses. In a specific embodiment, the avian influenza viruses of the invention are not naturally occurring viruses. In another specific embodiment, the avian influenza viruses of the invention are genetically engineered viruses. Non-limiting examples of avian influenza viruses include Influenza A subtype H5N1, H6N2, H7N3, H9N2 and H10N7.

Genetic manipulation of the influenza virus requires engineering at least one of the eight viral RNA segments which comprise the viral genome. Mutagenesis of the genome may be achieved through "reverse engineering" techniques (see section 5.4). The plasticity of the influenza genome is, however, limited both in the number of segments and in the length of segments that may be stably integrated into the virus. The overall stability of long inserts is unknown and the segments comprising such inserts, or portions thereof, may be lost due to viral assortment after a few generations. Thus, in a preferred embodiment of the invention, the avian influenza virus is engineered such that one of its two major surface proteins is replaced by a fusion protein.

Accordingly, the present invention provides a chimeric avian influenza virus, comprising at least one fusion protein comprising an ectodomain (ED) of a protein of infectious agent other than an influenza virus and the cytoplasmic (CT) and transmembrane (TM) domains or the transmembrane (TM) domain of at least one essential influenza virus glycoprotein, wherein the at least one fusion protein functionally replaces at least one essential avian influenza virus glycoprotein. In other words, the avian influenza virus serves as the "backbone" that is engineered to express and incorporate into its virion the fusion protein in place of an essential avian influenza virus glycoprotein. The inclusion of the TM and CT domains or TM domain of an influenza virus glycoprotein corresponding to the essential avian influenza virus glycoprotein functionally replaced by the fusion protein permits the fusion protein to incorporate into the virion of the avian influenza virus. The TM and CT domains or TM domain of the fusion protein may correspond to or be derived from any influenza virus that permits the fusion protein to incorporate into the virion of the avian influenza virus backbone.

In certain embodiments, the TM and CT domains or the TM domain of the fusion protein correspond to the TM and CT domains or the TM domain of a different type, subtype or strain of avian influenza virus than the backbone avian influenza virus. In other embodiments, the TM and CT domains or the TM domain of the fusion protein correspond to the TM and CT domains or the TM domain of an influenza virus other than an avian influenza virus. In other embodiments, the TM and CT domains or the TM domain of the fusion protein correspond to the TM and CT domains or the TM domain of the avian influenza virus backbone.

The avian influenza virion comprises two major surface glycoproteins, hemagglutinin (HA) and neuraminidase (N), both of which comprise a cytoplasmic domain, a transmembrane domain and an ectodomain. Accordingly, in certain embodiments, the TM and CT domains of the fusion protein correspond to the TM and CT domains of either an HA protein or an NA protein of an influenza virus. Since the CT domain of HA or NA may not be necessary for incorporation of the fusion protein into the avian influenza virus virion, the fusion protein, in some embodiments, is engineered to contain only the TM domain of HA or NA. For example, the CT domain of NA has been shown to be unnecessary for the proper packaging of this protein into influenza A viral envelopes (Garcia-Sastre et al., 1995, Virus Res. 37:37-47, which is hereby incorporated by reference in its entirety). Therefore, where structural domains corresponding to those of an NA protein are used in the creation of the fusion protein, the invention encompasses engineering the fusion protein to contain only a TM domain corresponding to an influenza virus NA protein. Accordingly, in one embodiment of the invention, the fusion protein is engineered to contain only a TM domain, which TM domain corresponds to the TM domain of an influenza virus NA protein.

The TM and CT domains of influenza virus HA and NA proteins are structurally distinct in that the domains are located at the C-terminus of the HA protein and the N-terminus of the NA protein. Apart from the differing orientation of the two domains in each class of surface glycoprotein, the HA and CT structural domains may comprise yet unknown differences in functionality dependent on their relative placement within a polypeptide chain. Therefore, when designing the fusion protein to be engineered into the avian influenza virus, the orientation of the ectodomain of the infectious agent to be fused to the TM and CT domains or the TM domain of an influenza virus glycoprotein will guide the selection of the TM and CT domains or the TM domain. For example, where the ectodomain of an infectious agent is anchored by the N-terminus, the TM and CT domains of an influenza virus NA protein may used.

HA and NA exhibit competing activities with respect to cellular fusion and release, respectively, that are necessary for the infectivity and propagation of the virus. HA binds to N-AcetylNeuraminic Acid (NeuNAc; sialic acid) on a cell surface leading to uptake of the virus by a host cell, while NA cleaves sialic acid moieties from the cell surface leading to release of progeny virus from an infected cell. Disruption of either of these activities results in a non-functional virus. Accordingly, to maintain viral competence, where a surface glycoprotein is replaced, its function in the chimeric virus must be supplied by the fusion protein. In one embodiment of the invention, the chimeric avian influenza virus comprises a fusion protein that exhibits neuraminidase activity. In another embodiment of the invention, the chimeric avian influenza virus comprises a fusion protein that exhibits receptor binding activity. In yet another embodiment of the invention, the chimeric avian influenza virus comprises two fusion proteins one of which exhibits neuraminidase activity, the other of which exhibits receptor binding activity. In still other embodiments, the chimeric avian influenza virus comprises a fusion protein comprising an epitope of a heterologous infectious agent, which fusion protein exhibits exhibits neuraminidase activity or receptor binding activity. In another embodiment of the invention, the chimeric avian influenza virus comprises a fusion protein that exhibits receptor binding activity. In a specific embodiment, the chimeric avian influenza virus comprises a surface protein containing the ectodomain of the HN protein of Newcastle Disease Virus (NDV) and the TM and CT domains of the NA protein of Influenza A/WSN/33, which HN ectodomain exhibits neuraminidase activity. In other embodiments, the chimeric avian influenza virus comprises a surface protein containing the ectodomain of the HA protein of a heterologous influenza virus (e.g., the H7 HA protein or H9 HA protein). HA and NA are encoded by separate segments of the viral genome and replacement of the entire coding region of the native protein eliminates most length constraints on the sequence encoding the introduced protein.

In certain embodiments, the fusion protein comprises the transmembrane domain plus 1 to 15, 1 to 10, 1 to 5, 1 to 3, 2 or 1 immediately adjacent residue(s) of the ectodomain of an essential influenza virus glycoprotein. For example, in a specific embodiment, the fusion protein comprises the transmembrane domain of an influenza virus NA protein, 1 to 15, 1 to 10, 1 to 5, 1 to 3, 2 or 1 immediately adjacent residue(s) of the ectodomain of the influenza virus NA protein, and the ectodomain, or fragment thereof, of an infectious agent other than influenza virus such that the fusion protein can functionally replace the function of NA protein. In another specific embodiment, the fusion protein comprises the cytoplasmic and transmembrane domains of an influenza virus NA protein, 1 to 15, 1 to 10, 1 to 5, 1 to 3, 2 or 1 residue(s) of the ectodomain of the influenza virus NA protein that are immediately adjacent to the transmembrane domain of the influenza virus NA protein, and the ectodomain, or fragment thereof, of an infectious agent other than influenza virus such that the fusion protein can functionally replace the NA protein. In another embodiment, the fusion protein comprises the transmembrane domain or cytoplasmic and transmembrane domains of an NA protein, the complete stalk domain, or a fragment thereof, of an NA protein that precedes its globular head, and the ectodomain, or fragment thereof, of an infectious agent other than influenza virus such that the fusion protein can functionally replace the function of NA protein. In another specific embodiment, the fusion protein comprises the transmembrane domain of an influenza virus HA protein, 1 to 15, 1 to 10, 1 to 5, 1 to 3, 2 or 1 immediately adjacent residue(s) of the ectodomain of the influenza virus HA protein, and the ectodomain, or fragment thereof, of an infectious agent other than influenza virus such that the fusion protein can functionally replace the function of HA protein. In another specific embodiment, the fusion protein comprises the cytoplasmic and transmembrane domains of an influenza virus HA protein, 1 to 15, 1 to 10, 1 to 5, 1 to 3, 2 or 1 residue(s) of the ectodomain of the influenza virus HA protein that are immediately adjacent to the transmembrane domain of the influenza virus HA protein, and the ectodomain, or fragment thereof, of an infectious agent other than influenza virus such that the fusion protein can functionally replace the HA protein.

In certain embodiments, the at least one fusion protein of the chimeric avian influenza virus of the invention does not comprise the complete ectodomain of a heterologous protein (e.g., comprises an antigenic fragment of the ectodomain of a protein of a heterologous infectious agent), and may or may not further comprise one or more fragments of the ectodomain of a native essential glycoprotein. Accordingly, in certain embodiments, the ectodomain of the fusion protein may comprise a fragment of the ectodomain of a protein of a heterologous infectious agent. In other embodiments, the ectodomain of the fusion protein may comprise fragments of both a native essential glycoprotein and a protein of a heterologous infectious agent. In embodiments where the fusion protein replaces an essential surface glcoprotein, the function of the surface glycoprotein must be supplied by the fusion protein, i.e., the fusion protein must exhibit the functionality of the surface glycoprotein that it is replacing.

The present invention encompasses nucleotide sequences (i.e., recombinant segments) encoding the fusion proteins described in this Section 5.1.1. In preferred embodiments, the recombinant segments comprising nucleic acids encoding the fusion proteins described in Section 5.1.1 comprise 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a preferred embodiment, the recombinant segments of the invention therefore use the 3' and 5' noncoding and/or nontranslated sequences of segments of viruses within the same viral type or strain as the backbone avian influenza virus. In specific embodiments, the recombinant segments comprise nucleic acids encoding the fusion proteins described in this Section, 5.1.1, which comprise the 3' noncoding region of an influenza virus NA vRNA, the NA coding region corresponding to the CT and TM domains of the NA protein, 1 to 15, 1 to 10, 1 to 5, 1 to 3, 2 or 1 residue(s) of the ectodomain of the influenza virus NA protein that are immediately adjacent to the transmembrane domain of the influenza virus NA protein, the untranslated regions of the NA protein reading frame and the 5' non-coding region of the NA vRNA.

As an alternative to replacing the NA or HA proteins of avian influenza virus, "reverse genetic" and bicistronic techniques may be used to produce a chimeric influenza virus comprising an ectodomain, or a fragment thereof, of a protein of an infectious agent other than influenza virus and the TM and/or CT domains of an influenza virus. See, e.g., U.S. Pat. No. 6,887,699, U.S. Pat. No. 6,001,634, U.S. Pat. No. 5,854,037 and U.S. Pat. No. 5,820,871, each of which is hereby incorporated by reference in its entirety. The bicistronic approaches involve inserting the coding region of the fusion protein into the open reading frame of a necessary protein of the virus and its stop codon. The insertion is flanked by an IRES and any untranslated signal sequences of the necessary protein in which it is inserted and must not disrupt the open reading frame, packaging signal, polyadenylation or transcriptional promoters of the necessary viral protein. Any IRES well known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238). Since the function of HA or NA is not being replaced when the bicistronic approach is used, the ectodomain portion of the fusion protein is not limited to a protein that provides the function of the replaced HA or NA protein. The ectodomain of such a fusion protein may correspond to any heterologous molecule, or comprise a fragment of any heterologous molecule, including but not limited to antigens, disease antigens and antigens derived from any protein of an infectious agent (e.g. any protective antigen associated with viral, bacterial or parasitic infectious agents). Non-limiting examples of antigens derived from or associated with infectious agents for use in accordance with the methods of the invention are provided in Section 5.3, infra.

Replacement of a necessary surface protein of the backbone virus or introduction of a recombinant segment into the viral genome may attenuate the resulting chimeric virus, i.e., the chimeric virus will exhibit impaired replication relative to wild type. In certain embodiments of the invention, attenuation of the chimeric virus is desired such that the chimeric virus remains, at least partially, infectious and can replicate in vivo, but only generate low titers resulting in subclinical levels of infection that are non-pathogenic. Such attenuated chimeric viruses are especially suited for embodiments of the invention wherein the virus is administered to a subject in order to act as an immunogen, e.g., a live vaccine. The viruses may be attenuated by any method known in the art and/or exemplified herein, e.g., engineering the virus to comprise a mutation in the NS1 gene or to comprise a modification in the polybasic amino acid sequence before the cleavage site in the HA protein (see U.S. Pat. No. 6,468,544; U.S. Pat. No. 6,669,943; Li et al., 1999, J. Infect. Dis. 179:1132-1138, each of which is hereby incorporated by reference in its entirety).

In one embodiment, an attenuated chimeric avian influenza virus of the invention comprises a genome comprising a mutation in the NS1 gene of the avian influenza backbone virus, which is known in other influenza viruses to diminish the ability of the NS1 gene product to antagonize a cellular interferon response. In another embodiment, an attenuated chimeric avian influenza virus of the invention comprises a genome comprising a mutation in the HA gene of the avian influenza backbone virus, which is known in other influenza viruses to diminish or eliminate the ability of cellular proteases to cleave the protein into its active form and thereby reduce or eliminate HA induced fusion and infectivity. In yet another embodiment, an attenuated chimeric avian influenza virus of the invention comprises a genome comprising a mutation in both the HA gene and NS1 gene of the avian influenza backbone virus, which are known in other influenza viruses to either separately or when combined to reduce or diminish viral activity. The titers of attenuated-chimeric and wild-type avian influenza viruses can be determined utilizing any technique well-known in the art or described herein, (e.g., hemagglutination assays, plaque assays, egg infectious doses (EID50), tissue culture infectious dose (TCID50), etc.) and the viruses can be propagated under conditions described herein or well-known in the art (e.g., in CEF cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., CEF cells, MDCK cells, etc.) that are grown in serum-free or serum reduced (e.g., TPCK trypsin) medium.

5.1.2 Chimeric Attenuated Influenza Virus Comprising a Fusion Protein Incorporated in its Virion The present invention encompasses the engineering of an attenuated influenza virus such that a fusion protein is encoded by the genome and, when expressed, is incorporated into the virion. In other words, the invention encompasses the use of an attenuated influenza virus (the parental virus) as the "backbone" that is engineered to express and incorporate into its virion the fusion protein. Any attenuated influenza virus type or strain including, but not limited to, naturally occurring strains, variants or mutants, mutagenized viruses, reassortants and/or genetically modified viruses may be used as the backbone of that is engineered to express and incorporate into its virion the fusion protein. In a specific embodiment, the parental influenza viruses for use in accordance with the invention are not naturally occurring viruses. In another specific embodiment, the parental influenza viruses for use in accordance with the invention are genetically engineered viruses.

Influenza viruses for use as the backbone virus in accordance with the invention may naturally have an attenuated phenotype or may be engineered to comprise a mutation associated with an attenuated phenotype, where such mutation is known in the art or described herein (e.g. a mutation in the viral NS1 protein or viral HA protein). In specific embodiments, the attenuated virus is influenza A. In other embodiments, the attenuated virus is influenza B. In yet other embodiments, the attenuated virus is influenza C. Nonlimiting examples of influenza viruses which may be engineered in accordance with the invention include Influenza A subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, or subtype H9N9; Influenza B strain Aichi/5/88, strain Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV 106/2002, strain Belgium/WV 107/2002, strain Belgium/WV 109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV 187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, or strain Rochester/02/2001; Influenza C strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, or strain STRAIN C/YAMAGATA/10/81.

In one embodiment, the attenuated influenza virus (the parental virus) used in accordance with the invention has an impaired ability to antagonize the cellular interferon (IFN). In a specific embodiment, the attenuated influenza virus (the parental virus) used in accordance with the invention is an influenza virus type or strain comprising a mutation in the NS1 gene that results in an impaired ability of the virus to antagonize the cellular interferon response. Examples of the types of mutations that can be introduced into the influenza virus NS1 gene include deletions, substitutions, insertions and combinations thereof. One or more mutations can be introduced anywhere throughout the NS1 gene (e.g., the N-terminus, the C-terminus or somewhere in between) and/or the regulatory element of the NS1 gene. In a specific embodiment, an attenuated influenza virus (the parental virus) used in accordance with the invention comprises a genome having an influenza virus NS1 gene with a mutation at the N-terminus. In another embodiment, an attenuated influenza virus (the parental virus) comprises a genome having an influenza virus NS1 gene with a mutation at the C-terminus. In another embodiment, an attenuated influenza virus (the parental virus) used in accordance with the invention comprises a genome having a mutation in an influenza virus NS1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated influenza virus (the parental virus) used in accordance with the invention comprises a genome having a mutation in an influenza virus NS1 gene resulting in a deletion of all amino acid residues except amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-80, amino acid residues 1-75, amino acid residues 1-73, amino acid residues 1-70, amino acid residues 1-65 or amino acid residues 1-60, wherein the N-terminus amino acid is number 1.

In one embodiment, an attenuated influenza virus of the invention comprises a genome comprising a mutation in the NS1 gene of the influenza virus backbone, which diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than the wild-type influenza virus in cells (e.g., cells of human, mouse, rat, porcine, dog, horse, or avian origin (e.g., HEp-2, A549, 293T, Madin-Darby canine kidney cells (MDCK) or chicken embryo fibroblasts (CEF)), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in CEF cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., CEF cells, MDCK cells, etc.) that are grown in serum-free or serum reduced (e.g., TPCK trypsin) medium.

In another embodiment, the attenuated influenza virus (the parental virus) used in accordance with the invention comprises a genome comprising a mutation in the HA gene of the influenza backbone virus that diminishes or eliminates the ability of cellular proteases to cleave the protein into its active form. Examples of the types of mutations that may be introduced into the influenza HA gene include deletions, substitutions, insertions or combinations thereof. The one or more mutations are preferably introduced at the HA cleavage site (e.g., nucleotides 1013-1039 of GenBank entry AY818135). In general, mutations which decrease the cleavability of the HA protein as determined by standard methods in CEF correlate with decreased virulence in in vivo assays (Horimoto and Kawaoka, 1994, 68:3120-3128; which is hereby incorporated by reference in its entirety). In a specific embodiment, an attenuated influenza virus (the parental virus) used in accordance with the invention comprises a genome having a mutation in the influenza virus HA gene resulting in the substitution of nucleotides 1026-1038 with the single nucleotide thymine. In another embodiment, an attenuated influenza virus of the invention comprises a genome comprising a mutation in the HA gene of the influenza backbone virus that diminishes or eliminates the ability of cellular proteases to cleave the protein into its active form, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than the wild-type influenza virus in cells (e.g., cells of human, mouse, rat, porcine, dog, horse, or avian origin (e.g., HEp-2, A549, 293T, Madin-Darby canine kidney cells (MDCK) or chicken embryo fibroblasts (CEF)), as determined approximately 2 to 10 days, 3 to 7 days, 3 to 5 days, or 2, 3, 4, 5, 6, 7, 8, 9, 10 days post-infection when propagated under the same conditions. The HA protein comprising such a mutation is not antigenically distinct from the wild-type parental HA protein, i.e., all antibodies raised against the wild-type HA protein will cross react with the mutated HA protein and all antibodies raised against the mutated HA protein will cross react with the wild-type HA protein. The titers of attenuated and wild-type influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in CEF cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., CEF cells, MDCK cells, etc.) that are grown in serum-free or serum reduced (e.g., TPCK trypsin) medium.

In another embodiment, the attenuated influenza virus (the parental virus) used in accordance with the invention comprises a genome comprising: (i) a mutation in the HA gene of the influenza backbone virus that diminishes or eliminates the ability of cellular proteases to cleave the protein into its active form, and (ii) a mutation in the NS1 gene that results in an impaired ability of the virus to antagonize the cellular interferon response. In another embodiment, an attenuated influenza virus of the invention comprises a genome comprising a mutation in both the HA gene and NS1 gene of the influenza backbone virus that permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than the wild-type influenza virus in cells (e.g., cells of human, mouse, rat, porcine, dog, horse, or avian origin (e.g., HEp-2, A549, 293T, Madin-Darby canine kidney cells (MDCK) or chicken embryo fibroblasts (CEF)), as determined approximately 2 to 10 days, 3 to 7 days, 3 to 5 days, or 2, 3, 4, 5, 6, 7, 8, 9, 10 days post-infection when propagated under the same conditions.

The present invention provides a chimeric attenuated influenza virus, comprising at least one fusion protein having an ectodomain (ED), or fragment thereof, of an infectious agent other than an influenza virus and the cytoplasmic (CT) and transmembrane (TM) domains or the transmembrane domain of an essential influenza virus glycoprotein, wherein the at least one fusion protein functionally replaces at least one essential influenza virus glycoprotein. In other words, the attenuated influenza virus serves as the "backbone" that is engineered to express and incorporate into its virion the at least one fusion protein in place of an essential influenza virus glycoprotein. The inclusion of the TM and CT domains or TM domain of an influenza virus glycoprotein corresponding to the essential influenza virus glycoprotein functionally replaced by the fusion protein permits the fusion protein to incorporate into the virion of the attenuated influenza virus. The TM and CT domains or TM domain of the fusion protein may correspond to or be derived from any influenza virus that permits the fusion protein to incorporate into the virion of the attenuated influenza virus backbone.

In certain embodiments, the TM and CT domains or the TM domain of the fusion protein correspond to the TM and CT domains or the TM domain of a different type, subtype or strain of influenza virus than the backbone attenuated influenza virus. In other embodiments, the TM and CT domains or the TM domain of the fusion protein correspond to the TM and CT domains or the TM domain of an influenza virus of a species other than the backbone attenuated influenza virus. In preferred embodiments, the TM and CT domains or the TM domain of the fusion protein correspond to the TM and CT domains or the TM domain of the attenuated influenza virus backbone.

In certain embodiments, the TM and CT domains of the fusion protein correspond to the TM and CT domains of either an HA protein or an NA protein of an influenza virus. Since the CT domain of HA or NA may not be necessary for incorporation of the fusion protein into the influenza virus virion, in some embodiments, the fusion protein is engineered to contain only the TM domain of HA or NA.

The TM and CT domains of influenza virus HA and NA proteins are structurally distinct in that the domains are located at the C-terminus of the HA protein and the N-terminus of the NA protein. Apart from the differing orientation of the two domains in each class of surface glycoprotein, the HA and CT structural domains may comprise yet unknown differences in functionality dependent on their relative placement within a polypeptide chain. Therefore, when designing the fusion protein to be engineered into the attenuated influenza virus, the orientation of the ectodomain, or fragment thereof, of the infectious agent to be fused to the TM and CT domains or the TM domain of an influenza virus glycoprotein will guide the selection of the TM and CT domains or the TM domain.

To maintain viral competence, where a surface glycoprotein is replaced, its function in the chimeric virus must be supplied by the fusion protein. In one embodiment of the invention, the chimeric attenuated influenza virus comprises a fusion protein that exhibits neuraminidase activity. In another embodiment of the invention, the chimeric attenuated influenza virus comprises a fusion protein that exhibits receptor binding activity. In another embodiment of the invention, the chimeric attenuated virus comprises two fusion proteins, one of which exhibits neuraminidase activity and the other of which exhibits receptor binding activity. In still other embodiment of the invention, the chimeric attenuated influenza virus comprises a fusion protein comprising a fragment of a protein of a heterologous infectious agent, which fusion protein exhibits neuraminidase activity or receptor binding activity. In a specific embodiment, the chimeric attenuated influenza virus comprises a surface protein containing the ectodomain of the HN protein of Newcastle Disease Virus (NDV) and the TM and CT domains of the NA protein of Influenza A/WSN/33, which HN ectodomain exhibits neuraminidase activity. In other embodiments, the chimeric attenuated influenza virus comprises a fusion protein containing the ectodomain of the HA protein of a heterologous influenza subtype or strain (e.g., the ectodomain of 1-17 HA or ectodomain of 1-19 HA).

In certain embodiments, the at least one fusion protein of the chimeric attenuated influenza virus of the invention does not comprise the complete ectodomain of a heterologous protein (e.g., comprises an antigenic or protective fragment of the ectodomain of a protein of a heterologous infectious agent), and may or may not further comprise one or more fragments of the ectodomain of a native essential glycoprotein. Accordingly, in certain embodiments, the ectodomain of the fusion protein may comprise a fragment of the ectodomain of a protein of a heterologous infectious agent. In other embodiments, the ectodomain of the fusion protein may comprise fragments of both a native essential glycoprotein and a protein of a heterologous infectious agent. In embodiments where the fusion protein replaces an essential surface glcoprotein, the function of the surface glycoprotein must be supplied by the fusion protein, i.e., the fusion protein must exhibit the functionality of the surface glycoprotein that it is replacing.

The ectodomain of the fusion proteins described in this Section 5.1.2 may correspond to or be derived from any glcyoprotein, or fragment thereof, of an infectious agent (including, viral, bacterial and parasitic infectious agents). Non-limiting examples of infectious agent glycoproteins are provided in Section 5.3, infra.

In certain embodiments, the fusion protein comprises the transmembrane domain plus 1 to 15, 1 to 10, 1 to 5, 1 to 3, 2 or 1 immediately adjacent residue(s) of the ectodomain of an essential influenza virus glycoprotein. In a specific embodiment, the fusion protein comprises the transmembrane domain of an influenza virus NA protein, 1 to 15, 1 to 10, 1 to 5, 1 to 3, 2 or 1 immediately adjacent residue(s) of the ectodomain of the influenza virus NA protein, and the ectodomain, or fragment thereof, of an infectious agent other than influenza virus such that the fusion protein can functionally replace the function of NA protein. In another specific embodiment, the fusion protein comprises the cytoplasmic and transmembrane domains of an influenza virus NA protein, 1 to 15, 1 to 10, 1 to 5, 1 to 3, 2 or 1 residue(s) of the ectodomain of the influenza virus NA protein that are immediately adjacent to the transmembrane domain of the influenza virus NA protein, and the ectodomain, or fragment thereof, of an infectious agent other than influenza virus such that the fusion protein can functionally replace the NA protein. In another embodiment, the fusion protein comprises the transmembrane domain or cytoplasmic and transmembrane domains of an NA protein, the complete stalk domain, or a fragment thereof, of an NA protein that precedes its globular head, and the ectodomain, or fragment thereof, of an infectious agent other than influenza virus such that the fusion protein can functionally replace the function of NA protein. In another specific embodiment, the fusion protein comprises the transmembrane domain of an influenza virus HA protein, 1 to 15, 1 to 10, 1 to 5, 1 to 3, 2 or 1 immediately adjacent residue(s) of the ectodomain of the influenza virus HA protein, and the ectodomain, or fragment thereof, of an infectious agent other than influenza virus such that the fusion protein can functionally replace the function of HA protein. In another specific embodiment, the fusion protein comprises the cytoplasmic and transmembrane domains of an influenza virus HA protein, 1 to 15, 1 to 10, 1 to 5, 1 to 3, 2 or 1 residue(s) of the ectodomain of the influenza virus HA protein that are immediately adjacent to the transmembrane domain of the influenza virus HA protein, and the ectodomain, or fragment thereof, of an infectious agent other than influenza virus such that the fusion protein can functionally replace the HA protein.

The present invention encompasses nucleotide sequences (i.e., recombinant segments) encoding the fusion proteins described in this Section 5.1.2. In preferred embodiments, the recombinant segments comprising nucleic acids encoding the fusion proteins described in Section 5.1.2 comprise 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a preferred embodiment, the recombinant segments of the invention therefore use the 3' and 5' noncoding and/or nontranslated sequences of segments of viruses within the same viral type or strain as the backbone attenuated influenza virus. In specific embodiments, the recombinant segments comprise nucleic acids encoding the fusion proteins described in Section 5.1.2 that comprise the 3' noncoding region of an influenza virus NA vRNA, the NA coding region corresponding to the CT and TM domains of the NA protein, 1 to 15, 1 to 10, 1 to 5, 1 to 3, 2 or 1 residue(s) of the ectodomain of the influenza virus NA protein that are immediately adjacent to the transmembrane domain of the influenza virus NA protein, the untranslated regions of the NA protein reading frame and the 5' non-coding region of the NA vRNA. In certain embodiments, the recombinant segments comprise nucleic acids encoding the fusion proteins described in Section 5.1.2 that comprise the complete stalk domain, or fragment thereof, of an NA protein that precedes its globular head.

As an alternative to replacing the NA or HA proteins of an attenuated influenza virus, "reverse genetic" and bicistronic techniques may be used to produce a chimeric influenza virus comprising an ectodomain of an infectious agent other than influenza virus or a disease antigen and the TM and/or CT domains of an influenza virus. See, e.g., U.S. Pat. No. 6,887,699, U.S. Pat. No. 6,001,634, U.S. Pat. No. 5,854,037 and U.S. Pat. No. 5,820,871, each of which is hereby incorporated by reference in its entirety. Non-limiting examples of heterologous molecules such as disease antigens and antigens derived from an infectious agent that may be used in accordance with the methods of the invention (e.g. antigens associated with a disease or viral proteins) are provided in section 5.3, infra.

5.1.3 Chimeric Avian Influenza Viruses Comprising the Ectodomain of the HN Protein of Newcastle Disease Virus The present invention encompasses the engineering of an avian influenza virus such that a fusion protein comprising the ectodomain of the HN protein of Newcastle Disease virus is encoded by the genome and, when expressed, is incorporated into the virion. Any avian influenza virus type or strain that can be engineered to express and incorporate the fusion protein into the avian influenza virion can be selected and used in accordance with the invention including, but not limited to, naturally occurring strains, variants or mutants, mutagenized viruses, reassortants and/or genetically engineered viruses. Non-limiting examples of avian influenza viruses include Influenza A subtype H5N1, H6N2, H7N3, H9N2 or H10N7.

The present invention provides a chimeric avian influenza virus, comprising a fusion protein having an ectodomain (ED) of a Newcastle Disease virus (NDV) HN protein and the cytoplasmic (CT) and transmembrane (TM) domains or the transmembrane domain of an influenza virus NA protein, wherein the fusion protein functionally replaces the avian influenza virus NA protein. In other words, the avian influenza virus serves as the "backbone" that is engineered to express and incorporate into its virion the fusion protein in place of the avian influenza virus NA protein. The inclusion of the TM and CT domains or TM domain of an influenza virus NA protein in the fusion protein permits the fusion protein to incorporate into the virion of the avian influenza virus. The TM and CT domains or TM domain of the fusion protein may correspond to or be derived from any influenza virus that permits the fusion protein to incorporate into the virion of the avian influenza virus backbone.

The coding sequences of the TM and CT domains for use in accordance with the invention may be obtained or derived from the published sequence of any NA protein from any influenza strain or subtype (e.g., GenBank entry AY651447, from strain A/Viet Nam/1203/2004(H5N1); GenBank entry AY96877, from strain A/turkey/Canada/63 (H6N2); GenBank entry AY706954, from strain A/duck/Hainan/4/2004

(H6N2); GenBank entry AY646080, from strain A/chicken/British Columbia/GSC_human_B/04 (H7N3); or GenBank entry DQ064434, from strain A/chicken/Beijing/8/98 (H9N2)). In certain embodiments, the TM and CT domains or the TM domain of the fusion protein correspond to the TM and CT domains or the TM domain of a different type or strain of avian influenza virus than the backbone avian influenza virus. In other embodiments, the TM and CT domains or the TM domain of the fusion protein correspond to the TM and CT domains or the TM domain of an influenza virus other than an avian influenza virus. In preferred embodiments, the TM and CT domains or the TM domain of the fusion protein correspond to the TM and CT domains or the TM domain of the avian influenza virus backbone. In a specific embodiment, TM and CT domains of the fusion protein correspond to the TM and CT domains of the NA protein of Influenza A/WSN/33.

In certain embodiments, the fusion protein comprises the transmembrane domain of an influenza virus NA protein, 1 to 15, 1 to 10, 1 to 5, 1 to 3, 2 or 1 immediately adjacent residue(s) of the ectodomain of the influenza virus NA protein, and the ectodomain of a NDV HN protein. In another specific embodiment, the fusion protein comprises the cytoplasmic and transmembrane domains of an influenza virus NA protein, 1 to 15, 1 to 10, 1 to 5, 1 to 3, 2 or 1 residue(s) of the ectodomain of the influenza virus NA protein that are immediately adjacent to the transmembrane domain of the influenza virus NA protein, and the ectodomain of a NDV HN protein. In another specific embodiment, the fusion protein comprises the complete stalk domain, or a fragment thereof, of an NA protein that precedes its globular head and the ectodomain of a NDV HN protein. In other specific embodiments, the fusion protein comprises the transmembrane domain or cytoplasmic and transmembrane domains of an NA protein, and further comprises the complete stalk domain, or a fragment thereof, of an NA protein that precedes its globular head and the ectodomain of a NDV HN protein.

As an alternative to replacing the NA protein of avian influenza virus, "reverse genetic" and bicistronic techniques may be used to produce a chimeric avian influenza virus comprising an ectodomain of a NDV HN protein and the TM and/or CT domains of an influenza virus. See, e.g., U.S. Pat. No. 6,887,699, U.S. Pat. No. 6,001,634, U.S. Pat. No. 5,854,037 and U.S. Pat. No. 5,820,871, each of which is hereby incorporated by reference in its entirety.

The present invention encompasses nucleotide sequences (i.e., recombinant segments) encoding the fusion proteins described in this Section 5.1.3. In preferred embodiments, the recombinant segments comprising nucleic acids encoding the fusion proteins described in Section 5.1.3 comprise 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a preferred embodiment, the recombinant segments of the invention therefore use the 3' and 5' noncoding and/or nontranslated sequences of segments of viruses within the same viral type or strain as the backbone avian influenza virus. In specific embodiments, the recombinant segment comprises nucleic acids encoding the fusion proteins described in Section 5.1.3 comprise the 3' noncoding region of an influenza virus NA vRNA, the NA coding region corresponding to the CT and TM domains of the NA protein, 1 to 15, 1 to 10, 1 to 5, 1 to 3, 2 or 1 residue(s) of the ectodomain of the influenza virus NA protein that are immediately adjacent to the transmembrane domain of the influenza virus NA protein, the untranslated regions of the NA protein reading frame and the 5' non-coding region of the NA vRNA. In another specific embodiment, a recombinant segment comprises, 3' to 5' order, the 3' noncoding region of the WSN NA vRNA (19 nucleotides), nucleotides encoding amino acid residues 1-36 (108 nucleotides) of the NA coding region, nucleotides encoding amino acid residues 51-568 of the NDV B1 HN protein, two sequential stop codons, 157 nucleotides of the WSN NA untranslated reading frame, and the 5' noncoding region of the WSN vRNA (28 nucleotides). See FIG. 1.

Replacement of the NA protein of the backbone influenza virus or introduction of a recombinant segment into the viral genome may attenuate the resulting chimeric virus, i.e., the chimeric virus will exhibit impaired replication relative to wild type. In certain embodiments of the invention, attenuation of the chimeric virus is desired such that the chimeric virus remains, at least partially, infectious and can replicate in vivo, but only generate low titers resulting in subclinical levels of infection that are non-pathogenic. Such attenuated chimeric viruses are especially suited for embodiments of the invention wherein the virus is administered to a subject in order to act as an immunogen, e.g., a live vaccine. The viruses may be attenuated by any method known in the art and/or exemplified herein, e.g., engineering the virus to comprise a mutation in the NS1 gene or to comprise a modification in the polybasic amino acid sequence before the cleavage site in the HA protein (see U.S. Pat. No. 6,468,544; U.S. Pat. No. 6,669,943; Li et al., J. Infect. Dis. 179:1132-1138, each of which is hereby incorporated by reference in its entirety).

In one embodiment, an attenuated chimeric avian influenza virus of the invention comprises a genome comprising a mutation in the NS1 gene of the avian influenza backbone virus, which is known in other influenza viruses to diminishes the ability of the NS1 gene product to antagonize a cellular interferon response. In another embodiment, an attenuated chimeric avian influenza virus of the invention comprises a genome comprising a mutation in the HA gene of the avian influenza backbone virus, which is known in other influenza viruses to diminishes or eliminates the ability of cellular proteases to cleave the protein into its active form and thereby reduce or eliminate HA induced fusion and infectivity. In yet another embodiment, an attenuated chimeric avian influenza virus of the invention comprises a genome comprising a mutation in both the HA gene and NS1 gene of the avian influenza backbone virus, which are known in other influenza viruses to either separately or when combined to reduce or diminish viral activity. The titers of attenuated-chimeric and wild-type avian influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in CEF cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., CEF cells, MDCK cells, etc.) that are grown in serum-free or serum reduced (e.g., TPCK trypsin) medium.

5.2 Chimeric Newcastle Disease Virus

The present invention encompasses the engineering of an Newcastle Disease Virus ("NSV") such that at least one fusion protein is encoded by the genome and, when expressed, is incorporated into the virion. Any NDV type or strain that can be engineered to express and incorporate the at least one fusion protein into the NDV virion can be selected and used in accordance with the invention including, but not limited to, naturally occurring strains, variants or mutants, mutagenized viruses, reassortants and/or genetically engineered viruses. In a specific embodiment, the NDV is a naturally occurring virus. In another specific embodiment, the NDV is a genetically engineered virus. For example, as described herein, mutant strains of the recombinant NDV, rNDV/F2aa and rNDV/F3aa, in which the cleavage site of the F protein was replaced with one containing one or two extra arginine residues, allowing the mutant cleavage site to be activated by ubiquitously expressed proteases of the furin family can be used in accordance with the methods of the invention. Non-limiting examples of NDVs which may be used in accordance with the methods of the invention include B1, LaSota, YG97, MET95, and F48E9. In a specific embodiment, the chimeric NDV or rNDV of the invention comprises a fusion protein containing the ectodomain of an influenza HA protein; in a specific example in accordance with this embodiment the influenza HA protein is the HA protein from influenza H7.

The present invention provides a chimeric NDV, comprising at least one fusion protein having an ectodomain (ED), or fragment thereof, of a protein of an infectious agent other than a NDV protein and the cytoplasmic (CT) and/or transmembrane (TM) domains of an essential NDV glycoprotein. The present invention also provides a chimeric NDV, comprising at least one fusion protein having an ED, or fragment thereof, and TM domain of a protein of an infectious agent other than a NDV glycoprotein and the CT of an essential NDV glycoprotein. The present invention further provides a chimeric NDV, comprising a fusion protein having an ED, or fragment thereof, and CT domain of a protein of an infectious agent other than a NDV glycoprotein and a TM domain of an essential NDV glycoprotein. In other words, the NDV virus serves as the "backbone" that is engineered to express and incorporate into its virion the fusion protein. The inclusion of the TM and/or CT domains of an essential NDV glycoprotein in the fusion protein permits the fusion protein to incorporate into the virion of the NDV. The TM and/or CT domains of the fusion protein may correspond to or be derived from any NDV that permits the fusion protein to incorporate into the virion of the NDV backbone.

In certain embodiments, the TM and/or CT domains of the fusion protein correspond to the TM and/or CT domains of a different type or strain of NDV than the backbone NDV. In preferred embodiments, the TM and/or CT domains of the fusion protein correspond to the TM and/or CT domains of the NDV backbone.

The NDV virion comprises two major surface glycoproteins: fusion protein (F) and hemagglutinin-neuraminidase (HN), both of which comprise a cytoplasmic domain, a transmembrane domain and an ectodomain. Accordingly, in certain embodiments, the TM and/or CT domains of the fusion protein correspond to the TM and/or CT domains of either an F protein or an HN protein of an NDV.

The TM and CT domains of NDV F and HN proteins are structurally distinct in that the domains are located at the C-terminus of the F protein and the N-terminus of the HN protein. Therefore, when designing the fusion protein to be engineered into the NDV, the orientation of the ectodomain of the infectious agent to be fused to the TM and/or CT domains of NDV glycoprotein will guide the selection of the TM and/or CT domains.

In certain embodiments the at least one fusion protein of the chimeric NDV comprises the TM domain and 1 to 15, 1 to 10, 1 to 5, 1 to 3, 2 or 1 immediately adjacent residues of the ectodomain of an essential NDV glycoprotein. For example, in a specific embodiment, the fusion protein comprises the transmembrane domain of an NDV F protein, 1 to 15, 1 to 10, 1 to 5, 1 to 3, 2 or 1 immediately adjacent residue(s) of the ectodomain of the NDV F protein, and the ectodomain, or fragment thereof, of an infectious agent other than NDV such that the fusion protein can functionally replace the function of F protein. In another specific embodiment, the fusion protein comprises the cytoplasmic and transmembrane domains of a NDV F protein, 1 to 15, 1 to 10, 1 to 5, 1 to 3, 2 or 1 residue(s) of the ectodomain of the NDV F protein that are immediately adjacent to the transmembrane domain of the NDV F protein, and the ectodomain, or fragment thereof, of an infectious agent other than NDV such that the fusion protein can functionally replace the F protein. In another specific embodiment, the fusion protein comprises the transmembrane domain of an NDV HN protein, 1 to 15, 1 to 10, 1 to 5, 1 to 3, 2 or 1 immediately adjacent residue(s) of the ectodomain of the NDV HN protein, and the ectodomain, or fragment thereof, of an infectious agent other than NDV such that the fusion protein can functionally replace the function of HN protein. In another specific embodiment, the fusion protein comprises the cytoplasmic and transmembrane domains of an NDV HN protein, 1 to 15, 1 to 10, 1 to 5, 1 to 3, 2 or 1 residue(s) of the ectodomain of the NDV HN protein that are immediately adjacent to the transmembrane domain of the NDV HN protein, and the ectodomain, or fragment thereof, of an infectious agent other than NDV such that the fusion protein can functionally replace the HN protein.

In certain embodiments, an NDV surface glycoprotein (i.e., HN or F protein) is replaced by a fusion protein that supplies the required function(s) of the NDV glycoprotein. In accordance with these embodiments, the ectodomain of the fusion protein must be selected so that it will supply the required function(s) of the replaced NDV glycoprotein. In other embodiments, the fusion protein is expressed and incorporated into the virion of the NDV in addition to the native NDV surface glycoproteins.

In certain embodiments, the at least one fusion protein of the chimeric NDV of the invention does not comprise the complete ectodomain of a heterologous protein (e.g., comprises an antigenic fragment of the ectodomain of a protein of a heterologous infectious agent), and may or may not further comprise one or more fragments of the ectodomain of a native essential glycoprotein. Accordingly, in certain embodiments, the ectodomain of the fusion protein may comprise a fragment of the ectodomain of a protein of a heterologous infectious agent. In other embodiments, the ectodomain of the fusion protein may comprise fragments of both a native essential glycoprotein and a protein of a heterologous infectious agent. In embodiments where the fusion protein replaces an essential surface glycoprotein, the function of the surface glycoprotein must be supplied by the fusion protein, i.e., the fusion protein must exhibit the functionality of the surface glycoprotein that it is replacing.

Provided that the fusion protein described in this Section 5.2 is not required to replace the function of a necessary viral glycoprotein, the ectodomain of the fusion protein may correspond to or be derived from any heterologous molecule including, but not limited to, any infectious agent antigen (including, viral, bacterial and parasitic infectious agent antigens), and any disease antigen. Non-limiting examples of infectious agent antigens and/or disease antigens are provided in Section 5.3, infra.

The present invention encompasses nucleotide sequences encoding the fusion proteins described in this Section 5.2. In specific embodiments, a nucleotide sequence comprises nucleic acids encoding a Kozak sequence, followed by the gene end, intercistronic nucleotide (T), and gene start sequence of the F protein of NDV, followed by the 5' untranslated region and ORF of the HA protein of H7N2.

In preferred embodiments, the strains of NDV used in accordance with the invention are the lentogenic stains of the virus, i.e., those strains which typically exhibit low virulence or asymptomatic infection in avians, e.g., strain B1, strain LaSota or strain Met95. The invention also encompasses the use of highly virulent stains of NDV, e.g., YG97 or F48E9 or NDV strains that have been modified by genetic recombination using methods known in the art or exemplified herein. In a specific embodiment, the invention encompasses the use of an NDV wherein the NDV F protein has been genetically modified at the cleavage site so as to increase fusogenic activity. In a specific example in accordance with this invention, the modified F protein comprises two to three amino acid mutations at the F cleavage site. Replacement of a necessary surface protein of the backbone virus or introduction of a nucleotide sequence encoding a fusion protein into the viral genome may attenuate, or further attenuate, the resulting chimeric virus, i.e., the chimeric virus will exhibit impaired replication relative to wild type. In certain embodiments of the invention, attenuation, or further attenuation, of the chimeric virus is desired such that the chimeric virus remains, at least partially, infectious and can replicate in vivo, but only generate low titers resulting in subclinical levels of infection that are non-pathogenic. Such attenuated chimeric viruses are especially suited for embodiments of the invention wherein the virus is administered to a subject in order to act as an immunogen, e.g., a live vaccine. The viruses may be attenuated by any method known in the art.

5.3 Antigens that May be Engineered in to the Chimeric Viruses of the Invention In accordance with the invention, any heterologous molecule can be engineered into the virus backbone to elicit an immune response to said molecule. In a specific embodiment, any antigen of any infectious pathogen or associated with any disease that is capable of eliciting an immune response may be engineered into a NDV and/or influenza virus backbone. In a specific embodiment, the antigen is a glycoprotein. In certain preferred embodiments, the antigen is capable of functionally replacing an essential glycoprotein of an influenza virus and/or NDV. In specific embodiments, the antigen exhibits neuraminidase or hemagglutinin (e.g., receptor binding/fusogenic) activities. In selecting the viral backbone to express the antigen, the orientation of the nucleotide encoding the antigen is considered. For example, where the antigen is naturally anchored via its amino-terminus, the TM and CT domains or the TM domain for use in engineering the fusion protein will correspond to the TM and CT domains or the TM domain of a necessary viral protein of the backbone virus, or related virus, which is also naturally anchored via its amino terminus, e.g., the N protein of influenza or the HN protein of NDV.

In a specific embodiment, a viral antigen is engineered into a NDV or influenza virus backbone. Nonlimiting examples of viral antigens include antigens from adenoviridae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-1-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), human respiratory syncytial virus and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2 (e.g., HIV gp160), spumavirus), flaviviridae (e.g., hepatitis C virus, dengue virus, West Nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, Lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment the viral antigen, is HIV gp120, HIV nef, RSV F glycoprotein, RSV G glycoprotein, influenza virus neuraminidase, influenza virus hemagglutinin, HTLV tax, herpes simplex virus glycoprotein (e.g., gB, gC, gD, and gE) or hepatitis B surface antigen, hepatitis C virus E protein or coronavirus spike protein. In certain embodiments, the viral antigen is not gp 41. In certain embodiments, the viral antigen is derived from a paramyxovirus. In other, alternative embodiments, the viral antigen is not derived from a paramyxovirus. In certain embodiments, the viral antigen is derived from human parainfluenza virus type 1, human parainfluenza virus types 3, a RSV or from Sendai virus In other, alternative, embodiments, the viral antigen is not derived from human parainfluenza virus type 1, parainfluenza virus type 3, a RSV or from Sendai virus. In specific embodiments, the virus backbone is an influenza virus and the antigen engineered into the influenza virus backbone is not an influenza antigen. In other specific embodiments, the virus backbone is an NDV and the antigen engineered into the NDV backbone is not an NDV antigen.

In another embodiment, a bacterial antigen (e.g., bacterial coat protein or protective antigen associated with said bacteria) is engineered into a NDV or influenza virus backbone. Nonlimiting examples of bacterial antigens include antigens from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus* pyrogenes), *Streptococcus* (e.g., *Streptococcus enteritidis, Streptococcus fasciae*, and *Streptococcus pneu-*

*moniae*), Vampirovibr Helicobacter family, Yersinia family, *Bacillus antracis* and Vampirovibrio family.

In other embodiments, a protective antigen associated with a parasite (e.g. a protozoan) is engineered into a NDV or influenza virus backbone. Any antigen associated with a parasite or protective antigen of a parasite (e.g., a protozoan) may be used in accordance with the methods of the invention. Nonlimiting examples of parasite antigens include antigens from a parasite such as an amoeba, a malarial parasite, *Plasmodium, Trypanosoma cruzi.*

In another embodiment, a fungal antigen is engineered into a NDV or influenza virus backbone. Nonlimiting examples of fungal antigens include antigens from fungus of *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea*, and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii, zygomycetes*, and classes such as Zygomycetes, Ascomycetes, the Basidiomycetes, Deuteromycetes, and Oomycetes.

In another embodiment, a tumor associated antigen is engineered into a NDV or influenza virus backbone. Any tumor associated antigen known in the art may be used in accordance with the methods of the invention. Nonlimiting examples of tumor associated antigens include MAGE-1, MAGE-3, BAGE, GAGE-1, GAGE-2, N-acetylglucosaminyltransferase-V, p-15, MART-1/MelanA, TRP-1 (gp75), Tyrosinase, cyclin-dependent kinase 4, β-catenin, MUM-1, CDK4, HER-2/neu, human papillomavirus-E6, human papillomavirus E7, MUC-1, caspase-8, CD5, CD20, CEA, mucin-1, CA-125, epidermal growth factor receptor, $p185^{HER2}$, IL-2R, Fap-α, tenascin, antigens associated with a metalloproteinase, and CAMPATH-1.

5.4 Construction and Propagation of Chimeric Viruses of the Invention

The chimeric viruses of the invention can be generated using the reverse genetics technique. The reverse genetics technique involves the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer a chimeric virus of the invention. Briefly, with respect to influenza virus, full length cDNAs of viral segments are amplified using PCR with primers that include unique restriction sites, which allow the insertion of the PCR product into the a plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins are transfected into cells leading to production of recombinant viral particles. For a detailed description of helper-free plasmid technology see, e.g., International Publication No. WO 01/04333; U.S. Pat. No. 6,649,372; Fodor et al., 1999, J. Virol. 73:9679-9682; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties. Similarly, with respect to the single segment genome of NDV, a complete cDNA of the Hitchner B1 strain was constructed, inserted into a plasmid vector and engineered to containing a unique restriction site between the P and M genes. The fusion protein engineered in accordance with the invention may then be inserted into the viral genome at the unique restriction site. The single segment was positioned between a T7 promoter and the hepatitis delta virus ribozyme to produce an exact negative transcript from the T7 polymerase. The plasmid vector and expression vectors comprising the necessary viral proteins are transfected into cells leading to production of recombinant viral particles (see Swayne et al., 2003, Avian Dis. 47:1047-1050 and Swayne et al., 2001, J. Virol. 11868-11873, each of which is incorporated by reference in its entirety).

The chimeric influenza viruses of the invention can be engineered to contain RNA segments which are bicistronic. Bicistronic techniques allow the engineering of coding sequences of multiple proteins into a single mRNA through the use of IRES sequences. IRES sequences direct the internal recruitment of ribozomes to the RNA molecule and allow downstream translation in a cap independent manner. Briefly, an coding region of one protein is inserted into the ORF of a second protein. The insertion is flanked by an IRES and any untranslated signal sequences necessary for proper expression and/or function. The insertion must not disrupt the open reading frame, polyadenylation or transcriptional promoters of the second protein (see e.g., García-Sastre et al., 1994, J. Virol. 68:6254-6261 and García-Sastre et al., 1994 Dev. Biol. Stand. 82:237-246), each of which is hereby incorporated by reference in its entirety.

5.4.1 Propagation of Chimeric Viruses

The chimeric influenza viruses of the present invention can be propagated in any substrate that allows the virus to grow to titers that permit the uses of the chimeric viruses described herein. In one embodiment, the substrate allows the chimeric viruses to grow to titers comparable to those determined for the corresponding wild-type viruses. In a specific embodiment, the attenuated chimeric influenza viruses of the invention are propagated in IFN-deficient substrates.

The chimeric viruses of the invention may be grown in cells (e.g. avian cells, chicken cells, etc.) that are susceptible to infection by the viruses, embryonated eggs or animals (e.g., birds). Such methods are well-known to those skilled in the art. In a specific embodiment, the cells used to propagate attenuated influenza viruses with a reduced interferon antagonist activity are IFN-deficient. In one embodiment, the chimeric avian viruses of the invention are propagated in chicken cells or embryonated eggs. Representative chicken cells include, but are not limited to, chicken embryo fibroblasts or chicken embryo kidney cells.

Chimeric viruses of the invention may be propagated in embryonated eggs, e.g., from 6 to 14 days old. Young or immature embryonated eggs can be used to propagate attenuated chimeric influenza viruses of the invention. Immature embryonated eggs encompass eggs which are less than ten day old eggs, e.g., eggs 6 to 9 days that are INF-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. The chimeric viruses of the invention can be propagated in different locations of the embryonated egg, e.g., the allantoic cavity. For a detailed discussion on the growth and propagation viruses, in particular attenuated influenza viruses with at reduced interferon antagonist activity see, e.g., U.S. Pat. No. 6,852,522 and U.S. Pat. No. 6,852,522, both of which are hereby incorporated by reference in their entireties.

For virus isolation, the chimeric virus is removed from cell culture and separated from cellular components, typically by well known clarification procedures, e.g., such as gradient centrifugation and column chromatography, and may be further purified as desired using procedures well known to those skilled in the art, e.g., plaque assays.

5.5 Uses of Chimeric Viruses

The chimeric viruses of the invention can be used in active immunization in a subject. In one aspect, the chimeric viruses of the invention can be used to prevent, manage and or treat one or more diseases. In a specific aspect, the chimeric viruses of the invention can be used to prevent, manage and/or treat infections by two infectious agents. See Section 5.5.1 for a description of immunogenic formulation and uses of those formulations for inducing an immune response in a subject. The chimeric viruses of the invention can also be used to produce antibodies which can be used in diagnostic immunoassays, passive immunotherapy, and generation of antiidiotypic antibodies. For example, a chimeric influenza virus comprising a fusion protein having an ectodomain of an infectious agent other than an influenza virus can be administered to a subject (e.g., a mouse, rat, pig, horse, donkey, bird or human) to generate antibodies to both the influenza backbone and the infectious agent which can then be isolated and used in diagnostic assays, passive immunotherapy and generation of antiidiotypic antibodies. The generated antibodies may be isolated by standard techniques known in the art (e.g., immunoaffinity chromatography, centrifugation, precipitation, etc.) and used in diagnostic immunoassays, passive immunotherapy and generation of antiidiotypic antibodies. The isolated antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741, each of which is incorporated herein by reference in its entirety, for reviews on the generation of chimeric and humanized antibodies.

For antibodies produced by the chimeric viruses for use in passive immunization, the dosage administered to a subject is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the subject's body weight. The antibodies encompassed by the invention may be administered with other prophylactic or therapeutic compositions for the immunization again or treatment, management or prevention of an infectious disease or condition, or symptom thereof. Administration of doses antibodies of the invention may be by bolus injection or provided more slowly by IV (e.g., over about 5 minutes, about 15 minutes, about 30 minutes, about 45 minutes, about 1 hour, about 2 hours, about 4 hours, or about 6 hours). Dosages of the antibodies of the invention may also repeated (e.g., every day, every 2 days, every 3 days, every week, every 2 weeks, every 3 weeks, every 6 weeks, every 9 weeks, every 12 weeks, every 4 months, every 6 months, every 12 months, every 18 months, or every 2 years) over the couse of treatment (e.g., 2 weeks, 1 month, 2 months, 4 months, 6 months, 8 months, 10 months, 12 months, 16 months, 20 months, or 24 months or longer). In certain embodiemnts, the antibodies produced by the chimeric viruses of the invention may be administered parenterally, for example, intravenously, intramuscularly or subcutaneously, or, alternatively, are administered orally or intranasaly. The antibodies encompassed by the invention may also be administered as a sustained release formulation.

The antibodies isolated from subjects administered a chimeric virus of the invention may also be used to monitor treatment and/or disease progression. Any immunoassay system known in the art may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

The antibodies generated by the chimeric viruses of the invention can also be used in the production of antiidiotypic antibody. The antiidiotypic antibody can then in turn be used for immunization, in order to produce a subpopulation of antibodies that bind an initial antigen of chimeric influenza (Jerne, 1974, Ann. Immunol. (Paris) 125c:373; Jerne et al., 1982, EMBO J. 1:234).

In immunization procedures, the amount of immunogen to be used and the immunization schedule will be determined by a physician skilled in the art and will be administered by reference to the immune response and antibody titers of the subject.

5.5.1 Immunogenic Formulations

The invention also encompasses the use of the chimeric viruses of the invention in immunogenic formulations, e.g., vaccine formulations. In cases where the immunogenic formulations comprise a chimeric influenza virus, the formulations may be used in methods of preventing, managing, neutralizing, treating and/or ameliorating influenza virus infection, and/or infections by another infectious agent and/or a disease. In cases where the immunogenic formulations comprise a chimeric NDV, the formulations may be used in methods of preventing, managing, neutralizing, treating and/or ameliorating an NDV infection, infections by another infectious agent and/or a disease.

The immunogenic formulations may comprise either a live or inactivated chimeric virus of the invention. The chimeric virus can be inactivated by methods well known to those of skill in the art. Common methods use formalin and heat for inactivation. See, e.g., U.S. Pat. No. 6,635,246, which is herein incorporated by reference in its entirety. Other methods include those described in U.S. Pat. Nos. 5,891,705; 5,106,619 and 4,693,981, herein incorporated by reference in their entireties.

A live immunogenic formulation may be preferred because multiplication in the subject leads to a prolonged stimulus of similar kind and magnitude to that occurring in natural infections, and therefore, confers substantial, long lasting immunity. Production of such live recombinant immunogenic formulations may be accomplished using conventional methods involving propagation of the chimeric virus in cell culture or in embryonated eggs (e.g., chick embryonated eggs) followed by purification. Moreover, the chimeric viruses can induce a robust IFN response which has other biological consequences in vivo, affording protection against subsequent infections.

In a preferred embodiment, the immunogenic formulations of the present invention comprise an effective amount of a chimeric virus of the invention, and a pharmaceutically acceptable carrier. The term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration. The particular formulation may also depend on whether the chimeric virus is live or inactivated.

The immunogenic formulations of the invention may be administered to a naïve subject, i.e., a subject that does not have a disease or has not been and is not currently infected with one or both infectious agents. In one embodiment, the immunogenic formulations are administered to a naïve subject, i.e., a subject that does not have a disease or has not been and is not currently infected with one or both infectious agents, but is at risk of acquiring such disease (e.g., a viral infection). In one embodiment, the immunogenic formulations of the invention are administered to a subject that does not have a disease, or has not and is not infected with one of the infectious agents to which the chimeric virus induces an immune response. In another embodiment, the immunogenic formulations of the invention are administered to a subject that has not and is not infected with both of the infectious agents to which the chimeric virus induces an immune response. The immunogenic formulations of the invention may also be administered to a subject that is and/or has been infected with one or both of the infectious agents or another type, subtype or strain of the agents to which the chimeric virus induces an immune response.

Many methods may be used to introduce the immunogenic formulations, e.g., vaccine formulations described above, these include but are not limited to intranasal, intratracheal, oral, intradermal, intramuscular, intraperitoneal, intravenous, conjunctival and subcutaneous routes. In birds, the methods may further include choanal inoculation. As an alternative to parenteral administration, the invention also encompasses, routes of mass administration for agricultural purposes such as via drinking water or in a spray. It may be preferable to introduce the chimeric influenza virus immunogenic formulation via the natural route of infection of the wild-type virus. Alternatively, it may be preferable to introduce the chimeric virus of the invention via the natural route of infection of the agent from which the fusion protein is derived. The ability of chimeric virus to induce a vigorous secretory and cellular immune response can be used advantageously. For example, infection of the respiratory tract by the chimeric viruses may induce a strong secretory immune response, for example in the urogenital system, with concomitant protection against a particular disease causing agent. In addition, in a preferred embodiment it may be desirable to introduce the pharmaceutical formulations of the invention into the lungs by any suitable route. Pulmonary administration can also be employed, e.g., by use of an inhaler or nebulizer, and formulation with an aerosolizing agent for use as a spray.

In certain embodiments, an immunogenic formulation of the invention does not result in complete protection from an infection (e.g., a viral infection or infection by a non-viral infectious agent), but results in a lower titer or reduced number of the pathogen (e.g., a virus) compared to an untreated subject. In certain embodiments, administration of the immunogenic formulations of the invention results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of the pathogen relative to an untreated subject. Benefits of a reduction in the titer, number or total burden of pathogen include, but are not limited to, less severity of symptoms of the infection and a reduction in the length of the disease or condition associated with the infection.

In certain embodiments, an immunogenic formulation of the invention is used to protect against a disease (e.g., an infection) in naïve subjects. In a specific embodiment, an immugenic formulation of the invention is used to protect against an infection by influenza virus and/or at least one other infectious agent which is not an influenza virus and/or protect against a disease or symptom associated with the infection in a naïve subject. In other embodiments, an immunogenic formulation of the invention is used to protect against infection by NDV and/or at least one other infectious agent and/or protect agains a disease or symptom associated therewith in naïve subjects. Non-limiting examples of such other infectious agents are papilloma virus, herpes virus, retrovirus (e.g. HIV), hepatitis virus, rhinovirus, respiratory synctial virus, NDV, cytomegalovirus, adenovirus, *Clostridia* sp., *Salmonella* sp., *Staphylococcus* sp., *Enterococcus* sp., *Vibrio* sp., *E. coli, Streptococcus equi, Mycoplasma pneumoniae, Kleb-*

*siella pneumoniae* and *Pseudomonas aeruginosa*, and *Dermatophilus congolensis*, or a protozoan such as amobea, malarial parasite or *Trypanosoma cruzi*.

The prophylactic and/or therapeutic effect of the immunogenic formulations of the invention are based, in part, upon achieving or inducing an immune response (e.g., a hummoral immune response). In one aspect, the immunogenic formulations induce a detectable serum titer of an antibody against antigens of the chimeric virus in either the subject or an animal model thereof (e.g. mouse, rat or canine model). The serum titer of an antibody can be determined using techniques known to one of skill in the art, e.g., immunoassays such as ELISAs. In one embodiment, the antibodies specifically bind to an antigen of the backbone of the chimeric virus. In other embodiments, the antibodies specifically bind to an antigen of the at least one fusion protein, i.e., an antigen of the ectodomain of the introduced protein associated with an infectious agent or disease. In a specific embodiment, the antibodies generated by administering an immunogenic formulation of the invention are neutralizing antibodies.

In one embodiment, administration of a chimeric virus of the invention to a subject or animal model thereof results in a serum titer of about 1 μg/ml, about 2 μg/ml, about 5 μg/ml, about 6 μg/ml, about 10 μg/ml, about 15 μg/ml, about 20 μg/ml, about 25 μg/ml, about 50 mg/ml, about 75 mg/ml, about 100 mg/ml, about 125 mg/ml, about 150 mg/ml, about 175 mg/ml, about 200 mg/ml, about 225 mg/ml, about 250 mg/ml, about 275 mg/ml, or about 300 mg/ml or more of an antibody that specifically binds to an antigen of the backbone of the chimeric virus. In other embodiments, administration of a chimeric virus of the invention to a subject or animal model thereof results in a serum titer of about 1 μg/ml, about 2 μg/ml, about 5 μg/ml, about 6 μg/ml, about 10 μg/ml, about 15 μg/ml, about 20 μg/ml, about 25 μg/ml, about 50 mg/ml, about 75 mg/ml, about 100 mg/ml, about 125 mg/ml, about 150 mg/ml, about 175 mg/ml, about 200 mg/ml, about 225 mg/ml, about 250 mg/ml, about 275 mg/ml, or about 300 mg/ml or more of an antibody that specifically binds to an antigen of fusion protein, i.e., an antigen of the ectodomain of the introduced protein associated with an infectious agent or disease. Preferably a serum titer of about 1 μg/ml, about 2 μg/ml, about 5 μg/ml, about 6 μg/ml, about 10 μg/ml, about 15 μg/ml, about 20 μg/ml, about 25 μg/ml, about 50 mg/ml, about 100 mg/ml, about 150 mg/ml or about 300 mg/ml or more of such antibodies is achieved approximately 20 days (preferably 25, 30, 35 or 40 days) after administration of a first dose of an immunogenic formulation of the invention and without administration of any other doses the formulation. The immune response may be determined in the subject or in a animal model, which response is then correlated or extrapolated to a predicted response in the subject, e.g., a human.

In one embodiment, the present invention provides methods for preventing at least one disease (e.g., an influenza infection and/or infections by another infectious agent which is not influenza) in a subject, the methods comprising administering to said subject a first dose of an effective amount of an immunogenic formulation comprising a chimeric influenza virus of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen or epitope of the backbone of the chimeric virus 2 days, 5 days, 10 days, 15 days, 20 days or, preferably, 30 days after the first administration and prior to any subsequent administration. In another embodiment, the present invention provides methods for preventing at least one disease (e.g., an influenza infection and/or infections by another infectious agent which is not influenza) in a subject, the methods comprising administering to said subject a first dose of an effective amount of an immunogenic formulation comprising a chimeric influenza virus of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the fusion protein (i.e., an antigen of the ectodomain of the introduced protein associated with a disease) at 2 days, 5 days, 10 days, 15 days, 20 days or, preferably, 30 days after the first administration and prior to any subsequent administration. The immune response may be determined in the subject or in a animal model, which response is then correlated or extrapolated to a predicted response in the subject, e.g., a human. In one embodiment, the present invention provides methods for preventing an avian influenza infection and/or infections by another infectious agent which is not avian influenza in an avian, the method comprising administering a first dose of an immunogenic formulation comprising a chimeric avian influenza virus of the invention, which chimeric avian influenza virus comprises a fusion protein containing a heterologous protein sequence, to said subject of an effective amount of the chimeric avian virus of the invention, wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the chimeric virus and/or antibodies that immunospecifically bind to an antigen of the fusion protein 2 days, 5 days, 10 days, 15 days, 20 days or, preferably, 30 days after the first administration and prior to any subsequent administration. In some embodiments, the dose of the chimeric influenza virus administered to the subject or animal model is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

In one embodiment, the present invention provides methods for treating at least one disease (e.g., an influenza infection and/or infections by another infectious agent which is not influenza) in a subject, the methods comprising administering to said subject a first dose of an effective amount of an immunogenic formulation comprising a chimeric influenza virus of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen or epitope of the backbone of the chimeric virus 2 days, 5 days, 10 days, 15 days, 20 days or, preferably, 30 days after the first administration and prior to any subsequent administration. In another embodiment, the present invention provides methods for treating at least one disease (e.g., an influenza infection and/or infections by another infectious agent which is not influenza) in a subject, the methods comprising administering to said subject a first dose of an effective amount of an immunogenic formulation comprising a chimeric influenza virus of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the fusion protein (i.e., an antigen of the ectodomain of the introduced protein associated with a disease) at 2 days, 5 days, 10 days, 15 days, 20 days or, preferably, 30 days after the first administration and prior to any subsequent administration. The immune response may be determined in the subject or in a animal model, which response is then correlated or extrapolated to a predicted response in the subject, e.g., a human. In one embodiment, the present invention provides methods for treating an avian influenza infection and/or infections by another infectious agent which is not avian influenza in an avian, the method comprising administering a first dose of an immunogenic formulation comprising a chimeric avian influenza virus of the invention, which chimeric avian influenza virus comprises a fusion protein containing a heterologous protein sequence, to said subject of an effective amount of the chimeric avian virus of the invention, wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the chimeric virus and/or antibodies that immunospecifically bind to an antigen of the fusion protein 2 days, 5 days, 10 days, 15 days, 20 days or, preferably, 30 days after the first administration and prior to any subsequent administration. In some embodiments, the dose of the chimeric influenza virus administered to the subject or animal model is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

In one embodiment, the present invention provides methods for managing and/or ameliorating at least one disease (e.g., an influenza infection and/or infections by another infectious agent which is not influenza) in a subject, the methods comprising administering to said subject a first dose of an effective amount of an immunogenic formulation comprising a chimeric influenza virus of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen or epitope of the backbone of the chimeric virus 2 days, 5 days, 10 days, 15 days, 20 days or, preferably, 30 days after the first administration and prior to any subsequent administration. In another embodiment, the present invention provides methods for managing and/or ameliorating at least one disease (e.g., an influenza infection and/or infections by another infectious agent which is not influenza) in a subject, the methods comprising administering to said subject a first dose of an effective amount of an immunogenic formulation comprising a chimeric influenza virus of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the fusion protein (i.e., an antigen of the ectodomain of the introduced protein associated with a disease) at 2 days, 5 days, 10 days, 15 days, 20 days or, preferably, 30 days after the first administration and prior to any subsequent administration. The immune response may be determined in the subject or in a animal model, which response is then correlated or extrapolated to a predicted response in the subject, e.g., a human. In one embodiment, the present invention provides methods for managing and/or ameliorating an avian influenza infection and/or infections by another infectious agent which is not avian influenza in an avian, the method comprising administering a first dose of an immunogenic formulation comprising a chimeric avian influenza virus of the invention, which chimeric avian influenza virus comprises a fusion protein containing a heterologous protein sequence, to said subject of an effective amount of the chimeric avian virus of the invention, wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the chimeric virus and/or antibodies that immunospecifically bind to an antigen of the fusion protein 2 days, 5 days, 10 days, 15 days, 20 days or, preferably, 30 days after the first administration and prior to any subsequent administration. In some embodiments, the dose of the chimeric influenza virus administered to the subject or animal model is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

In one embodiment, the present invention provides methods for preventing at least one disease (e.g., an NDV infection and/or infections by another infectious agent which is not NDV) in a subject, the methods comprising administering to said subject a first dose of an effective amount of an immunogenic formulation comprising a chimeric NDV of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen or epitope of the backbone of the chimeric virus 2 days, 5 days, 10 days, 15 days, 20 days or, preferably, 30 days after the first administration and prior to any subsequent administration. In another embodiment, the present invention provides methods for preventing at least one disease (e.g., an NDV infection and/or infections by another infectious agent which is not NDV) in a subject, the methods comprising administering to said subject a first dose of an effective amount of an immunogenic formulation comprising a chimeric NDV of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the fusion protein (i.e., an antigen of the ectodomain of the introduced protein associated with a disease) at 2 days, 5 days, 10 days, 15 days, 20 days or, preferably, 30 days after the first administration and prior to any subsequent administration. The immune response may be determined in the subject or in a animal model, which response is then correlated or extrapolated to a predicted response in the subject, e.g., a human. In one embodiment, the present invention provides methods for preventing an NDV infection and/or infections by another infectious agent which is not NDV in an avian, the method comprising administering a first dose of an immunogenic formulation comprising a chimeric NDV of the invention, which chimeric NDV comprises a fusion protein containing a heterologous protein sequence, to said subject of an effective amount of the chimeric virus of the invention, wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the chimeric virus and/or antibodies that immunospecifically bind to an antigen of the fusion protein 2 days, 5 days, 10 days, 15 days, 20 days or, preferably, 30 days after the first administration and prior to any subsequent administration. In some embodiments, the dose of the chimeric influenza virus administered to the subject or animal model is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

In one embodiment, the present invention provides methods for treating at least one disease (e.g., an NDV infection and/or infections by another infectious agent which is not NDV) in a subject, the methods comprising administering to said subject a first dose of an effective amount of an immunogenic formulation comprising a chimeric NDV of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen or epitope of the backbone of the chimeric virus 2 days, 5 days, 10 days, 15 days, 20 days or, preferably, 30 days after the first administration and prior to any subsequent administration. In another embodiment, the present invention provides methods for treating at least one disease (e.g., an NDV infection and/or infections by another infectious agent which is not NDV) in a subject, the methods comprising administering to said subject a first dose of an effective amount of an immunogenic formulation comprising a chimeric NDV of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the fusion protein (i.e., an antigen of the ectodomain of the introduced protein associated with a disease) at 2 days, 5 days, 10 days, 15 days, 20 days or, preferably, 30 days after the first administration and prior to any subsequent administration. The immune response may be determined in the subject or in a animal model, which response is then correlated or extrapolated to a predicted response in the subject, e.g., a human. In one embodiment, the present invention provides methods for treating an NDV infection and/or infections by another infectious agent which is not NDV in an avian, the method comprising administering a first dose of an immunogenic formulation comprising a chimeric NDV of the invention, which chimeric NDV comprises a fusion protein containing a heterologous protein sequence, to said subject of an effective amount of the chimeric virus of the invention, wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the chimeric virus and/or antibodies that immunospecifically bind to an antigen of the fusion protein 2 days, 5 days, 10 days, 15 days, 20 days or, preferably, 30 days after the first administration and prior to any subsequent administration. In some embodiments, the dose of the chimeric influenza virus administered to the subject or animal model is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

In one embodiment, the present invention provides methods for managing and/or ameliorating at least one disease (e.g., an NDV infection and/or infections by another infectious agent which is not NDV) in a subject, the methods comprising administering to said subject a first dose of an effective amount of an immunogenic formulation comprising a chimeric NDV of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen or epitope of the backbone of the chimeric virus 2 days, 5 days, 10 days, 15 days, 20 days or, preferably, 30 days after the first administration and prior to any subsequent administration. In another embodiment, the present invention provides methods for managing and/or ameliorating at least one disease (e.g., an NDV infection and/or infections by another infectious agent which is not NDV) in a subject, the methods comprising administering to said subject a first dose of an effective amount of an immunogenic formulation comprising a chimeric NDV of the invention, which chimeric virus comprises a fusion protein of a heterologous sequence (e.g. a disease antigen), wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the fusion protein (i.e., an antigen of the ectodomain of the introduced protein associated with a disease) at 2 days, 5 days, 10 days, 15 days, 20 days or, preferably, 30 days after the first administration and prior to any subsequent administration. The immune response may be determined in the subject or in a animal model, which response is then correlated or extrapolated to a predicted response in the subject, e.g., a human. In one embodiment, the present invention provides methods for managing and/or ameliorating an NDV infection and/or infections by another infectious agent which is not NDV in an avian, the method comprising administering a first dose of an immunogenic formulation comprising a chimeric NDV of the invention, which chimeric NDV comprises a fusion protein containing a heterologous protein sequence, to said subject of an effective amount of the chimeric virus of the invention, wherein the effective amount is the amount that results in a serum titer of about 10 μg/ml, 20 μg/ml, 30 μg/ml, 40 μg/ml, 50 μg/ml, 60 μg/ml, 70 μg/ml, 80 μg/ml, 100 μg/ml or greater of antibodies that immunospecifically bind to an antigen of the chimeric virus and/or antibodies that immunospecifically bind to an antigen of the fusion protein 2 days, 5 days, 10 days, 15 days, 20 days or, preferably, 30 days after the first administration and prior to any subsequent administration. In some embodiments, the dose of the chimeric influenza virus administered to the subject or animal model is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

The present invention also provides methods for preventing, treating and/or managing at least one disease, the methods comprising administering to said subject an effective amount of an immunogenic formulation comprising a chimeric influenza virus of the invention, wherein the effective amount is the amount that results in a reduction in mortality, reduction in hospitalization, reduction in the severity of the disease and/or reduction in the clinical symptoms of the disease relative to a subject not administered the immunogenic formulation of the invention. In certain embodiments the subject is a human. In some embodiments, the dose of the chimeric influenza virus administered to the subject is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu.

In another embodiment, the present invention provides methods for preventing, treating and/or managing at least one disease (e.g., an avian influenza infection and/or infection by another infectious agent which is not avian influenza) in a subject (preferably avian), the methods comprising administering to said subject an effective amount of a immunogenic formulation comprising a chimeric avian influenza virus of the invention, wherein the effective amount is the amount that results in a reduction in the titer or number of infectious agents, reduction in mortality, reduction in hospitalization, reduction in the severity of infection and/or reduction in the clinical symptoms of the infection relative to a subject not administered the immunogenic formulation of the invention. In some embodiments, the dose of the chimeric avian influenza virus administered to the subject is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu. In certain embodiments, administration of the immunogenic formulation of the invention results in a 10%, 20%, 30%, 40%, 50%, 60%, 70%, or 80% or more reduction in the replication of the infectious agent relative to a subject not administered the immunogenic formulation of the invention as determined at 2 days, 5 days, 10 days, 15 days, 20 days or, preferably, 30 days after said administration by any method known in the art or exemplified herein (e.g., determination of viral titer). In other embodiments, administration of an immunogenic formulation of the invention results in a 1, 2, 3, 4, 5, 10, 15, 20, 25, 50, 75, or 100 fold reduction in the replication of the infectious agent or the burden of infectious agent relative to a subject not administered an immunogenic formulation of the invention as determined at 2 days, 5 days, 10 days, 15 days, 20 days or, preferably, 30 days after said administration by any method known in the art or exemplified herein (e.g., determination of viral titer or bacterial load and/or concentration).

In another embodiment, the present invention provides methods for preventing, treating and/or ameliorating at least one disease (e.g., an NDV infection and/or infection by another infectious agent which is not NDV) in a subject (e.g., an avian), the methods comprising administering to said subject an effective amount of an immunogenic formulation comprising a chimeric NDV virus of the invention, wherein the effective amount is the amount that results in a reduction in the titer or number of infectious agents, reduction in mortality, reduction in hospitalization, reduction in the severity of infection and/or reduction in the clinical symptoms of the infection relative to a subject not administered the immunogenic formulation of the invention. In some embodiments, the dose of the chimeric NDV virus administered to the subject is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu. In certain embodiments, administration of the immunogenic formulation of the invention results in a 10%, 20%, 30%, 40%, 50%, 60%, 70%, or 80% or more reduction in the replication of the infectious agent relative to a subject not administered the immunogenic formulation of the invention as determined at 2 days, 5 days, 10 days, 15 days, 20 days or, preferably, 30 days after said administration by any method known in the art or exemplified herein (e.g., determination of viral titer). In other embodiments, administration of the immunogenic formulation of the invention results in a 1, 2, 3, 4, 5, 10, 15, 20, 25, 50, 75, or 100 fold reduction in the replication of the infectious agent or the burden of infectious agent relative to a subject not administered the immunogenic formulation of the invention as determined at 2 days, 5 days, 10 days, 15 days, 20 days or, preferably, 30 days after said administration by any method known in the art or exemplified herein (e.g., determination of viral titer).

The amount of the immunogenic formulation of the invention which will be effective in the treatment, prevention an/or amelioration of a particular disease (e.g. viral infection) will depend on the nature of the disease, and can be determined by standard clinical techniques. In addition, in vitro assays may optionally be employed to help identify optimal dosage ranges. The precise dose to be employed in the formulation will also depend on the route of administration, and the seriousness of the infection or disorder, and should be decided according to the judgment of the practitioner and each subject's circumstances. However, suitable dosage ranges for administration are generally about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and most preferably about $10^4$ to about $10^{12}$, and can be administered to a subject once, twice, three or more times with intervals as often as needed. Effective doses may be extrapolated from dose response curves derived from in vitro or animal model test systems.

In various embodiments, the immunogenic formulations of the invention or antibodies generated by the chimeric viruses of the invention are administered to a subject in combination with one or more other therapies (e.g. antiviral or immunomodulatory therapies) for the prevention of at least one disease (e.g. an influenza infection and/or infection by another infectious agent which is not influenza virus). In other embodiments, the immunogenic formulations of the invention or antibodies generated by the chimeric viruses of the invention are administered to a subject in combination with one or more other therapies (e.g. antiviral or immunomodulatory therapies) for the treatment of at least one disease (e.g. an influenza infection and/or infection by another infectious agent which is not influenza virus). In yet other embodiments, the immunogenic formulations of the invention or antibodies generated by the chimeric viruses of the invention are administered to a subject in combination with one or more other therapies (e.g. antiviral or immunomodulatory therapies) for the management and/or amelioration of at least one disease (e.g. an influenza infection and/or infection by another infectious agent which is not influenza virus). In a specific embodiment, the immunogenic formulations of the invention or antibodies generated by the chimeric viruses of the invention are administered to a subject in combination with one or more other therapies (e.g. antiviral or immunomodulatory therapies) for the prevention of an avian influenza infection and/or infection by another infectious agent which is not avian influenza virus. In another specific embodiment, the immunogenic formulations of the invention or antibodies generated by the chimeric viruses of the invention are administered to a subject in combination with one or more other therapies (e.g. antiviral or immunomodulatory therapies) for the treatment of an avian influenza infection and/or infection by another infectious agent which is not avian influenza virus. In yet other embodiments, the immunogenic formulations of the invention or antibodies generated by the chimeric viruses of the invention are administered to a subject in combination with one or more other therapies (e.g. antiviral or immunomodulatory therapies) for the prevention of an NDV infection and/or infection by another infectious agent which is not NDV. In still other embodiments, the immunogenic formulations of the invention or antibodies generated by the chimeric viruses of the invention are administered to a subject in combination with one or more other therapies (e.g. antiviral or immunomodulatory therapies) for the treatment of an NDV infection and/or infection by another infectious agent which is not NDV. In certain embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

Any anti-viral agent well-known to one of skill in the art can be used in the formulations (e.g., vaccine formulations) and the methods of the invention. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

In specific embodiments, the anti-viral agent is an immunomodulatory agent that is immunospecific for a viral antigen. As used herein, the term "viral antigen" includes, but is not limited to, any viral peptide, polypeptide and protein (e.g., HIV gp120, HIV nef, RSV F glycoprotein, RSV G glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. Antibodies useful in this invention for treatment of a viral infectious disease include, but are not limited to, antibodies against antigens of pathogenic viruses, including as examples and not by limitation: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2), spumavirus), flaviviridae (e.g., hepatitis C virus, dengue virus, West nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Anti-bacterial agents and therapies well known to one of skill in the art for the prevention, treatment, management, or amelioration of bacterial infections can be used in the compositions (e.g., immunogenic formulations) and methods of the invention. Non-limiting examples of anti-bacterial agents include proteins, polypeptides, peptides, fusion proteins, antibodies, nucleic acid molecules, organic molecules, inorganic molecules, and small molecules that inhibit or reduce a bacterial infection, inhibit or reduce the replication of bacteria, or inhibit or reduce the spread of bacteria to other subjects. In particular, examples of anti-bacterial agents include, but are not limited to, penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine. Anti-bacterial therapies and their dosages, routes of administration and recommended usage are known in the art and have been described in such literature as the *Physician's Desk Reference* (56$^{th}$ ed., 2002). Additional information on respiratory infections and anti-bacterial therapies is available in *Cecil Textbook of Medicine* (18th ed., 1988).

Anti-fungal agents and therapies well known to one of skill in the art for prevention, management, treatment, and/or amelioration of a fungal infection or one or more symptoms thereof (e.g., a fungal respiratory infection) can be used in the compositions (e.g., immunogenic formulations) and methods of the invention. Non-limiting examples of anti-fungal agents include proteins, polypeptides, peptides, fusion proteins, antibodies, nucleic acid molecules, organic molecules, inorganic molecules, and small molecules that inhibit and/or reduce fungal infection, inhibit and/or reduce the replication of fungi, or inhibit and/or reduce the spread of fungi to other subjects. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole (SPORANOX®)), polyene (e.g., nystatin, amphotericin B (FUNGIZONE®), amphotericin B lipid complex ("ABLC") (ABELCET®), amphotericin B colloidal dispersion ("ABCD")(AMPHOTEC®), liposomal amphotericin B (AMBISONE®)), potassium iodide (KI), pyrimidine (e.g., flucytosine (ANCOBON®)), and voriconazole (VFEND®). Anti-fungal therapies and their dosages, routes of administration, and recommended usage are known in the art and have been described in such literature as Dodds et al., 2000 Pharmacotherapy 20(11) 1335-1355, the Physician's Desk Reference (57th ed., 2003) and the *Merk Manual of Diagnosis and Therapy* (17th ed., 1999).

In certain embodiments, an immunogenic formulation of the invention is administered to a subject as a single dose followed by a second dose 3 to 6 weeks later. In accordance with these embodiments, booster inoculations may be administered to the subject at 6 to 12 month intervals following the second inoculation. In one embodiment, the subject is a mammal. In another embodiment, the subject is a bird. In yet another embodiment the subject is a human. In a more preferred embodiment, the subject is a chicken at risk for contracting either NDV or avian influenza virus infection.

In certain embodiments, the administration of the same immunogenic formulations of the invention may be repeated and the administrations may be separated by at least 1 day, 2 days, 3 days, 5 days, 10 days, 15 days, 30 days, 45 days, 2 months, 75 days, 3 months, or at least 6 months.

5.6 Biological Assays

5.6.1 In Vitro Assays

Growth of the chimeric viruses of the present invention can be assessed by any method known in the art or described herein (e.g. in cell culture (e.g., cultures of chicken embryonic kidney cells or cultures of chicken embryonic fibroblasts (CEF)). Growth of the attenuated chimeric viruses of the invention can be assessed in IFN-competent and IFN-deficient cells. In a specific embodiment, CEF cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented with 5% allantoic fluid. Viral titers are determined in the supernatant by HA plagued in CEF cells as described below. Other cells in which viral titers can be assessed include, but are not limited to, EFK-2 cells, Vero cells, primary human umbilical vein endothelial cells (HUVEC), H292 human epithelial cell line and HeLa cells.

Incorporation of the fusion protein into the virion of the chimeric viruses of the present invention can be assessed by any method known in the art or described herein (e.g. in cell culture, animal model or viral culture in embryonated eggs). For example, viral particles from cell culture of the allantoic fluid of embryonated eggs can be purified by centrifugation through a sucrose cushion and subsequently analyzed for fusion protein expression by Western blotting using methods well known in the art.

Viral assays include those that measure altered viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Antibodies generated by the chimeric viruses of the present invention or fragments thereof may be characterized in a variety of ways well-known to one of skill in the art (e.g. ELISA, Surface Plasmon resonance display (BIAcore), Western blot, immunofluorescence, immunostaining and/or microneutralization assays). In particular, antibodies generated by the chimeric viruses of the present invention or fragments thereof may be assayed for the ability to immunospecifically bind to an antigen of the chimeric backbone virus or an antigen or epitope of the fusion protein. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Cwirla et al., 1990, Proc. Natl. Acad. Sci. USA 87:6378-6382; and Felici, 1991, J. Mol. Biol. 222:301-310) (each of these references is incorporated herein in its entirety by reference). Antibodies generated by the chimeric viruses of the present invention or fragments thereof that have been identified to immunospecifically bind to an antigen of the chimeric backbone virus or an antigen or epitope of the fusion protein can then be assayed for their specificity to said antigen.

The antibodies generated by the chimeric viruses of the present invention or fragments thereof may be assayed for immunospecific binding to an antigen of the chimeric virus of the invention (e.g., an antigen or epitope of the chimeric virus backbone or an antigen or epitope of the fusion protein (e.g., an antigen associated with a disease)) and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. In a preferred embodiment, an ELISA may be performed by coating a high binding 96-well microtiter plate (Costar) with 2 μg/ml of rhu-IL-9 in PBS overnight. Following three washes with PBS, the plate is incubated with three-fold serial dilutions of Fab at 25° C. for 1 hour. Following another three washes of PBS, 1 μg/ml anti-human kappa-alkaline phosphatase-conjugate is added and the plate is incubated for 1 hour at 25° C. Following three washes with PBST, the alkaline phosphatase activity is determined in 50 μl/AMP/PPMP substrate. The reactions are stopped and the absorbance at 560 nm is determined with a VMAX microplate reader. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of the present invention or a fragment thereof for an IL-9 polypeptide and the binding off-rates can be determined from the data by scatchard plot analysis. Competition with a second antibody can also be determined using radioimmunoassays. In this case, an IL-9 polypeptide is incubated with an antibody of the present invention conjugated to a labeled compound (e.g., $^{3}H$ or $^{125}I$) in the presence of increasing amounts of an unlabeled second antibody.

In a preferred embodiment, BIAcore kinetic analysis is used to determine the binding on and off rates of antibodies of the invention to an antigen of the chimeric virus of the invention (e.g., an antigen or epitope of the chimeric virus backbone or an antigen or epitope of the fusion protein (e.g., an antigen associated with a disease)). BIAcore kinetic analysis comprises analyzing the binding and dissociation of polypeptide comprising the antigen of interes from chips with immobilized antibodies generated by the chimeric viruses of the invention on their surface. A typical BIAcore kinetic study involves the injection of 2500, of an antibody reagent (mAb, Fab) at varying concentration in HBS buffer containing 0.005% Tween-20 over a sensor chip surface, onto which has been immobilized the antigen. The flow rate is maintained constant at 754/min. Dissociation data is collected for 15 min. or longer as necessary. Following each injection/dissociation cycle, the bound mAb is removed from the antigen surface using brief, 1 min. pulses of dilute acid, typically 10-100 mM HCl, though other regenerants are employed as the circumstances warrant. More specifically, for measurement of the rates of association, $k_{on}$, and dissociation, $k_{off}$, the polypeptide comprising the antigen is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide comprising the antigen in 10 mM NaOAc, pH4 or pH5 is prepared and passed over the EDC/NHS-activated surface until approximately 30-50 RU's worth of antigen are immobilized. Following this, the unreacted active esters are "capped" off with an injection of 1M Et-NH2. A blank surface, containing no antigen, is prepared under identical immobilization conditions for reference purposes. Once an appropriate surface has been prepared, a suitable dilution series of each one of the antibody reagents is prepared in HBS/Tween-20, and passed over both the antigen and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The antibodies generated by the chimeric viruses of the invention or fragments thereof can also be assayed for their ability to inhibit the binding of an antigen of the chimeric virus of the invention (e.g., an antigen or epitope of the chimeric virus backbone or an antigen or epitope of the fusion protein (e.g., an antigen associated with a disease)) to a host cell receptor using techniques known to those of skill in the art. For example, cells expressing receptors known to bind said antigens can be contacted with antigen in the presence or absence of an antibody generated by the chimeric viruses of the invention or fragment thereof and the ability of the antibody or fragment thereof to inhibit the antigen's binding can measured by, for example, flow cytometry or a scintillation assay. The antigen or the antibody or antibody fragment can be labeled with a detectable compound such as a radioactive label (e.g., 32P, 35S, and 125I) or a fluorescent label (e.g., fluorescein isothiocyanate, rhodamine, phycoerythrin, phycocyanin, allophycocyanin, o-phthaldehyde and fluorescamine) to enable detection of an interaction between the antigen and a cell receptor. Alternatively, the ability of antibodies generated by the chimeric viruses of the invention or fragments thereof to inhibit an antigen of the chimeric virus of the invention (e.g., an antigen or epitope of the chimeric virus backbone or an antigen or epitope of the fusion protein (e.g., an antigen associated with a disease)) from binding to a receptor can be determined in cell-free assays. For example, a polypeptide comprising the antigen can be contacted with an antibody or fragment thereof and the ability of the antibody or antibody fragment to inhibit the polypeptide from binding to a cell receptor can be determined. Preferably, the antibody or the antibody fragment is immobilized on a solid support and the polypeptide is labeled with a detectable compound. Alternatively, a polypeptide comprising the antigen is immobilized on a solid support and the antibody or fragment thereof is labeled with a detectable compound.

5.6.2 In Vivo Assays

The virulence of the chimeric viruses of the present invention can be assessed in a subject, in particular avians, or in an animal model thereof. In one example, the ability to induce lung lesions and cause infection in an animal model of virus infection is compared to wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

For quantitation of virus in tissue samples, tissue samples are homogenized in phosphate-buffered saline (PBS), and dilutions of clarified homogenates adsorbed for 1 h at 37° C. onto monolayers of cells (e.g., CEF or MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., CEF or MDCK cells) in 96-well plates are incubated with log dilutions of clarified tissue homogenates in media. Two to three days after inoculation, 0.05-ml aliquots from each well are assessed for viral growth by hemagglutination assay (HA assay).

In yet other assays, histopathologic evaluations are performed after infection. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

5.6.3 Determining Viral Titer

Viral titer is determined by inoculating serial dilutions of chimeric virus into cell cultures (e.g., CEF or MDCK), chick embryos, or live animals (e.g., avians). After incubation of the virus for a specified time, the virus is isolated using standard methods.

The HA assay may be carried out in V-bottom 96-well plates. Serial twofold dilutions of each sample in PBS are incubated for 1 h on ice with an equal volume of a 0.5% suspension of chicken erythrocytes in PBS. Positive wells contain an adherent, homogeneous layer of erythrocytes; negative wells contain a nonadherent pellet.

Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50).

5.6.4 Toxicity Studies

The toxicity and/or efficacy of the compositions (e.g., immunogenic formulations) of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the therapies for use in subjects. The dosage of such agents lies preferably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in subjects (e.g., horses). Levels in plasma may be measured, for example, by high performance liquid chromatography.

Further, any assays known to those skilled in the art can be used to evaluate the prophylactic and/or therapeutic utility of a composition (e.g., vaccine formulation), a combination therapy disclosed herein for viral infection or a condition or symptoms associated therewith, an infection other than an a viral infection or a condition or symptom associated therewith, or a condition in which an attenuated chimeric virus of the invention is used as a vector to induce an immune response to an antigen associated with the condition.

5.7 Specific Embodiments of the Invention

The present invention provides a chimeric avian influenza virus, comprising a fusion protein, having (i) an ectodomain comprising a heterologous peptide sequence, which heterologous sequence comprises at least one epitope of a protective antigen of an infectious agent, other than influenza, or of an antigen associated with a disease fused to (ii) a transmembrane and cytoplasmic domain of a glycoprotein encoded by an essential gene of an influenza virus, wherein the fusion protein is incorporated into an avian influenza virus, in which the function of the essential gene is supplied by the fusion protein or by the glycoprotein native to the avian influenza virus. In certain embodiments, the essential gene of an influenza virus is a hemagglutinin (HA) gene. In other embodiments, the essential gene of an influenza virus is a neuraminidase (NA) gene. In certain embodiments, the chimeric avian influenza virus is attenuated. In accordance with these embodiments, the chimeric avian influenza virus may be attenuated by mutations in the NS1 gene.

The present invention provides a chimeric avian influenza virus, comprising a fusion protein, having (i) an ectodomain of an NDV HN protein fused to (ii) a transmembrane and cytoplasmic domain of an influenza virus NA protein, wherein the fusion protein is incorporated into an avian influenza virus, in which the function of the NA protein is supplied by the fusion protein or by the glycoprotein native to the avian influenza virus. In certain embodiments, the chimeric avian influenza virus is attenuated. In accordance with these embodiments, the chimeric avian influenza virus may be attenuated by mutations in the NS1 gene.

The present invention provides an attenuated chimeric influenza virus, comprising a fusion protein, having (i) an ectodomain comprising a heterologous peptide sequence, which heterologous sequence comprises at least one epitope of a protective antigen of an infectious agent, other than influenza, or of an antigen associated with a disease of a protective antigen of an infectious agent, other than influenza fused to (ii) a transmembrane and cytoplasmic domain of a glycoprotein encoded by an essential gene of an influenza virus, wherein the fusion protein is incorporated into an attenuated influenza virus, in which the function of the essential gene is supplied by the fusion protein or by the glycoprotein native to the attenuated influenza virus. In certain embodiments, the essential gene of an influenza virus is a hemagglutinin (HA) gene. In other embodiments, the essential gene of an influenza virus is a neuraminidase (NA) gene.

The present invention provides a chimeric NDV, comprising a fusion protein, having (i) an ectodomain comprising a heterologous peptide sequence, which heterologous sequence comprises at least one epitope of a protective antigen of an infectious agent, other than NDV, or of an antigen associated with a disease fused to (ii) a transmembrane and cytoplasmic domain of a glycoprotein encoded by an essential gene of an NDV, wherein the fusion protein is incorporated into an NDV, in which the function of the essential gene is supplied by the fusion protein or by the glycoprotein native to the NDV.

The present invention provides a chimeric avian influenza virus, comprising a packaged influenza virus NA segment encoding a neuraminidase fusion protein, in which the NA open reading frame is modified so that the nucleotides encoding the NA ectodomain are replaced by nucleotides encoding an ectodomain of a neuraminidase antigen of an infectious agent other than influenza that is anchored by the N-terminus, so that the neuraminidase fusion protein is expressed and incorporated into the chimeric avian influenza virus.

The present invention provides a chimeric avian influenza virus, comprising a packaged influenza virus HA segment encoding a hemagglutinin fusion protein, in which the HA open reading frame is modified so that the nucleotides encoding the HA ectodomain are replaced by nucleotides encoding an ectodomain of a hemagglutinin antigen of an infectious agent other than influenza that is anchored by the C-terminus, so that the hemagglutinin fusion protein is expressed and incorporated into the chimeric avian influenza virus.

The present invention provides a chimeric avian influenza virus, comprising a packaged bicistronic influenza virus HA segment, comprising:

(a) a first open reading frame that encodes an avian influenza hemagglutinin protein, and (b) a second open reading frame that encodes a hemagglutinin fusion protein, in which the nucleotides encoding the hemagglutinin ectodomain are replaced by nucleotides encoding a heterologous peptide sequence, which heterologous sequence comprises at least one epitope of a protective antigen of an infectious agent, other than influenza, or of an antigen associated with a disease that is anchored by the C-terminus, so that both the influenza hemagglutinin and the fusion protein are expressed and incorporated into the chimeric avian influenza virus.

The present invention provides a chimeric avian influenza virus, comprising a packaged bicistronic influenza virus NA segment, comprising:

(a) a first open reading frame that encodes an avian influenza neuraminidase protein, and (b) a second open reading frame that encodes a neuraminidase fusion protein, in which the nucleotides encoding the neuraminidase ectodomain are replaced by nucleotides encoding a heterologous peptide sequence, which heterologous sequence comprises at least one epitope of a protective antigen of an infectious agent, other than influenza, or of an antigen associated with a disease that is anchored by the N-terminus, so that both the influenza neuraminidase and the fusion protein are expressed and incorporated into the chimeric avian influenza virus.

The present invention provides a chimeric avian influenza virus, comprising a packaged influenza virus NA segment encoding a neuraminidase fusion protein, in which the NA open reading frame is modified so that the nucleotides encoding the NA ectodomain are replaced by nucleotides encoding an ectodomain of an HN antigen of NDV, so that the neuraminidase fusion protein is expressed and incorporated into the chimeric avian influenza virus.

In certain embodiments, the chimeric avian influenza virus of paragraphs 209-211 and 213-217 which comprises a packaged NS1 gene segment encoding a modified NS1 protein that reduces the cellular interferon antagonist activity of the virus. In other embodiments, the chimeric avian influenza virus of paragraphs 209-211 and 213-217 which comprises an HA segment having an open reading frame modified to remove the hemagglutinin polybasic cleavage site. In yet other embodiments, the chimeric avian influenza virus of paragraph 215, in which the first open reading frame is modified to remove the hemagglutinin polybasic cleavage site.

The present invention provides a recombinant nucleic acid molecule (e.g., recombinant DNA molecules) encoding the NA segment of paragraphs 213 and 216. The present invention also provides recombinant nucleic acid molecules (e.g., recombinant DNA molecules) encoding the HA segment of paragraphs 214-215.

The present invention provides methods for propagating the chimeric avian influenza viruses of paragraphs 209-211 and 213-218, comprising culturing the chimeric avian influenza viruses in an embryonated egg or a cell line that is susceptible to avian influenza virus infection. The present invention also provides methods for producing an immunogenic formulation, the method comprising:

(a) propagating the chimeric avian influenza virus of paragraphs 209-211 and 213-218 in an embryonated egg or a cell line that is susceptible to avian influenza virus infection; and (b) collecting the progeny virus, wherein the virus is grown to sufficient quantities and under sufficient conditions that the virus is free from contamination, such that the progeny virus is suitable for use in an immunogenic formulation, e.g., vaccine formulation.

The present invention provides an attenuated chimeric influenza virus, comprising a packaged influenza virus NA segment encoding a neuraminidase fusion protein, in which the NA open reading frame is modified so that the nucleotides encoding the NA ectodomain are replaced by nucleotides encoding an ectodomain of a neuraminidase antigen of an infectious agent other than influenza that is anchored by the N-terminus, so that the neuraminidase fusion protein is expressed and incorporated into the attenuated chimeric avian influenza virus.

The present invention provides an attenuated chimeric influenza virus, comprising a packaged influenza virus HA segment encoding a hemagglutinin fusion protein, in which the HA open reading frame is modified so that the nucleotides encoding the HA ectodomain are replaced by nucleotides encoding an ectodomain of a hemagglutinin antigen of an infectious agent other than influenza that is anchored by the C-terminus, so that the hemagglutinin fusion protein is expressed and incorporated into the attenuated chimeric influenza virus.

The present invention provides an attenuated chimeric avian influenza virus, comprising a packaged bicistronic influenza virus HA segment, comprising:

(a) a first open reading frame that encodes an avian influenza hemagglutinin protein, and (b) a second open reading frame that encodes a hemagglutinin fusion protein, in which the nucleotides encoding the hemagglutinin ectodomain are replaced by nucleotides encoding a heterologous protein, said protein containing an epitope of an ectodomain of a protective antigen of an infectious agent other than influenza or of an antigen that is associated with a disease, said fusion protein anchored by the C-terminus, so that both the influenza hemagglutinin and the fusion protein are expressed and incorporated into the attenuated chimeric influenza virus.

The present invention provides an attenuated chimeric influenza virus, comprising a packaged bicistronic influenza virus NA segment, comprising:

(a) a first open reading frame that encodes an avian influenza neuraminidase protein, and (b) a second open reading frame that encodes a neuraminidase fusion protein, in which the nucleotides encoding the neuraminidase ectodomain are replaced by nucleotides encoding heterologous protein, said protein containing an epitope of an ectodomain of a protective antigen of an infectious agent other than influenza or of an antigen that is associated with a disease, said fusion protein anchored by the N-terminus, so that both the influenza neuraminidase and the fusion protein are expressed and incorporated into the attenuated chimeric influenza virus.

In certain embodiments, the attenuated chimeric influenza virus of paragraphs 221-224 which comprises a packaged NS1 gene segment encoding a modified NS1 protein that reduces the cellular interferon antagonist activity of the virus. In certain other embodiments, the attenuated chimeric influenza virus of paragraphs 221-224 which comprises an HA segment having an open reading frame modified to remove the hemagglutinin polybasic cleavage site. In other embodiments, the attenuated chimeric influenza virus of paragraph 223, in which the first open reading frame is modified to remove the hemagglutinin polybasic cleavage site.

The present invention provides recombinant DNA molecules encoding the NA segment of paragraphs 221 and 224.

The present invention also provides recombinant DNA molecules encoding the HA segment of paragraphs 222-223.

The present invention provides methods for propagating the attenuated chimeric influenza viruses of paragraphs 221-225, comprising culturing the attenuated chimeric influenza viruses in an embryonated egg or a cell line that is susceptible to avian influenza virus infection. The present invention also provides methods for producing an immunogenic formulation, the method comprising:

(a) propagating the attenuated chimeric influenza virus of paragraphs 211 and 2221-225 in an embryonated egg or a cell that is susceptible to attenuated influenza virus infection; and (b) collecting the progeny virus, wherein the virus is grown to sufficient quantities and under sufficient conditions that the virus is free from contamination, such that the progeny virus is suitable for use in an immunogenic formulation, e.g., vaccine formulation.

The present invention provides a chimeric NDV, comprising a packaged genome comprising a nucleotide sequence encoding an F protein-fusion protein having the transmembrane and cytoplasmic domains of an F protein and the ectodomain of an antigen of an infectious agent other than NDV that is anchored by the C terminus, so that the F protein-fusion protein is expressed and incorporated into the chimeric NDV.

The present invention provides a chimeric NDV, comprising a packaged genome comprising a nucleotide sequence encoding an HN fusion protein having the transmembrane and cytoplasmic domains of an HN protein and the ectodomain of an antigen of an infectious agent other than NDV that is anchored by the N-terminus, so that the HN fusion protein is expressed and incorporated into the chimeric NDV.

In certain embodiments, the genome of the chimeric NDV of paragraphs 213 and 228-229 comprises a nucleotide sequence encoding an F protein, so that the F protein is expressed and incorporated into the chimeric NDV in addition to the F protein-fusion protein. In other embodiments, the nucleotide sequence encoding the NDV F protein-fusion protein replaces the nucleotide sequence encoding the NDV F protein and the F protein-fusion protein supplies the function of the F protein for the chimeric NDV of paragraph 228.

In certain embodiments, the genome of the chimeric NDV of paragraph 212 and 223-224 comprises a nucleotide sequence encoding an HN protein, so that the HN protein is expressed and incorporated into the chimeric NDV. In other embodiments, the nucleotide sequence encoding the HN fusion protein replaces the nucleotide sequence encoding the NDV HN protein and the HN fusion protein supplies the function of the HN protein for the chimeric NDV of paragraph 229.

The present invention provides methods for propagating the chimeric NDVs of paragraphs 212 and 228-229, comprising culturing the chimeric NDVs in an embryonated egg or a cell line that is susceptible to NDV infection. The present invention also provides a method for producing an immunogenic formulation, the method comprising:

(a) propagating the chimeric NDV of paragraphs 212 and 228-229 in an embryonated egg or a cell; and (b) collecting the progeny virus, wherein the virus is grown to sufficient quantities and under sufficient conditions that the virus is free from contamination, such that the progeny virus is suitable for use in an immunogenic formulation, e.g., vaccine formulation.

The present invention provides embryonated eggs comprising the chimeric viruses of paragraphs 209-210, 212-218 and 228-229. The present invention also provides cell lines comprising the chimeric viruses of paragraphs 209-210, 212-218 and 228-229. The present invention further provides immunogenic formulations comprising the chimeric viruses of paragraphs 209-210, 212-218 and 228-229.

The present invention provides embryonated egg comprising the attenuated chimeric viruses of paragraphs 211 and 221-225. The present invention also provides cell lines comprising the attenuated chimeric viruses of paragraphs 211 and 221-225. The present invention further provides immunogenic formulations comprising the attenuated chimeric viruses of paragraphs 211 and 221-225.

The present invention provides methods of inducing an immune response two infectious agents in an avian, the method comprising administering an effective amount of a chimeric avian influenza virus of paragraphs 209-210 and 213-218. The present invention also provides methods of inducing an immune response two infectious agents in an avian, the method comprising administering an effective amount of a chimeric NDV of paragraphs 212 and 228-229. The present invention further provides methods for inducing an immune response two infectious agents in a subject, the method comprising administering an effective amount of an attenuated chimeric influenza virus of paragraphs 211 and 221-225. In certain embodiments, the subject is a human subject. In other embodiments, the subject is a non-human mammal (e.g., a pig, horse, dog, cat, or bovine). In yet other embodiments, the subject is an avian subject.

6. EXAMPLES

6.1 Engineering of Chimeric Avian Influenza Virus Presenting a Newcastle Disease Virus Epitope The following example describes the production of a exemplary chimeric avian influenza virus. In particular, the example describes the engineering of an avian influenza virus, Influenza A/Vietnam/1203/04 (H5N1), to express and incorporate in its virion a fusion protein comprising the transmembrane and cytoplasmic domains of the avian influenza virus NA protein and the ectodomain of the NDV HN protein. The fusion protein functionally replaces the avian influenza virus NA protein.

6.1.1 Materials and Methods 6.1.1.1 Construction of Plasmids

All plasmid constructs for use in plasmid-only rescue of recombinant viruses, were cloned using the same strategy. Full length cDNAs of viral segments were amplified using PCR with primers that included SapI restriction sites, which allowed the insertion of the PCR product into the SapI sites of the pPol1-SapI-Rb plasmid (Flandorfer et al., 2003, J. Virol. 77:9116-9123; Nakaya et al., 2001, J. Virol. 75:11868-11873; both of which are incorporated herein by reference in their entireties). Sequences of all PCR inserts were confirmed (Mount Sinai DNA sequencing facility, NY), and nucleotide changes that had been introduced by PCR were corrected using a QuickChange XL site-directed mutagenesis kit (Stragene, La Jolla, Calif.) when appropriate. The GenBank sequences for the Influenza A/Vietnam/1203/04 (H5N1), Influenza A/WSN/33 (WSN) and NDV are provided in Table 2

TABLE 2

GenBank Accession Numbers of Virus Segments

| Virus | Segment | Genbank Accession No. |
|---|---|---|
| H5N1 | NS | AY651553 (SEQ ID NO: 1) |
| | M | AY651388 (SEQ ID NO: 2) |
| | NP | AY651499 (SEQ ID NO: 3) |
| | HA | AY818135 (SEQ ID NO: 4) |
| | NA | AY651447 (SEQ ID NO: 5) |
| | PA | AY818132 (SEQ ID NO: 6) |
| | PB1 | AY818129 (SEQ ID NO: 7) |
| | PB2 | AY651719 (SEQ ID NO: 8) |
| WSN | NA | L25817 (SEQ ID NO: 9) |
| NDV B1 | HN | AF309418 (SEQ ID NO: 10) |

6.1.1.2 Construction of Chimeric Viral Segment

A cDNA encoding the NDV B1 HN ectodomain and the cytoplasmic tail (CT) and transmembrane (TM) domains of the neuraminidase (NA) of influenza A/WSN/33 (A/Vietnam/1203/04-A/WSN/33 $NA_{(CT+TM)}$-NDV B1 $HN_{(ecto)}$ was constructed using recombinant techniques well known in the art. The construct encodes 19 nucleotides of the 3' noncoding region of the WSN NA vRNA, nucleotides encoding amino acids 1-36 (108 nucleotides) of the NA coding region, corresponding to the cytoplasmic tail and transmembrane domains of the NA protein plus the first amino acid of the NA ectodomain, followed by nucleotides encoding amino acids 51-568 of the NDV B1 HN protein (HN ectodomain), two sequential stop codons, 157 untranslated nucleotides of the WSN NA reading frame and the 5' noncoding region of the WSN vRNA (FIG. 1).

6.1.1.3 Construction of Plasmid Constructs Encoding Chimeric H5N1-NDV

Plasmid constructs were created in order to produce, by plasmid only rescue, a chimeric virus based on H5N1 (the host virus) engineered to present an NDV surface glycoprotein. The segment of H5N1 encoding the surface glycoprotein NA was selected to be replaced with a recombinant segment comprising a nucleotide sequence encoding the CT and TM domains of the NA protein plus the first amino acid of the NA ectodomain of A/WSN/33 and the ectodomain of the HN protein of NDV-B1. The fusion protein, A/Vietnam/1203/04-A/WSN/33 $NA_{(CT+TM)}$-NDV B1 $HN_{(ecto)}$, supplies the neuraminidase activity for the chimeric avian influenza virus. See FIG. 1 for a schematic of the chimeric segment.

The remaining seven segments of H5N1 listed in Table 2 (NS, M, NP, HA, PA, PB1 and PB2) were cloned into pPol1 to produce pPol1VN1203-NS, pPol1VN1203-M, pPol1VN1203-NP, pPol1VN1203-HA, pPol1VN1203-PA, pPol1VN1203-PB1 and pPol1VN1203-PB2, respectively. To ensure attenuation of the chimeric H5N1 virus, the segment encoding H5N1 HA was altered to convert the native polybasic amino acid sequence immediately before the HA cleavage site (nucleotides 1013-1039 of the H5N1 HA coding sequence) to a consensus sequence based on avirulent avian strains of influenza A H5. The amino acid sequence in this region was altered from QRERRRKKRG (SEQ ID NO:11; amino acids 2-11 of SEQ ID NO:14) to QRETRG (SEQ ID NO:12; amino acids 2-7 of SEQ ID NO:16), replacing the underlined amino acids with threonine (FIG. 2). The codon usage in this region was further altered to reduce the number of adenosine residues in order minimize the chance of reintroduction of adenosine residues in this sequence by polymerase slippage and the resultant introduction of basic amino acid residues into the HA cleavage site. Only synonymous mutations were introduced into the avirulent I-IA sequence (FIG. 3). The resultant segment encoding the altered HA glycoprotein, corresponding low-virulence avian influenza A strains, was cloned in to a pPol1 plasmid as previously described, pPol1VN1203-HALO. With the exception of PB1 and PB2, the gene products encoded by the segments of H5N1 were unaltered from the genbank sequences. The sequences of PB1 and PB2 were altered as a result of the introduction of the SapI restriction sites. A non-synonymous substitution with the nucleotide guanine at position 32 of the coding sequence of PB1 resulted in a lysine to arginine mutation; the non-synonymous substitution with the nucleotide thymine at position 1393 of the coding sequence of PB2 resulted in a proline to serine mutation. All gene products of H5N1 have an adenosine residue at position 4 of the vRNA.

In addition to the plasmid construct encoding wild-type H5N1 NS, pPol1VN1203-NS, three pPol1 constructs encoding differently truncated versions of the H5N1 NS gene segment were also generated. The additional constructs encoding altered versions of the NS segment may be of use in further attenuating the resulting chimeric virus (see, e.g., U.S. Pat. No. 6,669,943, which is incorporated herein by reference in its entirety). The three constructs varied in the number of amino acids of the NS1 protein (from the amino terminus) that are expressed by the plasmid construct. pPol1VN1203 NS1-126, pPol1VN1203 NS1-99 and pPol1VN1203 NS1-73 thus encode only the first 126, only the first 99 and only the first 73 amino acids as counted from the amino terminus of the wild type NS1 protein, respectively. The mutagenesis to generate truncated constructs did not affect the open reading frame of NEP (FIG. 4).

6.1.1.4 Rescue of Infectious Virus from Plasmid Constructs

Recombinant, chimeric viruses of the invention are rescued by any means described herein or known in the art. For example, 293T, HEp-2 or A549 cells may be transfected with eight of the described pPol1 plasmids, selected to achieve a desired level of viral attenuation and so that all eight segments are represented, i.e., the cells are transfected with pPol1VN WSN-NA$_{(CT+TM)}$-NDV B1 HN$_{(ecto)}$; pPol1VN1203-HA or pPol1VN1203-HALO; pPol1VN1203-NS, pPol1VN1203 NS1-126, pPol1VN1203 NS1-99 or pPol1VN1203 NS1-73; pPol1VN1203-M; pPol1VN1203-NP; pPol1VN1203-PA; pPol1VN1203-PB1 and pPol1VN1203-PB2. The cells are further transfected with eukaryotic expression plasmids encoding NA, PA, PB1 and PB2, which are required for replication and transcription of the vRNAs. After overnight incubation, the transfected cells may be co-cultured with chicken embryo fibroblasts to amplify the produced virus. After a further 2 to 3 day incubation, the supernatant of the co-culture may be injected into the allantoic cavities of 9- or 10-day old embryonated chicken eggs for propagation. For attenuated viruses, 7-day old eggs, which do not have a competent interferon system may be used. Virus growth may be confirmed by assaying the harvested allantoic fluid for hemagglutination according to standard protocols known in the art.

6.2 Engineering of Chimeric Newcastle Disease Virus Presenting a Foreign Epitope The following example describes the production of exemplary chimeric NDVs. In particular, the example describes the engineering of a chimeric NDV to express and incorporate into its virion a fusion protein comprising the transmembrane and cytoplasmic domains of a necessary protein of NDV and the ectodomain of an avian influenza virus. The example demonstrates that such a chimeric virus induces protection against subsequent infection by both influenza virus and NDV.

The example also describes the engineering of an exemplary NDV to express and incorporate into its virion a fusion protein comprising the cytoplasmic domain of the NDV F protein and the ectodomain and transmembrane domain of human keratinocyte growth factor receptor (KGFR).

6.2.1 Materials and Methods 6.2.1.1 Cell Lines

MDCK, HEp-2 and A549 cells were grown in Dulbecco's Modified Eagle Medium (DMEM) supplemented with 10% fetal calf serum and 1% penicillin/streptomycin. The full length cDNA of the Hitchner B1 strain of NDV has been published under genbank accession number AF375823 (Nakaya et al., 2001, J. Virol. 75:11868-11873, which is incorporated herein by reference in its entirety).

6.2.1.2 Construction of Plasmids

The engineering of recombinant cDNA of NDV to encode a foreign protein has been described (Nakaya et al., 2001, J. Virol. 75:11868-11873). Briefly, the full length cDNA of NDV is introduced into a plasmid between the T7 promoter and the hepatitis delta virus (HDV) ribozyme and T7 terminator to create pNDV/B1. The NDV cDNA has a XbaII site engineered between the P and M genes that allows the introduction of foreign sequences as an extratransciptional unit into the NDV genome (FIG. 5). All inserted genes are engineered to contain, sequentially, a gene end; 5'-TTAGAAAAAA-3' (SEQ ID NO:18); intercistronic nucleotide T; and the gene start sequence; 5'-ACGGGTAGAA-3' (SEQ ID NO:19) (the GE/GS sequence).

rNDV/B1-KGFR, rNDV/B1-KGFR/F-CT, and rNDV/B1-H7HA/F-TMCT viruses were generated by reverse genetics from the full-length cDNA copies derived from the NDV Hitchner B1 strain. To construct these viruses, the KGFR or H7 HA (HA protein from influenza A subtype H7N2) ORF was cloned as an extra transcriptional unit between the P and M genes of NDV/B1 cDNA, as described for other ORFs (Nakaya et al., 2001, J. Virol. 75:11868-11873 and Nakaya et al., 2004, J. Virol. 78:9366-9375, both of which are hereby incorporated by reference in their entireties). KGFR and H7 HA are both transmembrane proteins, each comprising a TM and CT domain. In the KGFR/F-CT construct, the CT domain of the KGFR protein was replaced by that of the F protein of NDV. In the H7 HA/F-TMCT construct, the TM and CT domains of the H7 HA protein were replaced by those of the F protein of NDV. The recombinant NDV viruses were rescued from cDNA and propagated using standard techniques well known in the art (see, e.g., Swayne et al., 2003, Avian Dis. 47: 1047-1053 and Nakaya et al., 2001, both of which are hereby incorporated by reference in their entireties). The insertion of the new transcriptional units in the recombinant viruses was confirmed by reverse transcription PCD followed by sequencing analysis.

For example, the ectodomain (ECTO) of the H5 HA gene was produced by PCR using the following primers (which include the GE/GS sequence): NheI-H5HA P, 5'-CG GCT AGC TTAGAAAAAA T ACGGTAGAA GTGAA ACTAGT CC GCC ACC ATG GAA AGA ATA GTG ATT GCC TTT GCA-3' (SEQ ID NO:20) and HpaI-H5HA P, 5'-CG GTT AAC CTG ATA AGC CCC CAT TGA TTC TAA T-3' (SEQ ID NO:21). The H5 HA$_{ecto}$ PCR fragment was digested with NheI and HpaI and cloned into pSL1180 (pSLH5HA$_{ecto}$). (Amersham Pharmacia Biotech) (pSLH5HA$_{ecto}$). The TM and CT of the NDV F gene were also amplified by PCR using the following primers, HpaI-NDVF (TM+CYTO) P, 5'-CG GTT AAC CTC ATT ACC TAT ATC GTT TTG ACT-3' (SEQ ID NO:22), SacI-NheI-NDVF (TM+CYTO) M, 5'-CG GAG CTC AA GCT AGC TTA TCA CAT TTT TGT AGT GGC TCT CAT CTG-3' (SEQ ID NO:23). To fuse with H5 $HA_{ecto}$, the TM and CT of the NDV F gene were digested with HpaI and SacI and then cloned into $pSLH5HA_{ecto}$ to obtain the hybrid fusion gene. Finally, the plasmid containing the hybrid H5 HA gene was digested with NheI and cloned between the P and M genes of the rNDV cDNA.

6.2.1.3 Western Blot and Biological Analysis

Viruses from cell or allantoic extracts were purified by ultracentrifugation through a 30% sucrose cushion. Levels of incorporated protein were monitored by western blot analysis using specific antibody and routine techniques.

The ability of the chimeric NDV to present the non-viral protein KGFR in vivo was determined by immunizing BALB/c mice with $3\times10^7$ pfu of the chimeric virus intraperitoneally, followed by a booster immunization using the same dose three weeks later. Two weeks after the second immunization, sera from inoculated animals was tested for the presence of antibodies to KGFR by immunostaining MDCK cells transfected with a plasmid encoding KGFR.

An in vivo system was designed to evaluate whether immunization with the rNDV comprising the hybrid H7 HA/F-TMCT was able to provide protection against subsequent infection by H7 or NDV. Two-week old chicks were immunized by eye-drop method with 100 μl of three vaccines, rNDV, rNDV-H7 HA/F-TMCT and Sham. At 4 weeks of age, 100 μl comprising $10^{5.1}$ mean embryo infectious dose of HP AIV (A/Steele/ACC-10/59 [H7N7]) was administered through the choanal slit. The birds were observed for signs and lesions of HP AIV infection. Mortality was recorded, and all survivors were euthanized by sodium pentobarbital (100 mg/kg) at 6 weeks of age.

6.2.2 Results 6.2.2.1 Presentation of KGFR by Chimeric NDV Expressing KGFR or KGFR/F-CT Chimeric viruses rNDV/B1-KGFR and rNDV/B1-KGFR/F-CT were grown in the allantoic cavity of 10-day old chicken embryonated eggs. Purified viruses were tested for the presence of KGFD or KGFR/F-CT by Western blot analysis using a murine anti-KGFR antibody. A positive response was detected in the samples isolated from eggs inoculated with rNDV/B1-KGFR/F-CT but not with rNDV/B1-KGFR (FIG. 6).

Each of these chimeric viruses were also used to immunize three BALB/c mice. Sera from the immunized animals was assayed for the presence of KGFR antibodies. Animals immunized with rNDV/B1-KGFR virus did not develop detectable levels of KGFR antibodies using this assay. In contrast, all three animals immunized with rNDV/B1-KGFR/F-CT virus were positive by this assay for the presence of KGFR antibodies.

6.2.2.2 Protection against H7 Infection by Immunization with rNDV-H7 HA/F-TMCT

The TM and CT domains of the wild-type H7 HA were replaced by the TM and CT domains of the NDV F protein to generate a hybrid HA protein, $H7HA_{ecto}$ $NDV/F_{(TM+CT)}$. In a Western blot analysis, both the control rNDV expressing the complete ORF of H7 HA, rNDV-H7HA, and the chimeric rNDV expressing the hybrid $H7HA_{ecto}$ $NDV/F_{(TM+CT)}$, rNDV-$H7HA_{ecto}$-$NDV/F_{(TM+CT)}$, generated a positive reaction to the H7 antibody; however, the signal from rNDV-$H7HA_{ecto}$-$NDV/F_{(TM+CT)}$ was visibly many times stronger (FIG. 7). When chicks immunized once with rNDV-$H7HA_{ecto}$-$NDV/F_{(TM+CT)}$ were subsequently challenged with a lethal dose of H7 influenza, 9 out of 10 (90%) of the immunized chicks survived. When chicks immunized once with rNDV-$H7HA_{ecto}$-$NDV/F_{(TM+CT)}$ were subsequently challenged with a lethal dose of NDV, 10 out of 10 (100%) of the immunized chicks survived.

6.3 Engineering of Chimeric Newcastle Disease Virus Presenting a Foreign Epitope The following example describes the production of chimeric modified NDVs. In particular, a recombinant NDV was produced to improve virulence of the NDV backbone used in Example 6.2. The example demonstrates that the improved virulence of the rNDV also improved the immunogenicity of immunogenic formulations comprising chimeric viruses based on the rNDV.

6.3.1 Materials and Methods

Unless otherwise stated all Materials and Methods described in the section are identical to those described and exemplified in Example 6.2, supra.

6.3.1.1 Generation of Rndvs with a Modified Cleavage Site in their F Proteins

Recombinant NDV viruses rNDV/F2aa and rNDV/F3aa viruses, which have two or three amino acid mutations at the F cleavage site of NDV Hitchner B1 strain were generated by reverse genetics. Briefly, to generate rNDV/F2aa, the PCR fragment was generated by using primers, forward: F2aa-1(+) 5'-GGA TCC CGG TTG GCG CCC TCC AGG (SEQ ID NO:24), and reverse F2aa-1(−) 5'-AAGGCGCCtCTGTCTCCgCCC TCC AGA TGT AGT CAC AG-3' (SEQ ID NO:25) and the full-length NDV B1 clone, plasmid pT7NDV/B1, as template. The next PCR fragment was generated by using primers, forward F2aa-2(+) 5'-GGcGGAGACAGaGGCGCCTTA TAG GCG CCA TTA TTG G-3' (SEQ ID NO:26), and reverse F2aa-2(−) 5'-CCA TAT TCC CAC CAG CTA GAT TGT-3' (SEQ ID NO:27) and the pT7NDV/B1 as template. The nucleotides shown in lower case are mutated to modify the amino acid sequence of the cleavage site of the F protein from that of the NDV/B1 strain (GGRQGR↓L) to GRRQRR↓L. These two overlapping PCR fragments (the overlap is underlined in the primer sequences) were combined by PCR using primers, F2aa-1(+) and F2aa-2(−). The resulting PCR fragment, which contains the entire F gene was cloned into pSL1180 (Amersham Pharmacia Biotech) and named pSLF2aa. The StuI-NotI fragment (nt 4646 to 4952) of pSLF2aa was excised to replace the corresponding fragment in the pT7NDV/B1 plasmid, resulting in the formation of the pT7NDV/F2aa plasmid, which was used to generate rNDV/F2aa virus by reverse genetics. For generation of rNDV/F3aa, PCR mutagenesis was performed by the same strategy as described above using primers, forward, F3aa-1(+) 5'-GGA TCC CGG TTG GCG CCC TCC AGG-3' (SEQ ID NO:28); reverse, F3aa-1(−) 5'-AAaGCGCCtCTGTCTCCgCCC TCC AGA TGT AGT CAC AG-3' (SEQ ID NO:29); forward, F3aa-2(+) 5'-GGcGGAGACAGaGGCGCtTTA TAG GCG CCA TTA TTG G-3' (SEQ ID NO:30); reverse, F3aa-2(−) 5'-CCA TAT TCC CAC CAG CTA GAT TGT-3' (SEQ ID NO:31) (mutated nucleotides are indicated with lower case) and the pT7NDV/B1 as template. These two overlapping PCR fragments (the overlap region is underlined in the primer sequences) were combined by PCR using primers F3aa-1(+) and F3aa-2(−), resulting in modification of the cleavage site from GGRQGR↓L to GRRQRR↓F. The StuI-NotI fragment (nt 4646 to 4952) of pSLF3aa was excised to replace the corresponding fragment in the pT7NDV/B1 plasmid, resulting in the formation of the pT7NDV/F3aa plasmid, which was used to generate rNDV/F3aa virus.

6.3.1.2 Generation of a Fusogenic rNDV Vector Expressing the Chimeric H7 HA Protein.

To construct the chimeric H7 HA gene as an extra transcriptional unit of the rNDV/F3aa genome, the fragment containing the transmembrane (TM) and the cytoplasmic tail (CYTO) of the NDV F gene was initially produced by PCR using primers, HpaNDV F (TM+CYTO), 5'-cgGT TAA CCT CAT TAC CTA TAT CGT TTT GAC T-3' (SEQ ID NO:32) and SacNheNDVF (TM+CYTO)M, 5'-cg GAG CTC AAG CTA GCT TAT CAC ATT TTT GTA GTG GCT CTC ATC TG-3' (SEQ ID NO:33) and the plasmid containing the NDV F gene as a template. This PCR product was digested with Sac I and Hpa I and then cloned into the plasmid, pNhe-NDV-GE/GS possessing the gene end and the gene start signal of NDV, resulting in the formation of plasmid, pNhe-NDV-GE/GS-NDVF (TM+CYTO). As the next step, allowing the connection of the fragment containing H7 HA ectodomain with the fragment of the TM and CYTO region of the NDV F, the H7HA ectodomain was produced by PCR using the primers, SpeH7(ECTO)P, 5'-cgACT AGT CCG CCA CCA TGA ACA CTC AAA TTC TGG CAT TCA T-5' (SEQ ID NO:34), HpaH7(ECTO)M, 5'-cgG TTA ACG TCT TTG TAT CCA CTA CTC AAT TTC AC-3' (SEQ ID NO:35) and plasmid containing H7 HA gene from A/chicken/NY/13142-5/94 (H7N2) as template. This PCR product was digested with Spe I and Hpa I and then inserted into the cassette plasmid, pNhe-NDV-GE/GS-NDVF (TM+CYTO). In a final step, the cassette plasmid, pNhe-NDV-GE/GS-NDV F(TM+CYTO) was digested with Nhe I to cut out the chimeric H7 HA gene. This fragment DNA was cloned between the P and M genes of pT7NDV/F3aa, forming pT7NDV/F3aa-chimericH7. The rNDV/F3aa virus expressing the chimeric H7 HA protein was then rescued from pT7NDV/F3aa-chimericH7 using methods describe, supra.

6.3.1.3 Viral Growth Kinetics rNDV/B1, rNDV/F2aa, rNDV/F3aa, rNDV/B1-H7, or rNDV/F3aa-chimericH7 viruses (100 PFU/egg) were inoculated into 10-day-old embryonated chicken eggs. Allantoic fluids were harvested to determine viral titers at different time points (24 hrs, 48 hrs, and 72 hrs). The 50% tissue culture infective dose ($TCID_{50}$) of each virus present in the allantoic fluid was determined by immunofluorescence assay (IFA). For this purpose, ninety-six well plates containing Vero cells were infected with serial 10-fold dilutions of the samples, and the presence of NDV proteins or chimeric H7 HA protein was determined by IFA.

6.3.2 Immunofluorescence Assays.

6.3.2.1 Immunofluorescence Assays

MDCK cells infected with transfectant influenza virus were fixed and permeabilized with ice cold methanol. Viral antigens were detected with anti-NDV HN monoclonal antibody (7B1), anti-influenza H1 HA monoclonal antibody (2G9) and anti-influenza H5 HA polyclonal serum. For the analysis of NDV growth and viral protein expression, confluent Vero cells were infected with the recombinant viruses, and harvested at different time points (24, 48, and 72 hrs). Infected cells were fixed with 2.5% formaldehyde containing 0.1% Triton X-100. Fixed cells were treated with anti-rabbit NDV polyclonal antibody or anti-chicken AIV H7 polyclonal serum, washed, and stained with fluorescein isothiocyanate (FITC)-conjugated anti-chicken immunoglobulins (DAKO) for AIV H7 HA protein or Texas Red-conjugated anti-rabbit immunoglobulins (Molecular Probe) for the NDV viral proteins. Viral protein expression was examined by fluorescence microscopy.

6.3.2.2 Mean Death Time

To check the pathogenicity of recombinant viruses in embryonated chicken eggs, mean death time (MDT) was determined. Briefly, five 10-day-old embryonated chicken eggs were infected with serial 10-fold dilutions of viruses. The eggs were incubated at 37° C. and monitored two times daily for 7 days. The time to kill embryos was recorded. The highest dilution that killed all embryos was determined to be the minimum lethal dose. The MDT was calculated as the mean time for the minimum lethal dose to kill the embryos.

6.3.2.3 Immunization and Challenge of Chickens

White Leghorn chickens were vaccinated once or twice by eyedrop in the conjunctival sac with $10^{5.7-6.1}$ mean chicken embryo infectious doses ($EID_{50}$) of rNDV/F3aa-chimericH7, or twice with $10^{5.7-6.3}$ $EID_{50}$ of parental NDV/B1 (pNDV), or twice with sterile tissue culture media (sham) at 2 and 4 weeks-of-age. At 6 weeks-of-age, the chickens were challenged intranasally with the Fontana strain of velogenic NDV (vvNDV) ($10^{5.1}$ $EID_{50}$ per bird) or A/Human/Steele/59 (H7N7) HPAI ($10^{5.1}$ $EID_{50}$ per bird). The survivors were bled and euthanized on 14 days post challenge. Hemagglutination inhibition (HI) serological titers were determined using standard procedures.

6.3.3 Results 6.3.3.1 Generation of Fusogenic rNDV Mutants

Figures 8A, 8B:
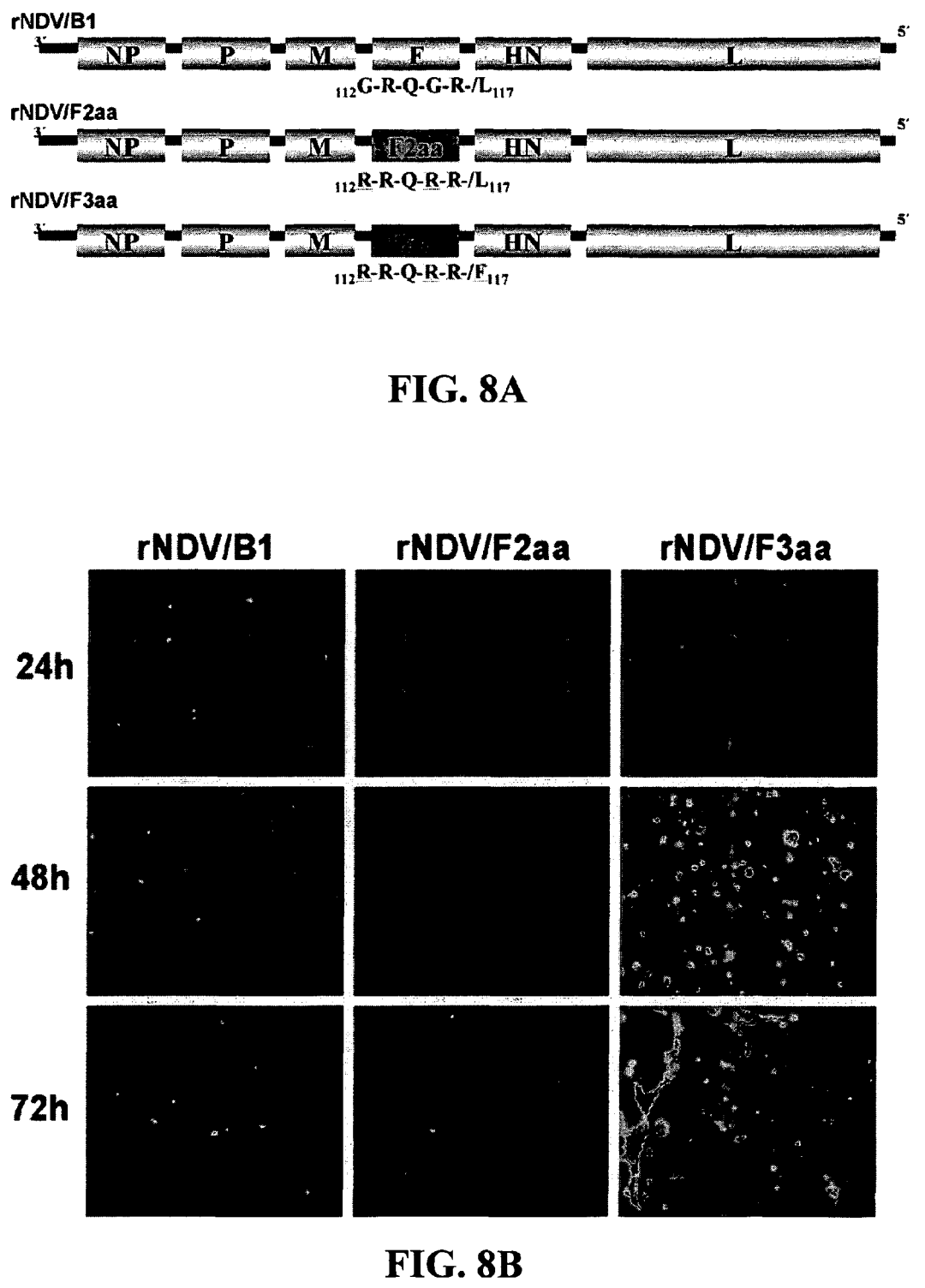

To improve the fusogenic characteristics of the rNDV backbone, two rNDV mutants, rNDV/F2aa and rNDV/F3aa viruses, were developed in which the cleavage site of the F protein was replaced with one of two variant multi-basic cleavage sites, which can be activated by ubiquitously expressed proteases (e.g., furin proteases) (FIG. 8A). Infection of chicken embryo fibroblast cells (CEF) with rNDV/F2aa and rNDV/F3aa, and not with rNDV/B1, resulted in syncytia formation in the absence of exogenously added protease (FIG. 8B). In addition, rNDV/F3aa induced syncytia more rapidly in CEF cells than rNDV/F2aa. It was thus postulated that improved spreading of the virus in immunized animals may enhance immunogenicity against inserted foreign protein. Thus the fusogenic rNDV/F3aa was selected as a backbone vector to develop a bivalent vaccine designed to protect poultry against AIV and NDV.

6.3.3.2 Mean Death Time Analysis of rNDV Platform Vectors in Embryonated Chicken Eggs.

NDV can be classified as highly virulent (velogenic), intermediate (mesogenic), or nonvirulent (lentogenic) on the basis of its pathogenicity for chickens. Since the presence of an F protein with a multibasic cleavage site is known to be an NDV virulence factor, we assessed the pathogenicity of rNDVs with modified F protein in 10-day-old embryonated chicken eggs. The mean death time (MDT) of chicken embryos infected with NDVs correlates with virulence in vivo. Lentogenic strains (causing asymptomatic infections in birds) are characterized by MDTs of more than 90 hrs, mesogenic strains (causing respiratory disease in birds) have MDTs between 60 to 90 hrs, and velogenic strains (causing severe disease in birds) have MDTs under 60 hrs. The MDT of rNDV/F2aa was indicative of a lentogenic strain, while that of rNDV/F3aa was typical of a mesogenic strain. Neither of these strains had MDTs typical of a highly pathogenic (velogenic) strain (Table 3).

TABLE 3

| MDT of rNDVs in Embryonated Chicken Eggs | | | |
|---|---|---|---|
| Virus | Trypsin Requirement (cell Culture) | Inoculation $EID_{50}$ | MDT, hr |
| rNDV/B1 | Yes | 10 | 113 |
| | | 1 | 122 |
| rNDV/F2aa | No | 10 | 100 |
| | | 1 | 104 |
| rNDV/F3aa | No | 10 | 80 |
| | | 1 | 84 |
| rNDV/B1-H7 | Yes | 10 | Alive |
| | | 1 | Alive |
| rNDV/3aa-chimericH7 | No | 10 | 128 |
| | | 1 | 140 |

Based on these data, rNDV/F3aa vector would not represent a threat to birds and is thus suitable as a backbone to develop a bivalent vaccine for the protection of poultry against AIV and NDV.

6.3.3.3 Generation of a Fusogenic rNDV Vector Expressing the Ectodomain of AIV HA Protein.

Figures 9A, 9B:
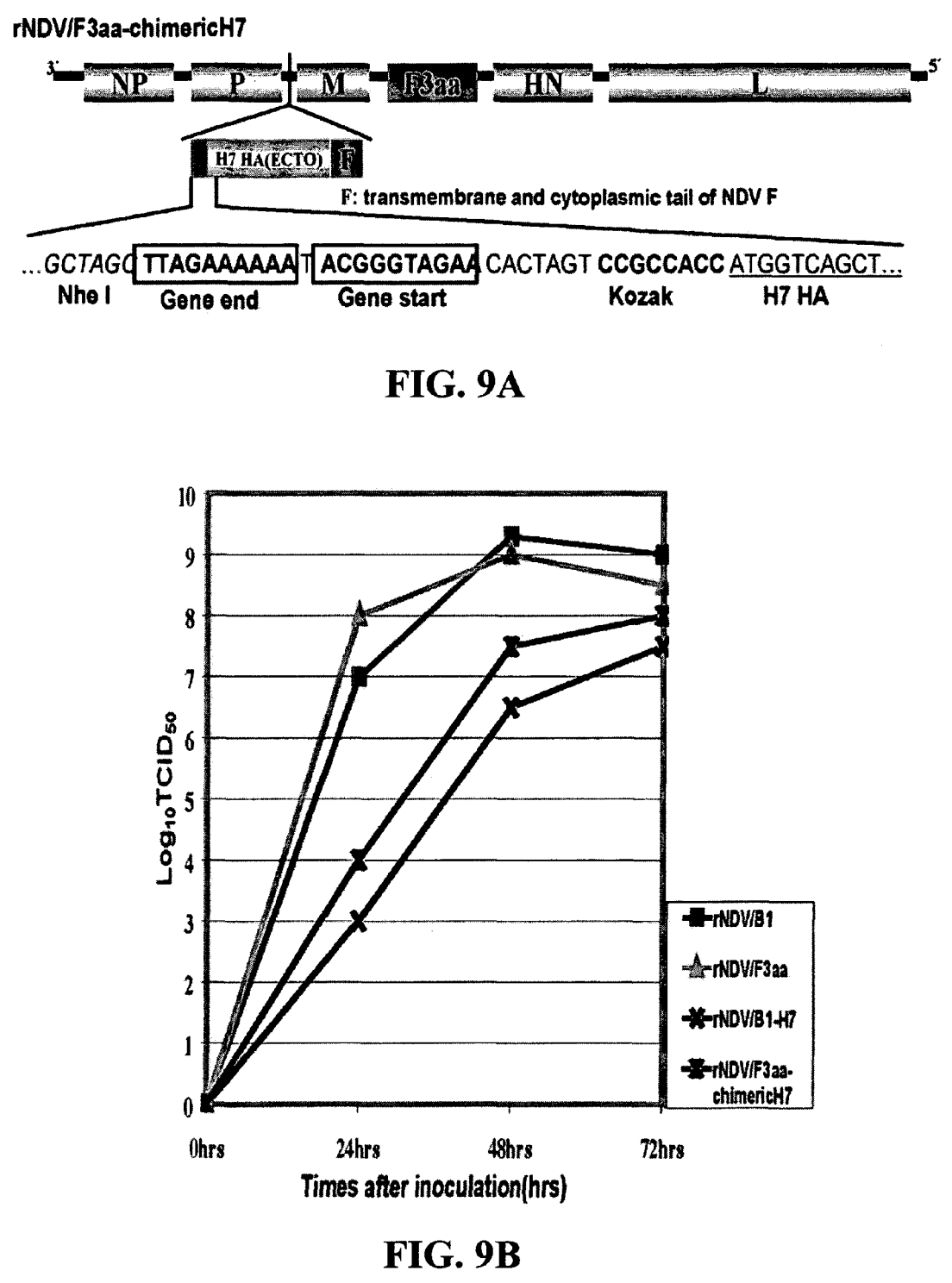
Figures 9C, 9D:
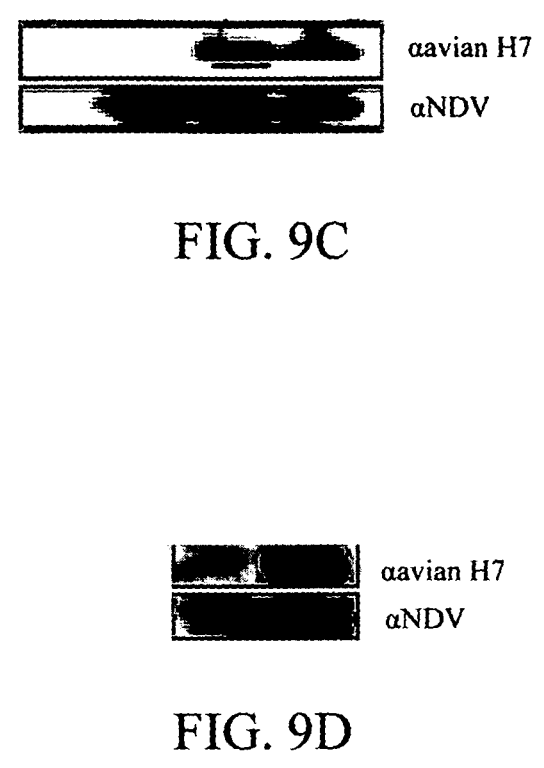

The gene encoding the H7 HA protein from A/chicken/NY/13142-5/94(H7N2) was incorporated into the rNDV/F3aa vector as described supra, resulting in the formation of rNDV/F3aa-chimericH7 (FIG. 9A). The growth kinetic of rNDV/F3aa-chimericH7 in embryonated chicken eggs was compared to that of the parental rNDV/F3aa (FIG. 9B). The virus expressing the chimeric H7 HA protein grew more slowly than the virus without the insert and maximal titers were about a log lower. Interestingly, the MDT of this virus was that of a lentogenic strain (128~140 hrs) (Table 3). Expression of the chimeric H7 HA protein from rNDV/F3aa-chimericH7 was confirmed by western blotting of infected Vero cells 36 hrs post-infection (FIG. 9C).

6.3.3.4 Improved Incorporation of AIV H7 HA Protein into rNDV Virions.

To determine if expression of the chimeric H7 HA protein containing the heterologous transmembrane and cytoplasmic tail regions of the NDV F protein would be associated with enhanced incorporation into rNDV virions, rNDV/B1-H7 and rNDV/F3aa-chimericH7 virions were purified as described in §6.3. The amounts of H7 HA protein or NDV viral protein from rNDV/B1-H7 or rNDV/F3aa-chimericH7 were measured by western blotting using anti-chicken AIV H7 polyclonal antibody or anti-rabbit NDV polyclonal serum. As expected, incorporation of chimeric H7 HA protein into rNDV virions was significantly increased as compared to that of wt H7 HA protein (FIG. 9D). This data suggests that the transmembrane and cytoplasmic tail regions of the NDV F protein play a major role in the improved incorporation of the foreign protein into the viral surface.

6.3.3.5 Immunization and Challenge of Chickens.

Following one or two vaccinations with rNDV/F3aa-chimericH7, 50-80% of the chickens had hemagglutination inhibition (HI) titers to H7 AIV and 90-100% of the chickens had HI titers to NDV (Table 4A and B). While all chickens immunized twice with the parental NDV/B1 (pNDV) had HI titers to NDV but none had titers to H7 AIV. All sterile tissue culture media (sham) infected birds lacked HI titers to either virus. When challenged with vvNDV, 100% of rNDV/F3aa-chimericH7 and pNDV immunized chickens were protected. By comparison, 90% of rNDV/F3aa-chimericH7 vaccinated chickens were protected from HPAI H7 virus, but none of pNDV vaccinated chickens were protected from HPAI H7 virus. By contrast, 100% and 70% of sham infected birds died when challenged by vvNDV and HPAI H7 virus, respectively. The survivors mounted an amnestic response evident as a four fold or greater rise in HI titer for the respective challenge virus except for the three survivors in the sham-HPAI H7 virus challenge group which had no serological evidence of being infected.

TABLE 4A

| HI Serology of Chickens Immunized with Chimeric Viruses Before Challenge | | |
|---|---|---|
| Vaccine Group* | AIV/H7 antigen | NDV antigen |
| rNDV/F3aa-chimericH7, 1X | 8/10(11) | 10/10(49) |
| rNDV/F3aa-chimericH7, 1X | 7/10(10) | 10/10(49) |
| rNDV/F3aa-chimericH7, 2X | 8/10(13) | 9/10(56) |
| rNDV/F3aa-chimericH7, 2X | 5/10(9) | 9/10(60) |
| pNDV, 2X | 0/10 | 10/10(34) |
| pNDV, 2X | 0/10 | 10/10(56) |
| Sham, 2X | 0/10 | 0/10 |
| Sham, 2X | 0/10 | 0/10 |

TABLE 4B

| HI Serology of Chickens Immunized with Chimeric Viruses After Challenge (14 Days post challenge) | | | | |
|---|---|---|---|---|
| Vaccine Group* | Challenge Virus | No Survivors | AIV/H7 antigen | NDV antigen |
| rNDV/F3aa-chimericH7, 1X | vNDV | 10/10 | 9/10(15) | 10/10(416) |
| rNDV/F3aa-chimericH7, 1X | HPAIV | 9/10 | 9/9(2,048) | 9/9(37) |
| rNDV/F3aa-chimericH7, 2X | vNDV | 10/10 | 7/10(17) | 10/10(315) |
| rNDV/F3aa-chimericH7, 2X | HPAIV | 9/10 | 8/8(955) | 8/8(30) |
| pNDV, 2X | vNDV | 10/10 | 0/10 | 10/10(294) |
| pNDV, 2X | HPAIV | 0/10 | NA | NA |
| Sham, 2X | vNDV | 0/10 | NA | NA |
| Sham, 2X | HPAIV | 3/10 | 0/3 | 0/3 |

Sham = sterile tissue culture fluid

HPAIV = A/human/Steele/59 (H7N7) virus

HI serology is shown as number of chickens with HI-positive serum/number of chickens vaccinated; parenthetical values are geometric mean titer (GMT)

*n = 10 birds per group, 1X = one vaccination, 2X = 2 vaccinations

The publicationentitled "Engineered Viral Vaccine COnstructs with Dual Specificity: Avian Influenza and Newcastle Disease," by Man-Seong Park et al., in PNAS 103: 8203-8208 (2006) is incorporated herein by reference in its entirety.

6.4 Equivalents

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Throughout this application various publications are cited. Their contents are hereby incorporated by reference into the present application in their entireties for all purposes.

What is claimed is:

1. A chimeric Newcastle Disease Virus (NDV), comprising a packaged genome comprising a nucleotide sequence encoding an F-fusion protein, wherein the F-fusion protein comprises the transmembrane and cytoplasmic domains of an NDV F protein and at least one epitope of an ectodomain of a protective antigen of an infectious agent other than NDV or an antigen associated with a disease that is anchored by the C-terminus of the antigen, so that the F-fusion protein is expressed and incorporated into the chimeric NDV, and wherein the antigen is not a paramyxovirus antigen.

2. A chimeric Newcastle Disease Virus (NDV), comprising a packaged genome comprising a nucleotide sequence encoding an HN-fusion protein, wherein the HN-fusion protein comprises the transmembrane and cytoplasmic domains of an NDV HN protein and at least one epitope of an ectodomain of a protective antigen of an infectious agent other than NDV or an antigen associated with a disease that is anchored by the N-terminus of the antigen, so that the HN protein-fusion protein is expressed and incorporated into the chimeric NDV, and wherein the antigen is not a paramyxovirus antigen.

3. The chimeric NDV of claim 1 in which the genome comprises a nucleotide sequence encoding an F-fusion protein, wherein the F-fusion protein comprises the transmembrane and cytoplasmic domains of an NDV F protein and an ectodomain of a protective antigen of an infectious agent other than NDV or an antigen associated with a disease that is anchored by the C-terminus of the antigen, so that the F-fusion protein is expressed and incorporated into the chimeric NDV, and wherein the antigen is not a paramyxovirus antigen.

4. The chimeric NDV of claim 1 in which the genome comprises a nucleotide sequence encoding an HN-fusion protein, wherein the HN-fusion protein comprises the transmembrane and cytoplasmic domains of an NDV HN protein and an ectodomain of a protective antigen of an infectious agent other than NDV or an antigen associated with a disease that is anchored by the C-terminus of the antigen, so that the F-fusion protein is expressed and incorporated into the chimeric NDV, and wherein the antigen is not a paramyxovirus antigen.

5. The chimeric NDV of claim 1 in which the genome comprises a nucleotide sequence encoding an F protein, so that the F protein is expressed and incorporated into the chimeric NDV.

6. The chimeric NDV of claim 1 in which the nucleotide sequence encoding the F-fusion protein replaces the nucleotide sequence encoding the NDV F protein and the F-fusion protein supplies the function of the F protein, wherein the at least one epitope of an ectodomain of a protective antigen of an infectious agent other than NDV or an antigen associated with a disease is selected to be incorporated into the F-fusion protein such that it supplies the function of the ectodomain of the F protein.

7. The chimeric NDV of claim 2 in which the genome comprises a nucleotide sequence encoding an HN protein, so that the HN protein is expressed and incorporated into the chimeric NDV.

8. The chimeric NDV of claim 2 in which the nucleotide sequence encoding the HN-fusion protein replaces the nucleotide sequence encoding the NDV HN protein and the HN-fusion protein supplies the function of the HN protein, wherein the at least one epitope of an ectodomain of a protective antigen of an infectious agent other than NDV or an antigen associated with a disease is selected to be incorporated into the HN-fusion protein such that it supplies the function of the ectodomain of the F protein.

9. A chimeric Newcastle Disease Virus (NDV), comprising a packaged genome comprising a nucleotide sequence encoding an NDV F-fusion protein, wherein the F-fusion protein comprises the transmembrane and cytoplasmic domains of an NDV F protein and an ectodomain of a hemagglutinin antigen of an influenza virus that is anchored by the C-terminus of the antigen, so that the F-fusion protein is expressed and incorporated into the chimeric NDV.

10. A chimeric Newcastle Disease Virus (NDV), comprising a packaged genome comprising a nucleotide sequence encoding an HN-fusion protein, wherein the HN-fusion protein comprises the transmembrane and cytoplasmic domains of an NDV HN protein and an ectodomain of a neuraminidase antigen of an influenza virus that is anchored by the N-terminus, so that the HN-fusion protein is expressed and incorporated into the chimeric NDV.

11. The chimeric NDV of claim 9, wherein the influenza virus is an avian influenza virus.

12. The chimeric NDV of claim 10, wherein the influenza virus is an avian influenza virus.

13. The chimeric NDV of claim 1, wherein the chimeric NDV has an NDV strain LaSota backbone.

14. The chimeric NDV of claim 2, wherein the chimeric NDV has an NDV strain LaSota backbone.

15. The chimeric NDV of claim 9, wherein the chimeric NDV has an NDV strain LaSota backbone.

16. The chimeric NDV of claim 1, wherein the transmembrane and cytoplasmic domains of the F-fusion protein are from NDV strain LaSota.

17. The chimeric NDV of claim 2, wherein the transmembrane and cytoplasmic domains of the F-fusion protein are from NDV strain LaSota.

18. The chimeric NDV of claim 9, wherein the transmembrane and cytoplasmic domains of the F-fusion protein are from NDV strain LaSota.

19. The chimeric NDV of claim 5, wherein the F protein is genetically modified at the cleavage site, such that fusogenic activity is increased.

20. The chimeric NDV of claim 9 in which the genome comprises a nucleotide sequence encoding an F protein, so that the F protein is expressed and incorporated into the chimeric NDV.

21. The chimeric NDV of claim 20, wherein the F protein is genetically modified at the cleavage site, such that fusogenic activity is increased.

22. The chimeric NDV of claim 21, wherein the genetically modified cleavage site comprises a multi-basic cleavage site.

23. The chimeric NDV of claim 9 in which the nucleotide sequence encoding the F-fusion protein replaces the nucleotide sequence encoding the NDV F protein and the F-fusion protein supplies the function of the F protein, wherein the ectodomain of a hemagglutinin antigen of an influenza virus is selected to be incorporated into the F-fusion protein such that it supplies the function of the ectodomain of the F protein.

24. The chimeric NDV of claim 1, wherein the F-fusion protein either contains no amino acid residues of the ectodomain of the F protein, or the F-fusion protein contains a fragment of the ectodomain of the F protein that does not retain the activity of the ectodomain of the F protein.

25. The chimeric NDV of claim 2, wherein the HN-fusion protein contains either no amino acid residues of the ectodomain of the HN protein, or it contains a fragment of the ectodomain of the HN protein that does not retain the activity of the ectodomain of the HN protein.

26. The chimeric NDV of claim 9, wherein the F-fusion protein contains no amino acid residues of the ectodomain of the F protein.

27. The chimeric NDV of claim 9, wherein the F-fusion protein contains a fragment of the ectodomain of the F protein that does not retain the activity of the ectodomain of the F protein.

28. The chimeric NDV of claim 10, wherein the HN-fusion protein contains either no amino acid residues of the ectodomain of the HN protein, or it contains a fragment of the ectodomain of the HN protein that does not retain the activity of the ectodomain of the HN protein.

29. A chimeric Newcastle Disease Virus (NDV), comprising a packaged genome comprising a nucleotide sequence encoding an NDV F-fusion protein, wherein the F-fusion protein comprises the transmembrane and cytoplasmic domains of an NDV F protein and an ectodomain of a hemagglutinin antigen of an influenza virus that is anchored by the C-terminus of the antigen, so that the F-fusion protein is expressed and incorporated into the chimeric NDV, wherein the F-fusion protein contains a fragment of the ectodomain of the F protein that does not retain the activity of the ectodomain of the F protein, and wherein the fragment of the ectodomain of the F protein is between 1 and 15 residues of the ectodomain of an F protein that are immediately adjacent to the transmembrane domain of the F protein.

30. The chimeric NDV of claim 1, wherein the sequence that encodes the F-fusion protein is inserted between the P and M genes of the NDV genome.

31. The chimeric NDV of claim 2, wherein the sequence that encodes the HN-fusion protein is inserted between the P and M genes of the NDV genome.

32. The chimeric NDV of claim 9, wherein the sequence that encodes the F-fusion protein is inserted between the P and M genes of the NDV genome.

33. The chimeric NDV of claim 1, wherein the chimeric NDV is attenuated.

34. The chimeric NDV of claim 2, wherein the chimeric NDV is attenuated.

35. The chimeric NDV of claim 9, wherein the chimeric NDV is attenuated.

36. The chimeric NDV of claim 10, wherein the chimeric NDV is attenuated.

37. An immunogenic composition comprising the chimeric NDV of claim 33.

38. An immunogenic composition comprising the chimeric NDV of claim 34.

39. An immunogenic composition comprising the chimeric NDV of claim 35.

40. An immunogenic composition comprising the chimeric NDV of claim 36.

41. A method for inducing an immune response to two infectious agents in an avian subject or a human subject, the method comprising administering the chimeric NDV of claim 1.

42. A method for inducing an immune response to two infectious agents in an avian subject or a human subject, the method comprising administering the chimeric NDV of claim 2.

43. A method for inducing an immune response to two infectious agents in an avian subject or a human subject, the method comprising administering the chimeric NDV of claim 9.

* * * * *